United States Patent
Rake et al.

(10) Patent No.: US 6,871,759 B2
(45) Date of Patent: Mar. 29, 2005

(54) PLATEN PUMP

(75) Inventors: Kenneth W. Rake, Laguna Niguel, CA (US); Orvile L. Judge, Columbus, GA (US); Donald M. Earhart, Irvine, CA (US); Charles J. McPhee, Huntington Beach, CA (US)

(73) Assignee: I-Flow Corporation, Lake Forest, CA (US)

( * ) Notice: Subject to any disclaimer, the term of this patent is extended or adjusted under 35 U.S.C. 154(b) by 0 days.

(21) Appl. No.: 10/678,038

(22) Filed: Sep. 30, 2003

(65) Prior Publication Data

US 2004/0108333 A1 Jun. 10, 2004

Related U.S. Application Data

(63) Continuation of application No. 10/078,063, filed on Feb. 18, 2002, now Pat. No. 6,626,329, which is a division of application No. 08/987,601, filed on Dec. 9, 1997, now Pat. No. 6,358,239, which is a continuation of application No. 08/617,679, filed on Mar. 19, 1996, now abandoned, which is a continuation-in-part of application No. 08/358,083, filed on Feb. 7, 1995, now abandoned, which is a continuation of application No. 08/008,790, filed on Jan. 22, 1993, now abandoned, which is a continuation-in-part of application No. 07/898,958, filed on Jun. 15, 1992, now abandoned, which is a continuation-in-part of application No. 07/824,855, filed on Jan. 24, 1992, now Pat. No. 5,911,716.

(51) Int. Cl.$^7$ .............................................. B65D 35/28
(52) U.S. Cl. ............................. 222/103; 128/DIG. 12; 128/DIG. 13; 604/31; 604/135; 604/890.1
(58) Field of Search ......................... 222/92, 95, 103, 222/386; 128/DIG. 12, DIG. 13; 604/31, 131–135, 140–143, 145–147, 150, 151, 153–155, 214, 216–218, 225–228, 232, 890.1, 891.7

(56) References Cited

U.S. PATENT DOCUMENTS

| | | |
|---|---|---|
| D11,248 S | 3/1879 | Fairbanks |
| 480,785 A | 8/1892 | Schan |

(Continued)

FOREIGN PATENT DOCUMENTS

| | | |
|---|---|---|
| CA | 0594443 | 3/1960 |
| CH | 404870 | 7/1966 |
| CH | 408146 | 3/1969 |
| CH | 635245 | 3/1983 |
| DE | 3507818 | 7/1986 |
| DE | 4039191 | 11/1991 |
| EP | 0178371 | 4/1986 |
| EP | 426319 | 8/1991 |
| FR | 2102412 | 4/1972 |
| GB | 245988 | 1/1926 |
| GB | 0472203 | 9/1937 |
| GB | 1216534 | 12/1970 |
| GB | 2197691 | 5/1988 |
| NO | 76374 | 3/1950 |

*Primary Examiner*—Joseph A. Kaufman
(74) *Attorney, Agent, or Firm*—Knobbe Martens Olson & Bear LLP

(57) ABSTRACT

Disclosed is an infusion pump for expelling a fluid from a collapsible fluid reservoir to a patient. The pump includes a housing having a chamber therein for receiving the fluid reservoir. A first wall is provided on the housing for contacting the fluid reservoir, and a second wall is movable from a first position distanced from the first wall to form the chamber therebetween, and a second position relatively closer to the first wall. Advancing the movable wall from the first position to the second position expels fluid from the collapsible reservoir at a substantially constant rate by applying increasing force on the fluid reservoir through the dispensation cycle. Preferably, the first and second walls are provided with non-planar complementary surface configurations for contacting the collapsible reservoir. Retraction mechanisms for retracting the movable wall from the second position to the first position, and user readable indicium of the status of the dispensation cycle are also disclosed.

7 Claims, 45 Drawing Sheets

U.S. PATENT DOCUMENTS

| | | | |
|---|---|---|---|
| D42,809 S | 7/1912 | Tatum | |
| 2,043,325 A | 6/1936 | Jackson, Jr. | 128/234 |
| D109,549 S | 5/1938 | Dabroski | |
| 2,667,872 A | 2/1954 | Smith | 128/216 |
| 2,688,964 A | 9/1954 | Smith | 128/216 |
| 2,784,716 A | 3/1955 | Broman | 128/227 |
| 2,848,141 A | 8/1958 | Intagliata | 222/101 |
| 2,864,367 A | 12/1958 | Mende | 128/261 |
| 2,864,368 A | 12/1958 | Senger | 128/261 |
| 3,029,983 A | 4/1962 | Wagenhals | 222/94 |
| 3,048,171 A | 8/1962 | Grau | 128/214 |
| 3,111,125 A | 11/1963 | Schulte | 128/350 |
| 3,144,866 A | 8/1964 | Ellis | 128/232 |
| 3,151,616 A | 10/1964 | Selton | 128/214 |
| 3,177,870 A | 4/1965 | Salem, Jr. et al. | 128/214 |
| 3,375,824 A | 4/1968 | Krakauer et al. | 128/214 |
| 3,384,080 A | 5/1968 | Muller | 128/214 |
| 3,428,046 A | 2/1969 | Remer et al. | 128/349 |
| 3,451,393 A | 6/1969 | Samoff | 128/214 |
| 3,468,308 A | 9/1969 | Bleman | 128/214 |
| 3,469,578 A | 9/1969 | Bierman | 128/214 |
| 3,565,292 A | 2/1971 | Jinotti | 222/103 |
| 3,595,232 A | 7/1971 | Leibinson | 128/214 |
| D221,911 S | 9/1971 | Ericson et al. | |
| 3,625,401 A | 12/1971 | Terry | 222/103 |
| 3,640,276 A | 2/1972 | Dancy, Jr. | 128/214 F |
| 3,640,277 A | 2/1972 | Adelberg | 222/61 |
| 3,647,117 A | 3/1972 | Hargest | 222/100 |
| 3,662,928 A | 5/1972 | Pogorski et al. | 222/211 |
| 3,667,466 A | 6/1972 | Ralph | 128/287 |
| 3,670,926 A | 6/1972 | Hill | 222/217 |
| 3,731,681 A | 5/1973 | Blackshear et al. | 128/214 F |
| D227,184 S | 6/1973 | Stevens et al. | |
| 3,818,910 A | 6/1974 | Harris | 128/232 |
| 3,847,304 A | 11/1974 | Cohen | 222/105 |
| 3,895,631 A | 7/1975 | Buckles et al. | 128/213 |
| 3,895,741 A | 7/1975 | Nugent | 222/103 |
| 3,902,635 A | 9/1975 | Jinotti | 222/103 |
| 3,941,132 A | 3/1976 | Lenaghan | 128/296 |
| 3,965,905 A | 6/1976 | Schoenholz et al. | 128/285 |
| 4,033,479 A | 7/1977 | Fletcher et al. | 222/61 |
| D245,539 S | 8/1977 | Lindsey | |
| D245,540 S | 8/1977 | Lindsey | |
| 4,077,544 A | 3/1978 | Malacheski et al. | 222/95 |
| 4,095,110 A | 6/1978 | Bunch | 280/445 T |
| 4,140,117 A | 2/1979 | Buckles et al. | 128/213 R |
| 4,157,771 A | 6/1979 | Smith | 222/103 |
| D255,936 S | 7/1980 | Cullis et al. | |
| 4,212,299 A | 7/1980 | Yokokoji et al. | 128/272 |
| 4,265,241 A | 5/1981 | Portner et al. | 128/260 |
| 4,274,407 A | 6/1981 | Scarlett | 128/213 R |
| 4,282,986 A | 8/1981 | af Ekenstam et al. | 222/1 |
| 4,284,209 A | 8/1981 | Barbour, Jr. | 222/1 |
| 4,313,439 A | 2/1982 | Babb et al. | 128/214 F |
| 4,337,769 A | 7/1982 | Olson | 128/214 F |
| 4,410,323 A | 10/1983 | Hodosh et al. | 604/212 |
| D272,762 S | 2/1984 | Tanner, II | |
| 4,468,221 A | 8/1984 | Mayfield | 604/152 |
| 4,560,382 A | 12/1985 | Isono | 604/408 |
| 4,581,018 A | 4/1986 | Jassawalla et al. | 604/153 |
| D284,035 S | 5/1986 | de Leeuwe et al. | |
| 4,619,652 A | 10/1986 | Eckenhoff et al. | 604/415 |
| 4,634,427 A | 1/1987 | Hannula et al. | 604/93 |
| 4,650,469 A | 3/1987 | Berg et al. | 604/131 |
| D291,491 S | 8/1987 | Larkin | |
| 4,699,615 A | 10/1987 | Fischell et al. | 604/131 |
| 4,741,736 A | 5/1988 | Brown | 604/134 |
| 4,756,450 A | 7/1988 | Negaty-Hindi et al. | 222/95 |
| 4,769,008 A | 9/1988 | Hessel | 604/132 |
| 4,772,263 A | 9/1988 | Dorman et al. | 604/132 |
| D298,567 S | 11/1988 | Morris | |
| 4,781,689 A | 11/1988 | Sealfon et al. | 604/134 |
| 4,883,473 A | 11/1989 | Thomas | 604/217 |
| 4,898,582 A | 2/1990 | Faste | 604/141 |
| 4,915,693 A | 4/1990 | Hessel | 604/132 |
| 4,950,245 A | 8/1990 | Brown et al. | 604/153 |
| 4,955,871 A | 9/1990 | Thomas | 604/217 |
| 4,966,585 A | 10/1990 | Gangemi | 604/131 |
| 4,968,301 A | 11/1990 | di Palma et al. | 604/132 |
| 4,969,873 A | 11/1990 | Steinbach et al. | 604/93 |
| 4,991,742 A | 2/1991 | Chang | 222/95 |
| 5,053,031 A | 10/1991 | Borsanyi | 604/891.1 |
| 5,062,840 A | 11/1991 | Holt et al. | 604/385.1 |
| 5,090,963 A | 2/1992 | Gross et al. | 604/132 |
| 5,098,202 A | 3/1992 | Rosenbaum | 383/67 |
| 5,167,632 A | 12/1992 | Eid et al. | 604/136 |
| 5,167,633 A | 12/1992 | Mann et al. | 604/141 |
| 5,176,641 A | 1/1993 | Idriss | 604/133 |
| 5,176,644 A | 1/1993 | Srisathapat et al. | 604/141 |
| 5,178,609 A | 1/1993 | Ishikawa | 604/131 |
| 5,281,202 A | 1/1994 | Weber et al. | 604/132 |
| 5,911,716 A | 6/1999 | Rake et al. | 604/890.1 |
| 6,251,098 B1 | 6/2001 | Rake et al. | 604/408 |
| 6,358,239 B1 * | 3/2002 | Rake et al. | 604/890.1 |
| 6,367,666 B1 * | 4/2002 | Hou et al. | 222/386.5 |
| 6,626,329 B2 * | 9/2003 | Rake et al. | 222/103 |
| 2002/0123735 A1 | 9/2002 | Rake et al. | 604/407 |

* cited by examiner

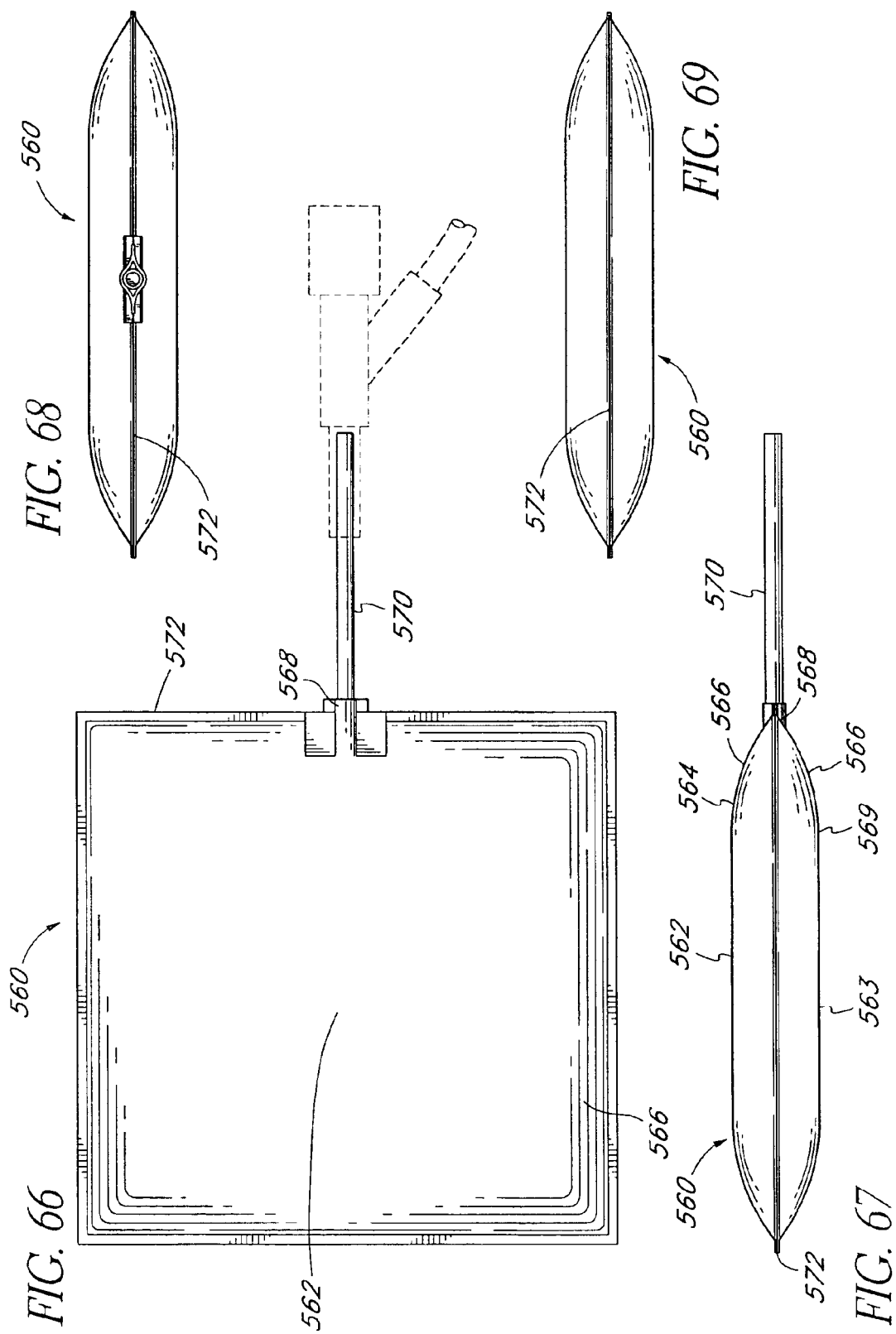

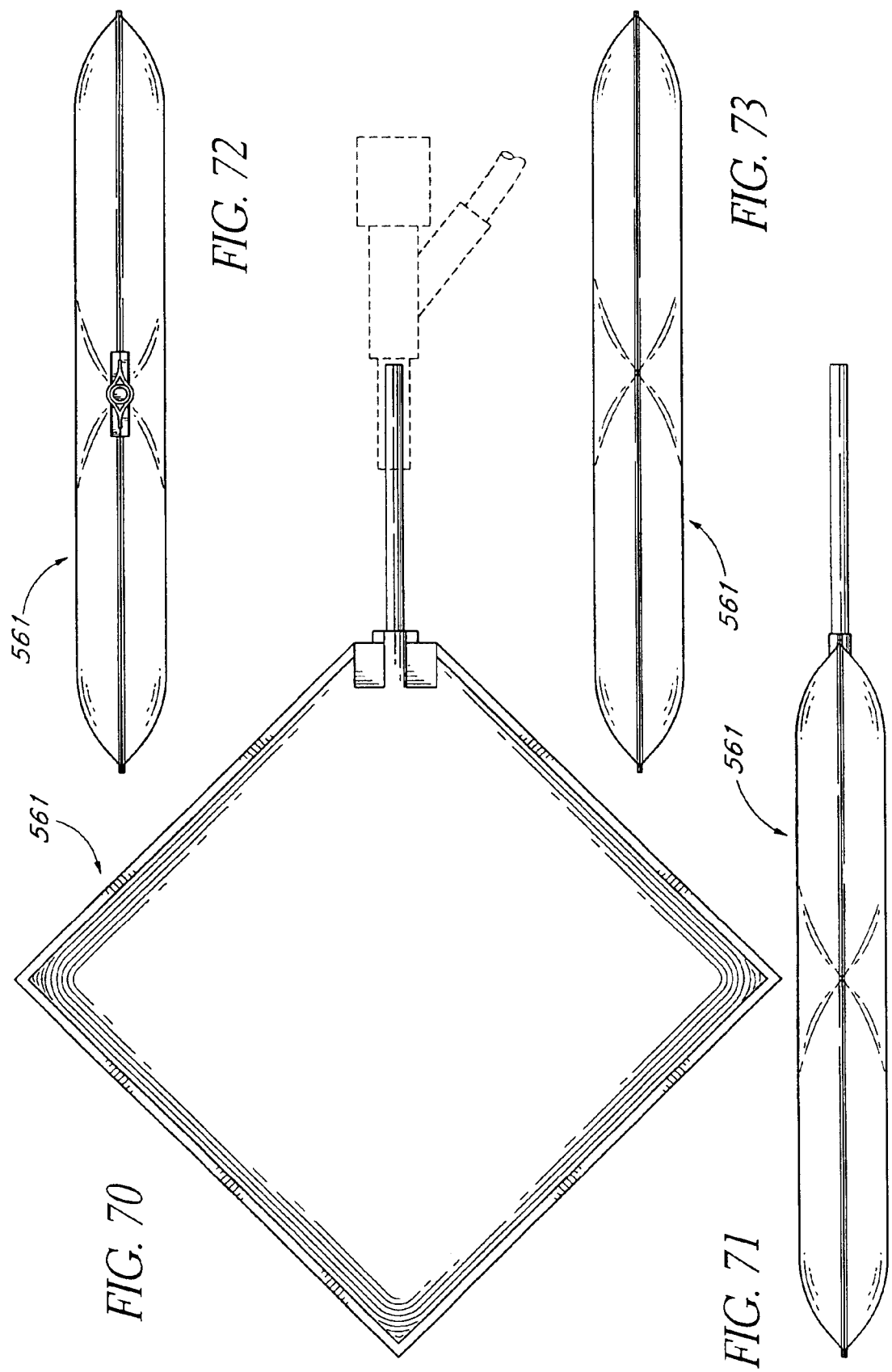

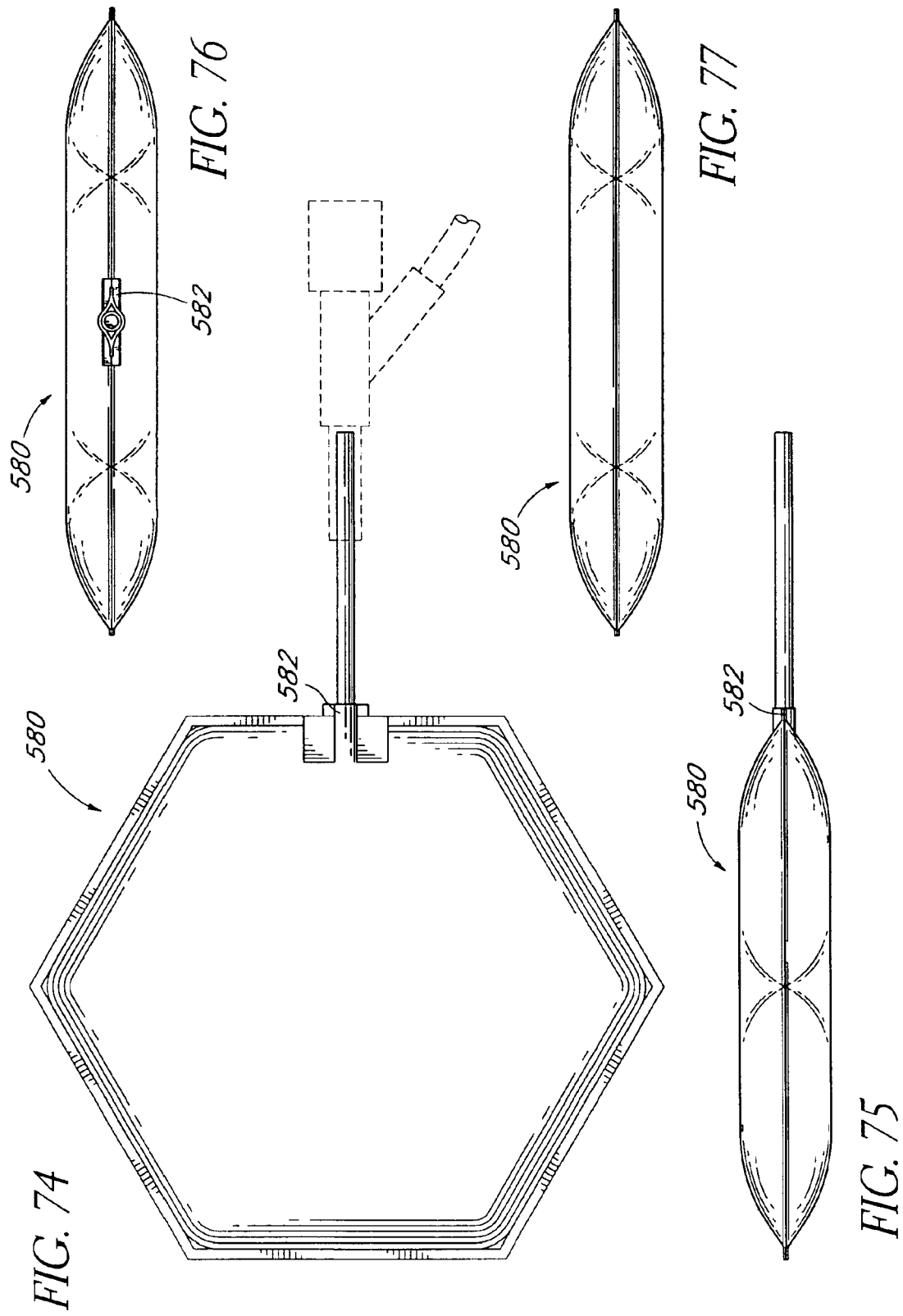

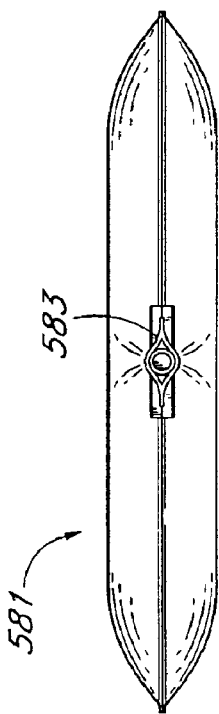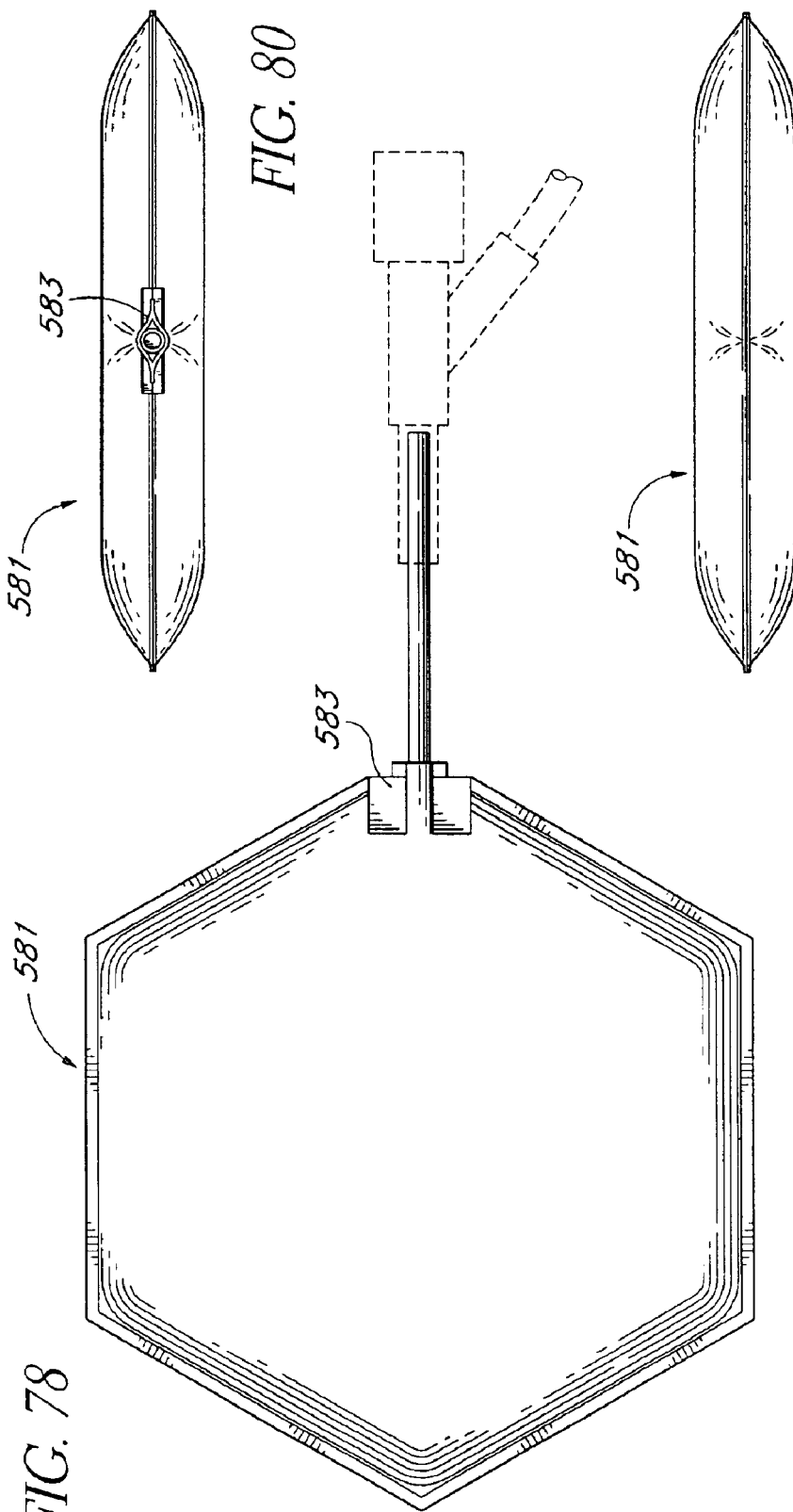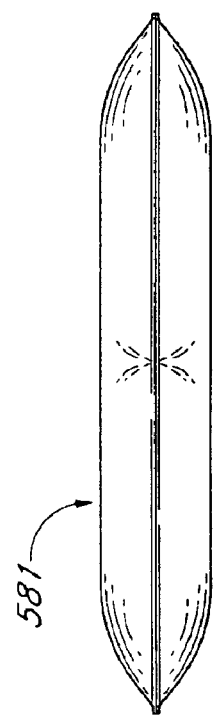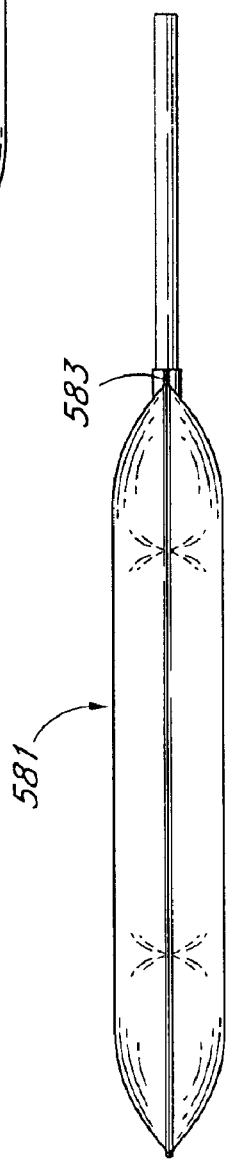

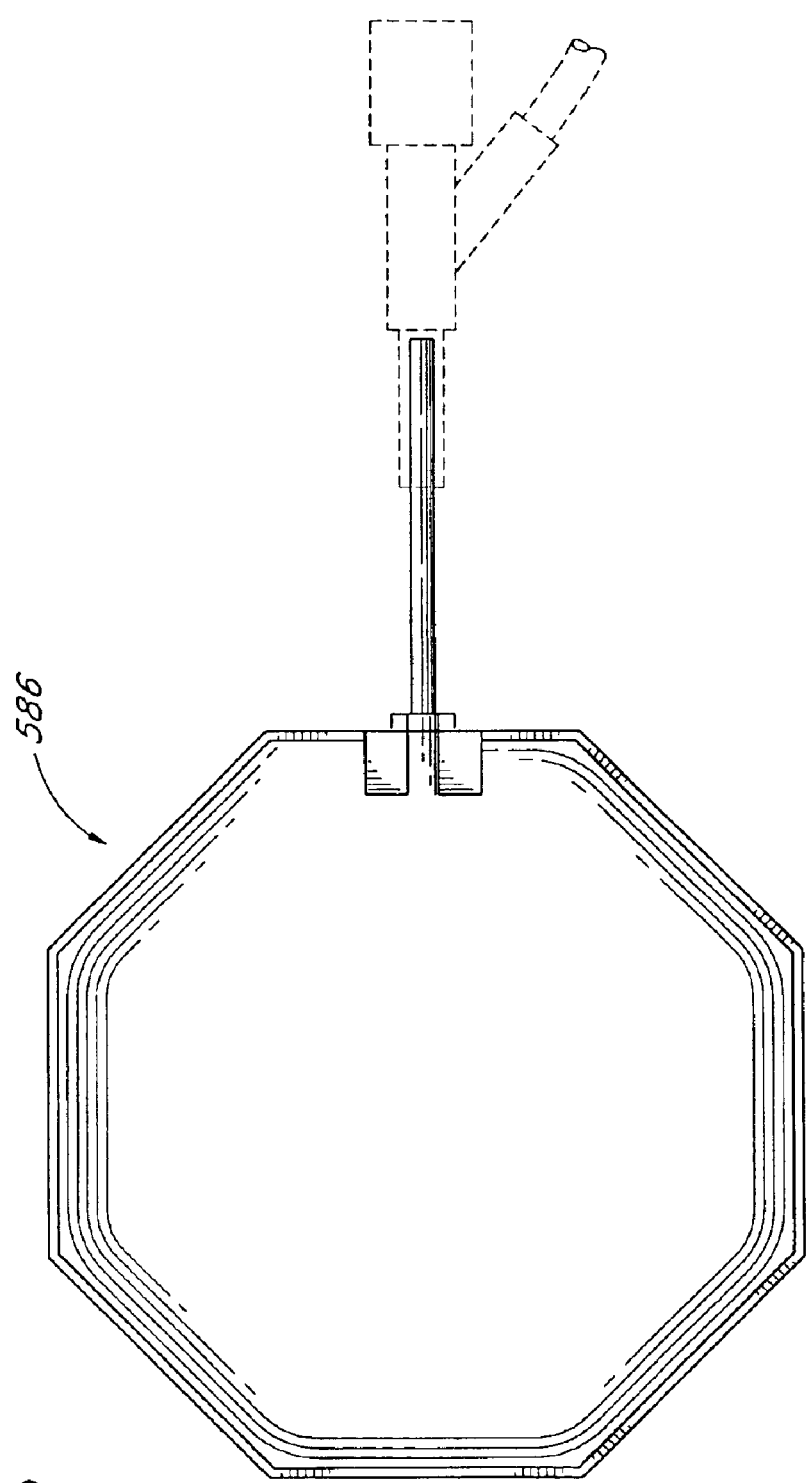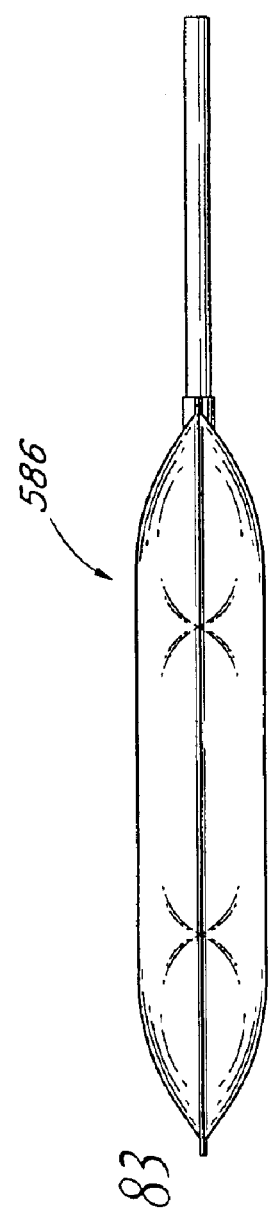
FIG. 82
FIG. 83

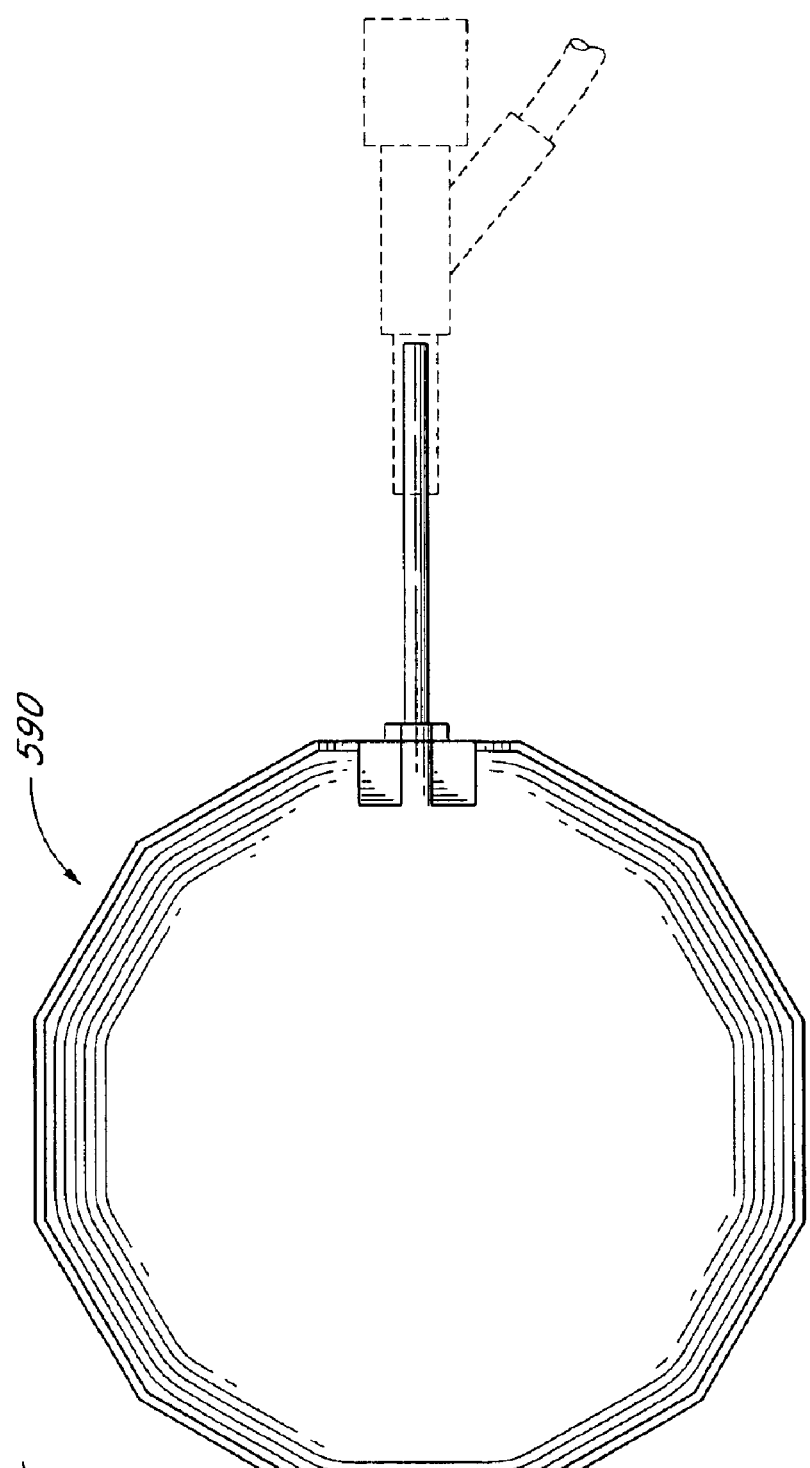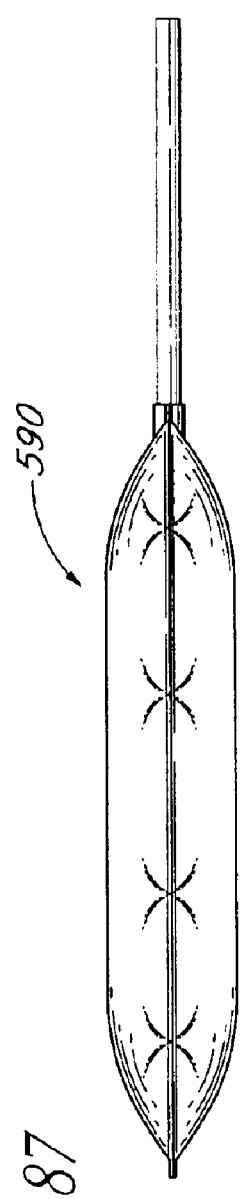
FIG. 86
FIG. 87

PLATEN PUMP

This application is a continuation of U.S. patent application Ser. No. 10/078,063, filed Feb. 18, 2002, now U.S. Pat. No. 6,626,329, which is a divisional application of U.S. patent application Ser. No. 08/987,601, filed Dec. 9, 1997, now U.S. Pat. No. 6,358,239, which is a continuation of U.S. patent application Ser. No. 08/617,679, filed Mar. 19, 1996, now abandoned which is a continuation-in-part of U.S. patent application Ser. No. 08/358,083, filed Feb. 7, 1995, now abandoned, which is a continuation of U.S. patent application Ser. No. 08/008,790, filed Jan. 22, 1993, now abandoned, which is a continuation-in-part of U.S. patent application Ser. No. 07/898,958, filed Jun. 15, 1992, now abandoned, which is a continuation-in-part of U.S. patent application Ser. No. 07/824,855, filed Jan. 24, 1992, now U.S. Pat. No. 5,911,716.

BACKGROUND OF THE INVENTION

1. Field of the Invention

This invention relates to a low cost drug delivery system useful in delivering drugs, from pliable plastic containers.

2. Description of the Related Art

Many drugs in the healthcare field are administered to a patient on a continuous basis. Continuous delivery of a drug to a patient was initially achieved by placing a drug delivery bag filled with a drug above the patient and letting gravity force the drug from the bag into the patient. Although this method has proven successful for many applications, its drawbacks included a) an unsteady flow to the patient due to the changing height of the intravenous infusion site relative to the drug bag, b) the awkwardness of requiring the patient to remain below the fluid delivery bag at all times, and c) the constant adjustment of a roller clamp which regulates the flow to the patient. Electromechanical infusion pumps were developed to mitigate these concerns. However, the utility of such pumps was hindered by their bulky size and by their need for a constant source of electricity. These hindrances are especially troublesome in situations where a patient is at home and ambulatory, thus requiring the freedom to move about.

During the past five years, a new style of apparatus has entered the marketplace for controlled delivery of a drug which does not require the use of an electromechanical infusion pump, and thus is suited for the controlled delivery of drugs to patients who are ambulatory. This new style utilizes an inflatable latex rubber balloon housed inside a rigid, clear plastic housing. When the devices are filled with a drug, the latex balloon expands. An administration set is attached to the device and thus acts as the conduit for the drug to the patient. When the balloon is inflated by the drug, the balloon itself becomes the driving force to transfer the drug out of the reservoir to the patient via the drug administration set. Controlled release of the drug at a desired flow rate is achieved by placing an orifice of predetermined diameter in the drug line. These devices generally operated at a relatively high pressures of approximately 10 to 15 psi. Examples of the latex balloon system are disclosed in U.S. Pat. Nos. 4,769,008 and 4,915,693 and European Patent Application 0,426,319 A2.

Although the latex balloon method of drug delivery has certain advantages over the electromechanical infusion pump, the method also has its disadvantages. For example, because the balloon expands in all directions, the shape of the housing enclosing the balloon is round. This round shape does not conform well to the patient when worn in the patient's pocket. Furthermore, some of the latex balloon style devices require a special machine to fill and pressurize the balloon with a drug. Consequently, the pharmacist must use the special machine to load the device. Thus, there exists the need for a safe, economical drug delivery system which could (a) be inconspicuously and comfortably worn by the patient, (b) allow the pharmacist to fill the drug container without the use of a special pressurizing device, (c) allow the nurse or patient to load the drug container into the pressurizing device, (d) allow for reuse of parts of the system.

SUMMARY OF THE INVENTION

The present invention allows the use of standard, rectangular medication bags to be used in a platen pump. By using the standard bags, hospitals do not have to maintain a large inventory of medication bags of differing size and shape.

One aspect of the present invention is an infusion pump for expelling a fluid from a fluid reservoir. The infusion pump comprises a housing having a chamber therein for receiving a fluid reservoir and a first wall for contacting the fluid reservoir. A second wall is movable between a first position distanced from the first wall to form the chamber therebetween, and a second position relatively closer to the first wall. The second wall is moved by a parallelogram linkage. The parallelogram linkage comprises at least one spring for biasing the parallelogram linkage. The movement of the parallelogram linkage causes the second wall to advance toward the first wall. Importantly, the advancement of the second wall provides increased force on the fluid reservoir through the dispensation cycle thereby achieving a constant flow rate.

In another embodiment, an infusion pump comprises a housing having a chamber therein for receiving a fluid reservoir. The pump contains a first wall for contacting the fluid reservoir and a second wall movable between a first position distanced from the first wall to form the chamber therebetween, and a second position relatively closer to the first wall. The pump includes a compression means for moving the second wall, wherein the compression means achieves a substantially constant flow rate from the fluid reservoir by increasing the force applied to the fluid reservoir as the second wall moves toward the second position.

In a further embodiment, an infusion pump for expelling fluid from a fluid bag is provided. The fluid bag has an outlet. The infusion pump includes a generally rectangular base having a non-planar bag-engaging inner surface for supporting the fluid bag. The base has a slot around at least a portion of a periphery thereof. A generally rectangular cover cooperates with the base to define a space in which the bag may be positioned. The cover has a rim extending about at least a portion thereof for mating engagement with the slot of the base, whereby the cover may be selectively connected to the base. A generally rectangular platen is movably connected to the cover and moveable from a first distance above the inner surface of the base to a second distance nearer the inner surface of the base than the first distance. The platen has a bag-engaging surface which is non-planar and complementary to the bag-engaging inner surface of the base. The platen is connected to the cover with a linkage. A first shaft has a first end and a second end and a second shaft has a first end and a second end. A pair of slides are movably mounted along the first and second shafts. A spring is mounted between each end of the ends of the springs and the slides. The linkage comprises a parallelogram linkage formed by four arms, the arms being rotatably connected to the slides and rotatably connected to the platen and the cover. A rod engages the platen and extends through the cover for engagement with a handle, whereby rotation of the handle causes the platen to move upwardly towards the cover, thereby compressing the springs.

In another embodiment, an infusion pump for expelling fluid from a fluid bag having an outlet is provided. The infusion pump includes a generally rectangular base having a non-planar bag-engaging inner surface for supporting the fluid bag. The base also has a slot around at least a portion of a periphery thereof. A generally rectangular cover cooperates with the base to define a space in which the bag may be positioned. The cover has a rim extending about at least a portion thereof for mating engagement with the slot of the base, whereby the cover may be selectively connected to the base. A generally rectangular platen is movably connected to the cover and moveable from a first distance above the inner surface of the base to a second distance nearer the inner surface of the base than the first distance. The platen has a bag-engaging surface which is non-planar and complementary to the bag-engaging inner surface of the base. The platen is connected to the cover with a first and a second linkage. Further, a first shaft having a first end and a second end and a second shaft having a first end and a second end are provided and a first slide and a second slide movably mounted along the first and second shafts. A spring is mounted between each end of the ends of the springs and the slides. Each linkage comprises a parallelogram linkage formed by four arms. A first arm is rotatably connected to the first slide and rotatably connected to the platen. A second arm is rotatably connected to the second slide and rotatably connected to the platen. A third of the arms is rotatably connected to the first slide and the cover. A fourth arm is rotatably connected to the second slide and rotatably connected to the cover. The arms of the first and second linkages are positioned on opposite sides of the slides. A rod engages the platen and extends through the cover for engagement with a handle, whereby rotation of the handle causes the platen to move upwardly towards the cover, thereby compressing the springs.

Further features and advantages of the present invention will become apparent to one of skill in the art from a review of the Detailed Description of Preferred Embodiments which follows, when considered with the attached claims and drawings.

BRIEF DESCRIPTION OF THE DRAWINGS

FIG. 66 is a top plan view of an alternative embodiment of the fluid container shown in FIG. 61;

FIG. 67 is a left side view of the alternative embodiment shown in FIG. 66;

FIG. 68 is a front view of the alternative embodiment shown in FIG. 66;

FIG. 69 is a rear view of the alternative embodiment shown in FIG. 66;

FIG. 70 is another alternative embodiment of the fluid container shown in FIG. 61;

FIG. 71 is a left side view of the alternative embodiment shown in FIG. 70;

FIG. 72 is a front view of the alternative embodiment shown in FIG. 70;

FIG. 73 is a rear view of the alternative embodiment shown in FIG. 70;

FIG. 74 is a top plan view of another alternative embodiment of the fluid container shown in FIG. 61;

FIG. 75 is a left side view of the alternative embodiment shown in FIG. 74;

FIG. 76 is a front view of the alternative embodiment shown in FIG. 74;

FIG. 77 is a rear view of the alternative embodiment shown in FIG. 74;

FIG. 78 is a top plan view of another alternative embodiment of the fluid container shown in FIG. 61;

FIG. 79 is a left side view of the alternative embodiment shown in FIG. 78;

FIG. 80 is a front view of the alternative embodiment shown in FIG. 78;

FIG. 81 is a rear view of the alternative embodiment shown in FIG. 78;

FIG. 82 is a top plan view of another alternative embodiment of the fluid container shown in FIG. 61;

FIG. 83 is a left side view of the alternative embodiment shown in FIG. 82;

FIG. 86 is a top plan view of another alternative embodiment of the fluid container shown in FIG. 61;

FIG. 87 is a left side view of the alternative embodiment shown in FIG. 86;

DETAILED DESCRIPTION OF THE PREFERRED EMBODIMENT

Figure 1:
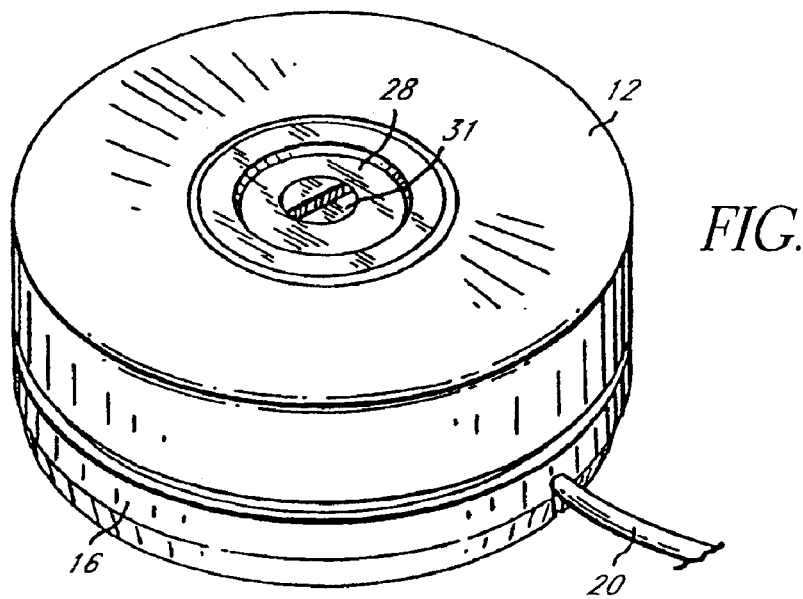
FIG. 1 is an isometric view of the infusion device of the present invention.
Figure 2:
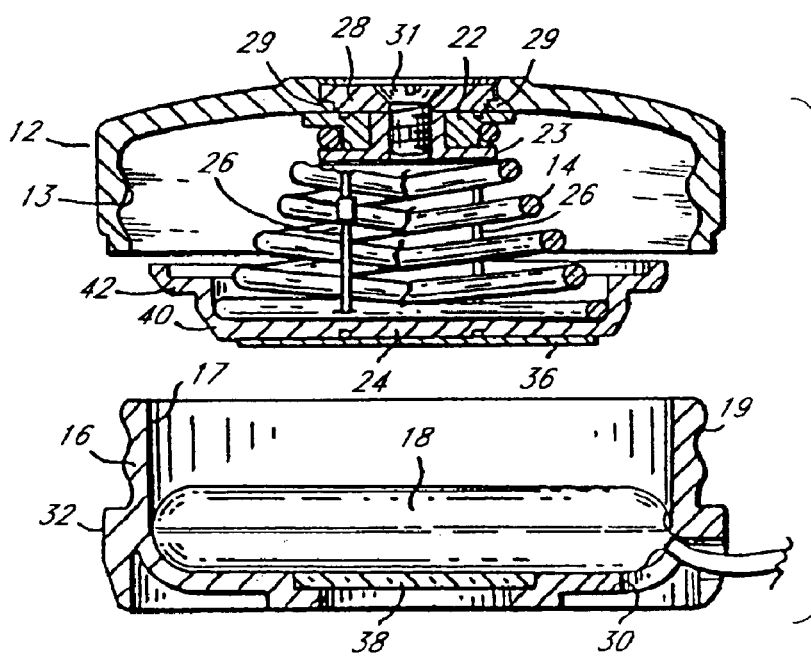
FIG. 2 is a partial cross-sectional view of the infusion device of FIG. 1 with the shells not engaged.

Referring now to the figures, the infusion device of the present invention shall be called a platen pump. The platen pump is formed in two parts, a pressurizing portion and a fluid containing portion. Each portion is housed in a container or shell. A pressurizing shell 12 includes a helical spring 14. A fluid containing shell 16 includes a chamber 17 for housing a fluid delivery bag 18. When the pressurizing shell 12 and the fluid containing shell 16 are connected to form the enclosed pump, the fluid delivery bag is pressurized by the spring 14. Fluid is thus continuously forced out of the bag 18 through an outlet tube 20 in fluid communication therewith. Controlled fluid flow is achieved with a small diameter fixed orifice 46 located at or near the end of the tube. The pump of FIG. 1 is 3½" in diameter and 1.7" high. A selectively releasable clamp 34 may be applied to the outlet tube to stop fluid flow from the pump. Releasing the clamp restores fluid flow.

In accordance with the presently preferred embodiment of the invention, the pressurizing means is a conical helical coil spring 14. The spring is formed from stainless steel or a suitable spring material. The coils of the spring are made progressively larger so that when compressed the spring coils can overlap to compress to a lower height than a conventional compression spring. When the spring is expanded it takes on a conical shape. The conical helical spring exerts the greatest force when it is fully compressed. The force is approximated by the equation $F=kx$, where k is the spring rate and x is the distance the spring is compressed. Because it is desirable to have the force exerted on the drug container be nearly the same when the container is full as when it is nearly empty, it is preferred that the free length of the spring be several times the height of the pump. Thus, the working length is but a fraction of its total free length. This insures that the force applied by the spring is kept within an acceptable tolerance from the beginning to the end of the infusion. In accordance with the presently preferred embodiment, the change in force exerted by the spring over the course of an infusion as compared to the initial force it exerts when compressed against a full fluid delivery bag is less than ±20%. In accordance with the invention, the spring length should be selected such that the change in force over the course of an infusion is less than 20%. In addition to a conventional compression spring, this concept would apply to a leaf spring, if it was used instead, where the deflection in the leaf spring is but a fraction of the total possible deflection.

Figure 4:
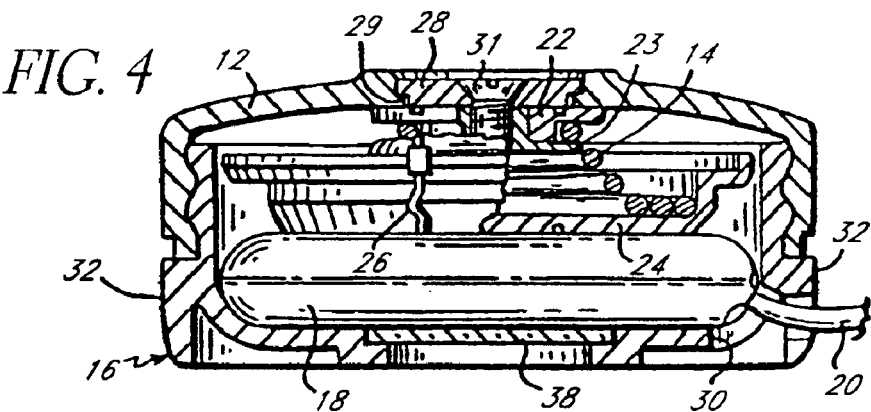
FIG. 4 is a cross-sectional view of the infusion device of FIG. 1 with the shells fully engaged.
Figure 5A:
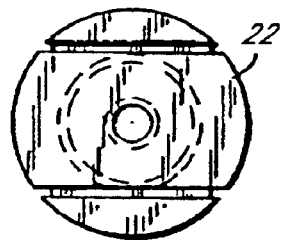
FIGS. 5a and 5b are a plan view and side view, respectively, of the rotatable spring retainer used in the infusion devices of FIG. 1.
Figure 5B:
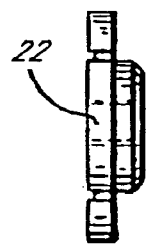
Figure 6A:
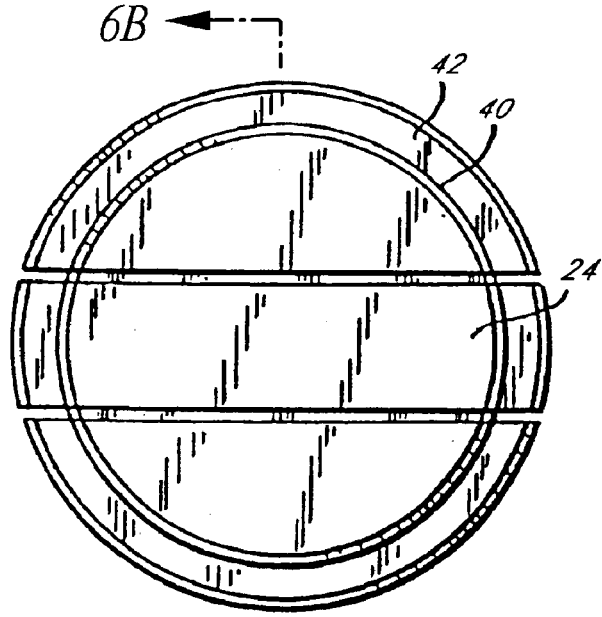
FIGS. 6a and 6b are a plan view and side view, respectively, of the platen used in the infusion device of FIG. 1.
Figure 6B:
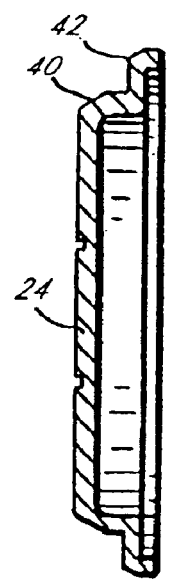

A flexible cable retainer 26 encircles the spring 14 to set its initial compressed height and also to prevent it from expanding beyond the height of the pressurizing shell 12. In the presently preferred embodiment, two cables 26 are used. Thus, the spring 14 does not bear against the fluid delivery bag when the pressurizing shell 12 is initially engaged with the fluid containing shell 16. This makes it easy for a user to bring the two shells together. With the spring in its initially compressed state, the force differential between the full position shown in FIG. 4 and empty position with the bag squeezed to a completely collapsed position is less than 20% of the initial force in the full position. While the conical helical coil spring is preferred, it would be possible to make a platen pump with a leaf spring, a pressurized bladder, a standard helical compression spring or a canister of pressurized gas to act as the pressurizing means.

The smallest coil of the spring is rotatably attached to the closed end of the pressurizing shell 12. The spring is attached to the pressurizing shell by a rotatable connector including a spring retainer 22, an anchor pivot 28, a spring stop 23 and a screw 31. The anchor pivot 28 is seated on a shoulder 29 encircling a hole in the top of the pressurizing shell 12. The anchor pivot 28 is free to rotate on the shoulder 29. The rotatable spring retainer 22 is mounted to an anchor pivot 28. The spring retainer 22 centers the spring to the shell. A spring stop 23 clamps the end coil of the spring to the spring retainer and prevents the spring from dislodging from the spring retainer 22. The screw 31 holds the anchor pivot 28 and the spring stop 23 together. The spring retainer 22 is sandwiched between the anchor pivot and the spring stop.

Preferably, in the present invention, a fluid delivery bag is pressurized to only about 5 psi which requires only about 30 pounds of force. In order that health personnel or the patient can pressurize the pump without assistance, the pressurizing shell 12 and fluid containing shell 16 are threadably engaged. In the presently preferred embodiment, the pressurizing shell has inner helical threads 13 and the fluid in containing shell has outer helical threads 19. By increasing the number of threads per inch, the axial force provided by the threads can be increased for a given torque. The presently preferred embodiment uses four (4) threads per inch so that it is relatively quick and easy to screw the shells together to fully pressurize the pump. The threads provide a mechanical advantages so that a modest amount of torque can generate sufficient amounts of axial load to compress the spring.

The platen 24 is located between the spring 14 and the fluid delivery bag 18 when the two shells are connected. The platen 24 distributes the pressure from the spring 14 over the bag. The presently preferred platen 24 is made of polycarbonate. The platen 24 has a bottom flat portion which extends over an area no greater than a substantially flat central portion of the full fluid delivery bag. This serves to keep the contacting surface areas fairly constant over the course of the entire infusion to help minimize changes in pressure on the fluid bag. The platen 24 is held against the helical coil within the pressurizing shell 12 by the flexible restraining cable 26. The cable 26 is preferably made from multi-strand stainless steel. It is looped about the rotatable retainer 22 and the platen 24. Preferably, two cable loops 26 are used. Grooves are provided in the retainer 22 and platen 24 to accommodate the cables 26. The cable 26 and platen 24 shall rotate freely about the axis of the pressurizing shell. Thus, when the pressurizing shell is rotated with respect to the fluid delivery shell to thread the two together, the pressurizing shell turns independently of the platen 24. The platen 24 should remain stationary with respect to the fluid delivery bag so that no torsional load is imparted on the bag. In order to mechanically prevent twisting the fluid delivery bag 18 when the two shells are screwed together, anti-rotation tabs can be attached to the outer edges of the platen 24. The tabs would extend out radially to engage slots in the wall of the fluid containing shell 16. The tabs would be guided in the slot, thus preventing the platen from turning with respect to the fluid containing shell. It has been found that rotatably attaching the spring and platen to the pressurizing shell is sufficient to avoid applying undesirable torque to the fluid delivery bag. The tabs and slots are not required.

Figure 3:
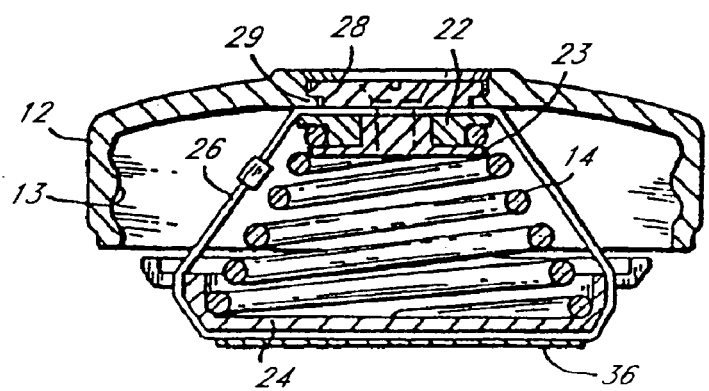
FIG. 3 is a side cross-sectional view of the top shell of FIG. 2.

Because it is desirable to have a device which allows the patient to examine the volume of fluid still retained in the fluid delivery bag so that the patient can determine when the bag is empty, preferred embodiments of the present invention utilize a clear plastic window 38 in the bottom of the fluid containing shell 16. Due to cost and safety considerations, especially preferred embodiments of the present invention use a clear plastic, such as polycarbonate, as the window material. A legend such as the word "Empty" or "E" or some other symbol is embossed on the bottom side of the platen 24. Advantageously, the legend will be fuzzy or illegible when viewed through the elastomeric disk and transparent window when there is liquid in the fluid delivery bag. When the bag has been emptied and the platen lies flat against the layers of the bag, disk and the bottom of the chamber 17, the legend on the platen 24 comes into focus through the bottom of the fluid containing shell due to the transparent nature of the fluid delivery bag and the contact clarity of the disk. This can be used to provide a clear indication of when the fluid bag is empty. It has been found that a small amount of silicone oil between the window and the disk will enhance the clarity. Alternatively, a plastic label 36 may be adhered to the bottom of the platen 24, as illustrated in FIG. 3. Desirably, when supplied, the label 36 includes the legend instead of the bottom surface of the platen 24, as described above.

To the extent possible, it is desirable to maintain a relatively constant flow rate throughout an infusion with the platen pump. In order to minimize changes in the internal pressure within the fluid delivery bag, it is important that the surface area of contact between the bag and the rigid surfaces pressing against it be kept constant. In accordance with the present invention, the bottom of the chamber 17 in the fluid containing shell 16 is contoured to evenly support the bottom of the bag over its entire area. Thus, the surface contact against the bottom of the bag remains constant during the full stroke of the platen. In the figures, a curved contour is shown about the periphery of the chamber 17. The bag 18 when filled with fluid matches this curved contour to receive support over its entire area. The contour of the chamber 17 could also be achieved with a 45° angle about the periphery. While the bag 18 might not completely fill the corner formed by the angle, the contour of the surface areas should be adequate to provide substantial support and contact with the bag's entire area.

It is also important that the contact area of the platen 24 against the bag remain constant. Therefore, the platen 24 has a bottom flat surface which does not extend beyond a flat central portion of the fluid delivery bag. If only the flat portion of the platen were to act on the bag, a residual fluid would remain in the bag about its periphery at the end of the infusion. In order to more completely deliver the fluid from the bag, the platen has a chamfered edge 40 and a recessed outer ring 42. These portions of the platen roughly match the contour of the periphery of the bottom of the chamber 17. A platen 24 with a periphery that conforms more exactly to the contour of the chamber bottom could also be used. Near the end of an infusion, as the platen 24 descends towards the chamber bottom, fluid which builds up about the periphery of the bag 18 is pushed out by the edge 40 and the recessed ring 42.

An opening 30 is provided in the fluid-containing shell through which the outlet tube connected to the fluid delivery bag 18 can be extended. An outer wall 32 of the fluid containing shell can be provided to serve as a grip. When screwing the shells together, one hand holds the outer wall of the pressurizing shell and the other hand holds the outer wall 32 of the fluid containing shell 16.

Figure 7:
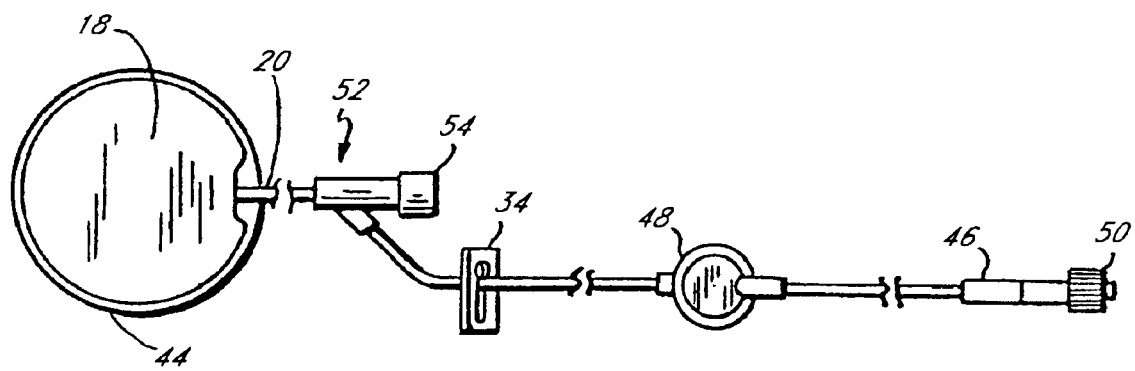
FIG. 7 is a plan view of the fluid delivery bag of the present invention.

These two shells of the pump are circular in shape to permit threadable engagement. Referring now to FIG. 7, the fluid delivery bag 18 for use in the platen pump is a circular pouch connected to an outlet tube. The circular pouch, advantageously, has no corners. Thus, the seam 44 of the bag is uniformly stressed. To assist in achieving uniformity of pressure in the bag, the periphery of the bag has a curved contour when filled. The center portion of the bag is substantially flat so that the contacting surfaces between the platen and the bag can remain relatively constant throughout an infusion. The bag is made from a suitable pliable biocompatible plastic material, such as a class VI, PVC biocompatible plastic. The bag is formed from two sheets that are RF welded together and trimmed around their circumference. The round shape of the bag achieves uniform stress on the welded seam.

The outlet tube 20 is connected to the bag 18. The tube 20 may lead to a restricted orifice 46 which restrains the flow of fluid from the delivery bag when it is pressurized. Orifices of 0.004" to 0.008" diameter are presently contemplated. In order to prevent the orifice from becoming blocked, an optional particulate filter 48 can be inserted in the outlet tube to stop the flow of particles which might occlude the orifice. The orifice provides a relatively constant fluid flow. As an alternative to the restricted orifice, a length of tubing of known diameter, e.g., an 18 inch length of 0.015" tube can be substituted. In order to facilitate filling the fluid delivery bag, a Y-injection site 52 may be inserted into the outlet tube 20. The Y-injection site 52 includes a latex rubber self-sealing septum 54 through which a needle may be inserted to inject fluid into the bag. As an alternative, a second filling port (not illustrated) may be added to the bag.

The end of the outlet tube can be connected to a luer adapter 50. The adapter is a threadably engaged connector. It is designed to mate with a threadably engaged disconnect on an IV line. In order to permit reusability of an infusion set, the outlet tube 20 of the fluid delivery bag can be directly connected to a second luer adapter 50 (not illustrated) approximately 3 inches from the drug bag. A clamp would be used on the tube between the bag and the luer adapter 50. Fluid may be injected in through the luer adapter 50 so a Y-injection site would not be needed. When the drug has been expended, a new drug bag may be attached to the IV set, thus reusing the IV set for multiple doses over a 24 to 48 hour period.

In practicing the invention, the clamp 34 is used to close the outlet tube on an empty drug delivery bag. A needle pierces the septum 54 to inject fluid into the drug delivery bag. The bag when full should have a substantially flat top and bottom central portion when resting on a flat surface. The needle is removed. The bag, with its permanently affixed IV line, is placed in the chamber 17 of fluid containing shell 16 with the IV line passing through the opening 30 in the bottom of the shell. When the upper and lower shells are brought together, the threads should preferably engage initially before the platen 24 pressurizes the bag. The two shells are then simply screwed together until a stop position is reached. At this point, the drug bag is fully pressurized. The IV output line is purged of air by opening the clamp 34 and allowing fluid to flow. Once the fluid stream ejects slightly, the tube can be reclamped. The output line is then connected to a catheter line or needle for administering an infusion to a patient. Releasing the clamp initiates fluid flow. When the legend on the platen 24 comes into focus through the window 38 in the fluid containing shell 16, the bag has been emptied. The output line is removed or disconnected from the patient. The two shells are then unscrewed and the drug container and IV line are discarded. The pump can be reused.

Figure 8:
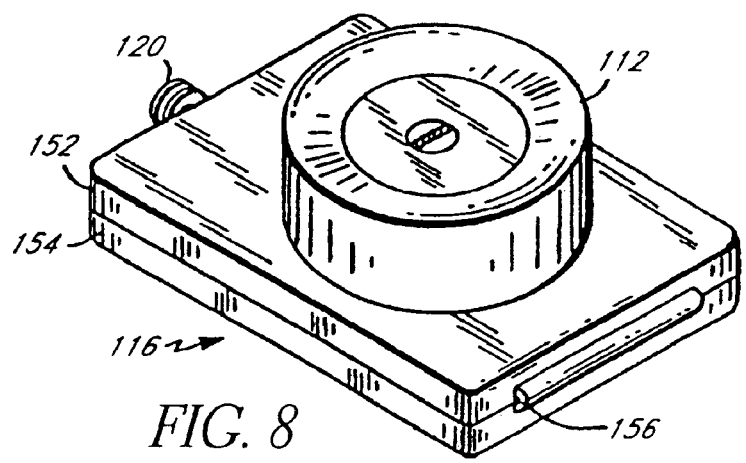
FIG. 8 is an isometric view of an alternate embodiment of the infusion device of the present invention.
Figure 8B:
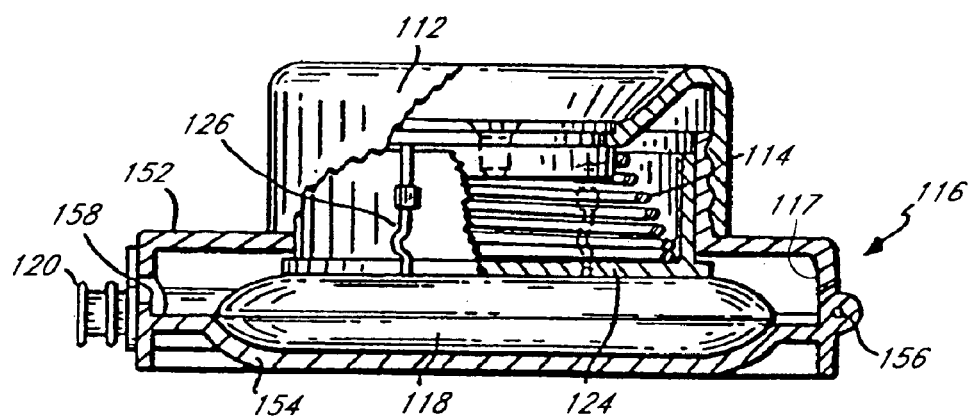
FIG. 8b is a cross-sectional view of the infusion device of FIG. 8 in a closed position.
Figure 8A:
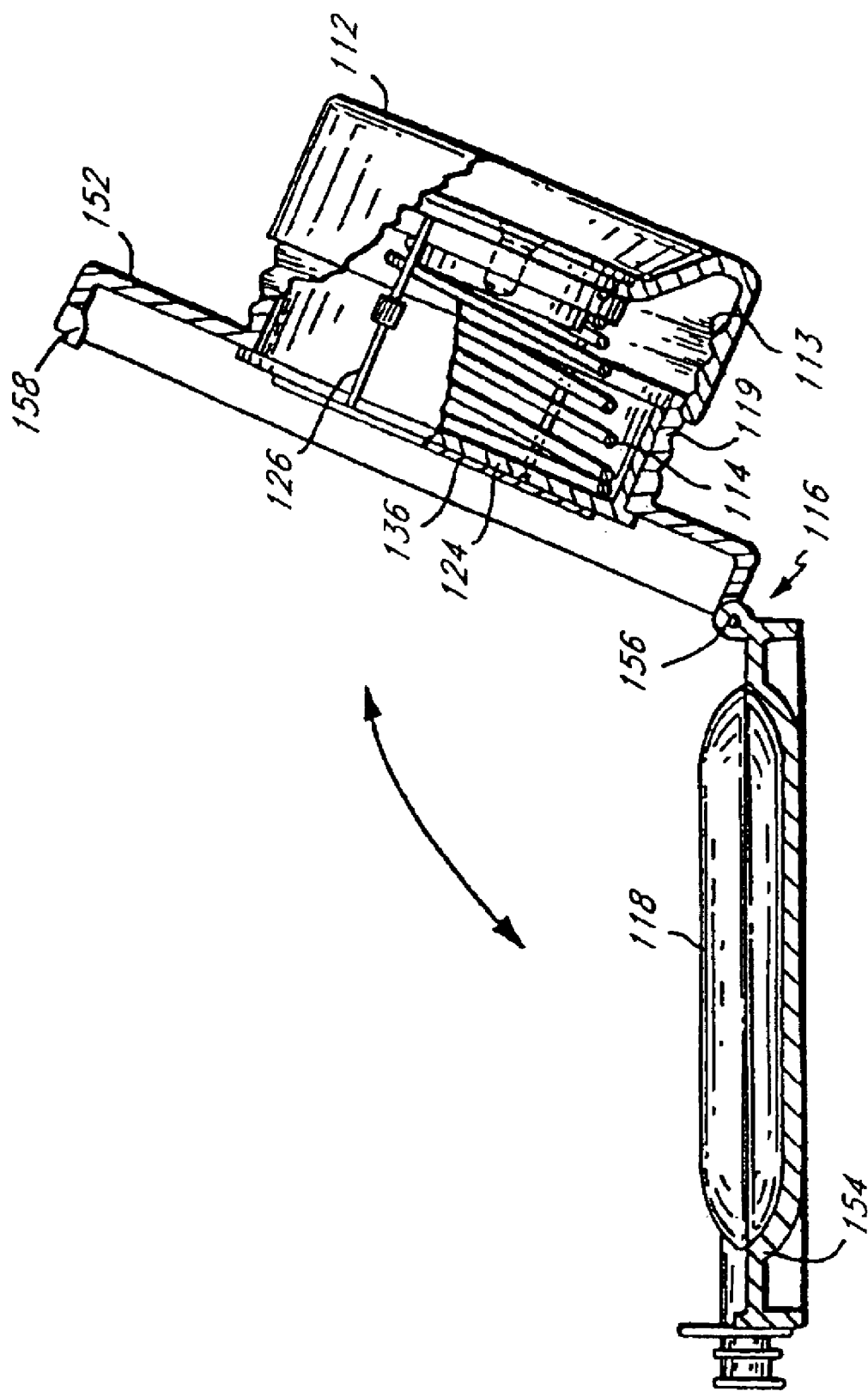
FIG. 8a is a cross-sectional view of the infusion device of FIG. 8 in an open position.

Referring now to FIGS. 8, 8a and 8b, an alternate embodiment of the present invention illustrated. The numerical labels in the drawings are 100 higher than corresponding similar elements in the first embodiment. When it is desired to use a conventional rectangular drug delivery bag 118, the alternate embodiment can be used. The fluid containing shell 116 of the alternate embodiment is provided with a rectangular chamber to accommodate the rectangular drug delivery bag. The fluid containing shell 116 is formed by an upper portion 152 and lower portion 154 attached at one end by a hinge 156. The opposite ends are connected by a latch 158 when the upper and lower portions are closed. The upper portion 152 includes a threaded cylindrical wall 119 for interfacing with the threaded wall 113 of the pressurizing shell 112. The platen 124 attached to the spring 114 of the pressurizing shell 112 is made rectangular to fit over the substantially flat center portion of the rectangular bag.

In this embodiment, the delivery bag 118 has an outlet tube with a fitting 121 thereon for coupling to a fluid line. In addition, the platen 124 has an outer diameter which is larger than the inner diameter of the pressurizing shell 112, whereby the upward travel of the platen 124 is limited. In this arrangement, the platen 124 moves from a first position in which its outer flange abuts the shell 112 (when the bag is full) and a second position nearer the lower portion 154 when fluid is expelled from the bag.

To operate the platen pump of the alternate embodiment, the pressurizing shell is unscrewed and loosened on the fluid containing shell. The fluid containing shell is opened about its hinge or sliding means. A fluid delivery bag is inserted. The fluid containing shell is closed at its latch. The pressurizing shell can then be screwed onto the fluid containing shell to pressurize the drug delivery bag.

In accordance with a further aspect of the present invention, there is provided an infusion pump having a platen which is divided into two or more segments. Preferably, each segment is provided with an independent biasing means for compressing each respective segment against the medication bag. The multi-segment pressure pad of the present invention cooperates with the changing contour of the deflating medication bag to maintain an improved relatively constant surface contact area between the platen and the bag. As has been previously discussed, the maintenance of a substantially constant surface contact area has been determined by the inventors herein to promote constant output pressure performance.

Referring to FIGS. 9–12, there is disclosed a dual concentric platen embodiment of the infusion pump in accordance with the present invention. Infusion device 160 is provided with a housing 162, comprising a cover portion 164 and a base 166. As with previous embodiments, the cover 164 and base 166 are preferably formed in accordance with conventional techniques for the production of medical device housings, such as injection molding of thermoplastic or thermoset polymers. Alternatively, any of a variety of other techniques may be utilized, including fabrication from sheet metal stock, as will be well understood by one of skill in the art.

The cover 164 and base 166 can be secured together in any of a variety of manners disclosed elsewhere herein. For example, cover 164 and base 166 can be provided with complementary surface structures such as male and female engaging threads. For this purpose, base 166 is provided with an annular, axially extending wall 170 to provide an extended surface contact area between the base 166 and cover 164. Alternatively, the contacting surfaces of the cover 164 and base 166 are provided with complimentary pins and J- or L-shaped grooves to permit a press-and-twist fit interlock. Any of a variety of alternative interlocking structures may be utilized with the multiple segment platen embodiment of the invention.

Depending upon the type of spring retraction structure utilized, the base 166 and cover 164 may or may not need to be removably connected. For example, in a side loading embodiment, base 166 and cover 164 may be integrally formed or permanently secured together during the manufacturing process. In this embodiment, an opening is provided in the side wall to permit introduction of a medication bag between the retracted platen and base as will be discussed.

In general, base 166, annular wall 170 and cover 164 cooperate to form a chamber 172 for containing the functional components of the infusion device 160. In the illustrated embodiment, a first platen segment 176 is biased against a medication bag 174 by means of a coil spring 178. Platen segment 176 is provided with an axially extending spring guide 184, which may comprise an axially extending annular wall or a plurality of axially extending projections. Spring guide 184 assists in maintaining the axial alignment of the spring 178 during repeated tensioning and discharge cycles of the infusion device 160. The spring guide 184 may alternatively be positioned on the radially interior side of spring 178, as well as on the radial exterior or radial interior side of the spring but depending from cap 164, as will be apparent to one of skill in the art.

The first platen segment 176 is provided with a radially outwardly extending annular flange 186 for cooperating with a radially inwardly directed stop 188 on second platen segment 180. Stop 188 is axially spaced apart from the plane of second platen segment 180 by a support 190, as will be discussed.

Second platen segment 180 comprises an annular ring positioned concentrically about the first platen 176. Second platen 180 is independently axially movable with respect to first platen 176, and moveable from a first position spaced apart from the plane of first platen segment 176 to a second position substantially in the plane of first platen segment 176. Preferably, second platen segment 180 is biased in the direction of medication bag 174 by a second spring 182.

Although first spring 178 and second spring 182 are illustrated as substantially cylindrical in configuration, a conically shaped spring is also desirable for the reasons previously discussed. In addition, alternative biasing means such as leaf springs, pressurized bladders, canisters of pressurized gas or the like may also be adapted for use in accordance with the multi-segment platen embodiment of the present invention.

Figure 9:
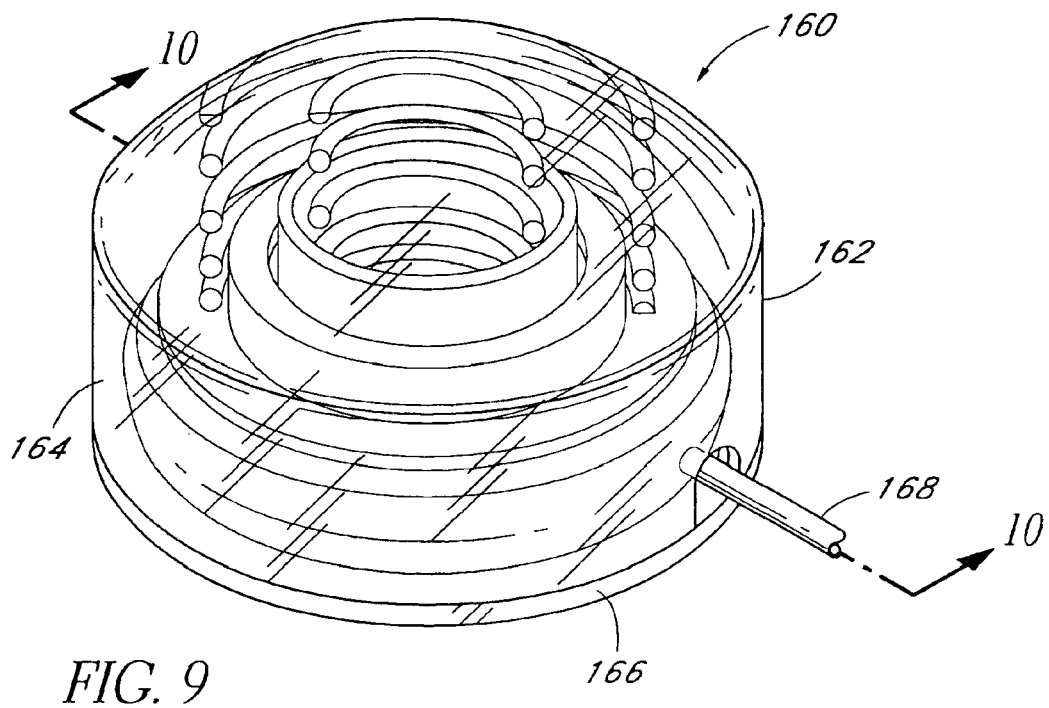
FIG. 9 is a top perspective view of a dual concentric platen embodiment of the infusion pump in accordance with the present invention.
Figure 10:
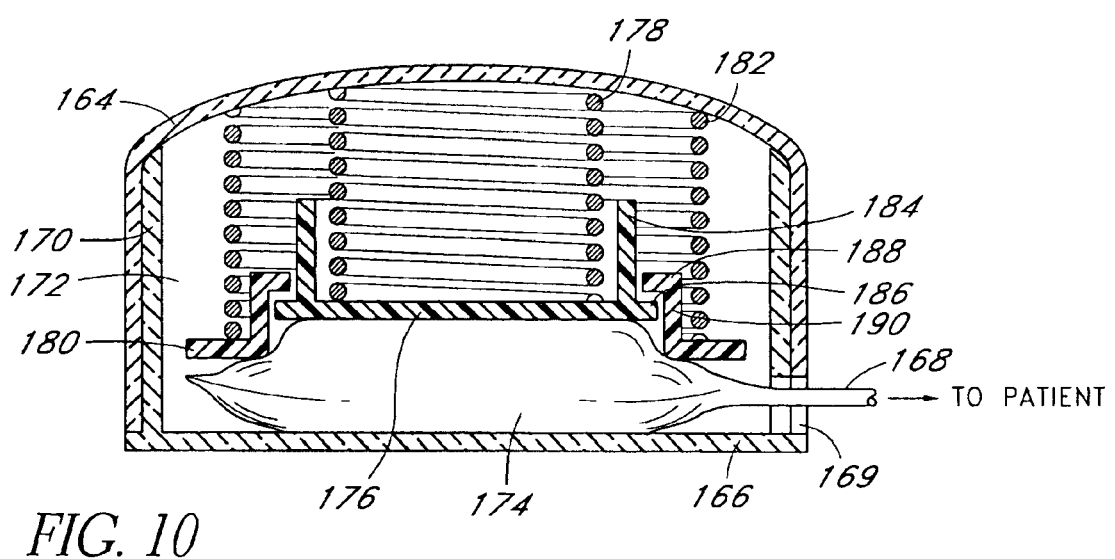
FIG. 10 is an elevational cross-sectional view of the pump illustrated in FIG. 9.
Figure 11:
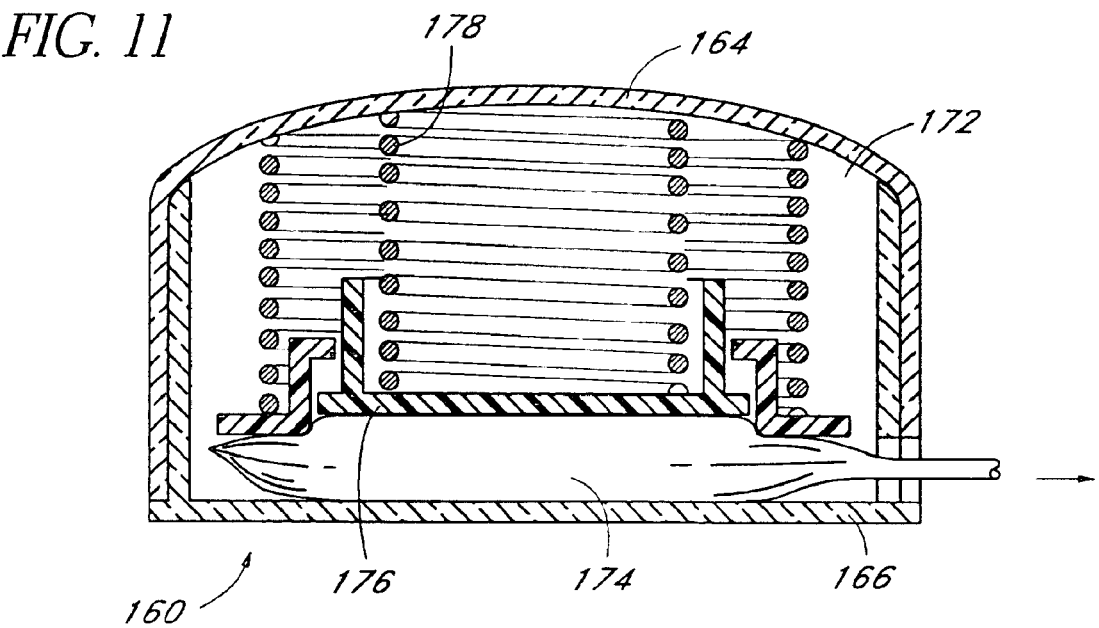
FIG. 11 is an elevational cross-sectional view of the pump illustrated in FIG. 9, partway through the dispensation cycle.

The illustrations contained in FIGS. 9–11 are simplified somewhat to highlight the multiple platen aspect of the invention. However, a variety of additional features will generally be incorporated into a finished device. For example, a spring or platen retraction structure for retracting the platen and limiting the distention of the spring in the absence of a base 166 or fluid bag 174 is also typically used. A variety of suitable retention structures are disclosed elsewhere herein, or will be immediately apparent to one of skill in the art in view of the present disclosure. In a side loading-type embodiment, a spring retraction structure is particularly desirable.

Fluid bag 174 is in fluid communication with the patient by way of effluent fluid line 168. Fluid line 168 extends through the housing 162 by way of a port 169. Modification of the port 169 to accommodate the various relationships between the cover 164 and base 166 will be apparent to one of skill in the art. Alternatively, in a side loading embodiment of the multiple segment platen pump, the port 169 is preferably configured in the form of a circumferentially extending slot having a wide enough opening in the circumferential and axial directions to accept the appropriately sized fluid bag 174.

In general, the fluid bag diameters contemplated for use in accordance with the present invention are in the area of from about 3.5 inches in diameter to about 5 inches in diameter, and from about 0.5 inches to about 1.0 inches thick. However, infusion pumps adapted to receive other sized bags can be readily produced in accordance with the disclosure herein.

FIG. 10 illustrates the configuration of the pump with a relatively full medication bag 174. Second platen 180 compresses the radially exterior-most portion of bag 174 independently of the first platen 176, which provides pressure against the central portion of bag 174. It has been determined that the provision of this bifurcated biasing allows a surprisingly more constant pressure output profile compared to the use of a planar single flat platen design.

Figure 12:
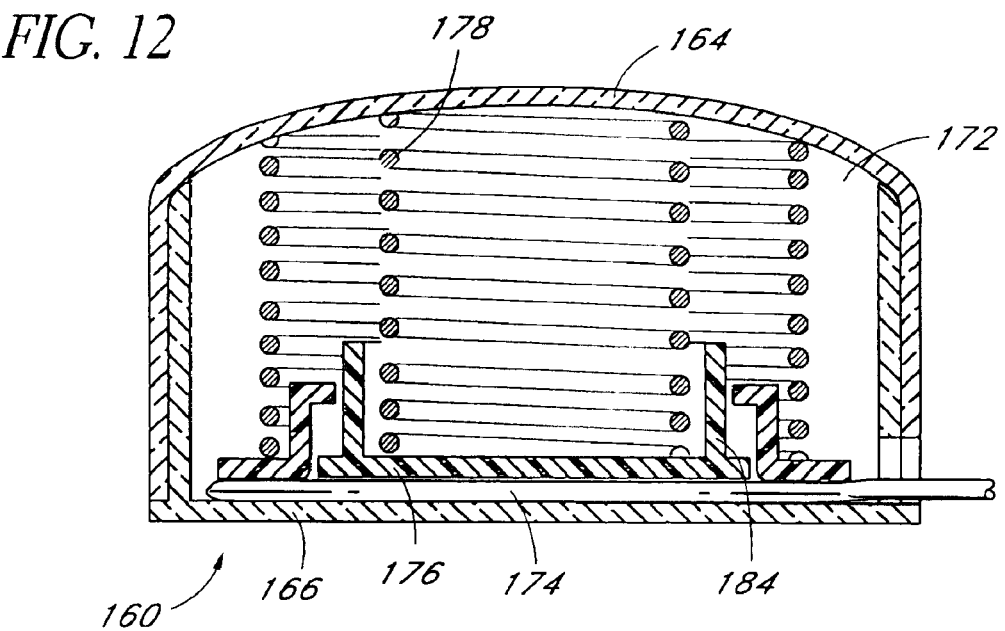
FIG. 12 is an elevational cross-sectional view of the pump illustrated in FIG. 9, at the completion of the dispensation cycle.

FIG. 11 illustrates the configuration of the device when the medication bag 174 is approximately one-half empty, and FIG. 12 illustrates the device when the fluid medication bag 174 has been substantially completely emptied.

In a dual segment platen embodiment designed for use with a 3.5-inch diameter, ½ inch thick 50 cc medication bag 174, the first platen 176 has a circular contact surface having a diameter within the range of from about 2.2 to about 2.8 inches. The bag contact surface on second platen 180 is in the form of an annular ring, with the width of the ring at any one point being within the range of from about 0.4 to about 0.7 inches. The overall outside diameter across the entire second platen 180 is approximately equal to the exterior diameter of the bag.

The relative extent to which the second platen 180 can travel distally along its path of travel with respect to the first platen 176 is limited by the axial height of the support 190. In an embodiment having a bag which is approximately one-half inch thick when full, the length of the support 190 is about 0.4 inches.

Figure 13:
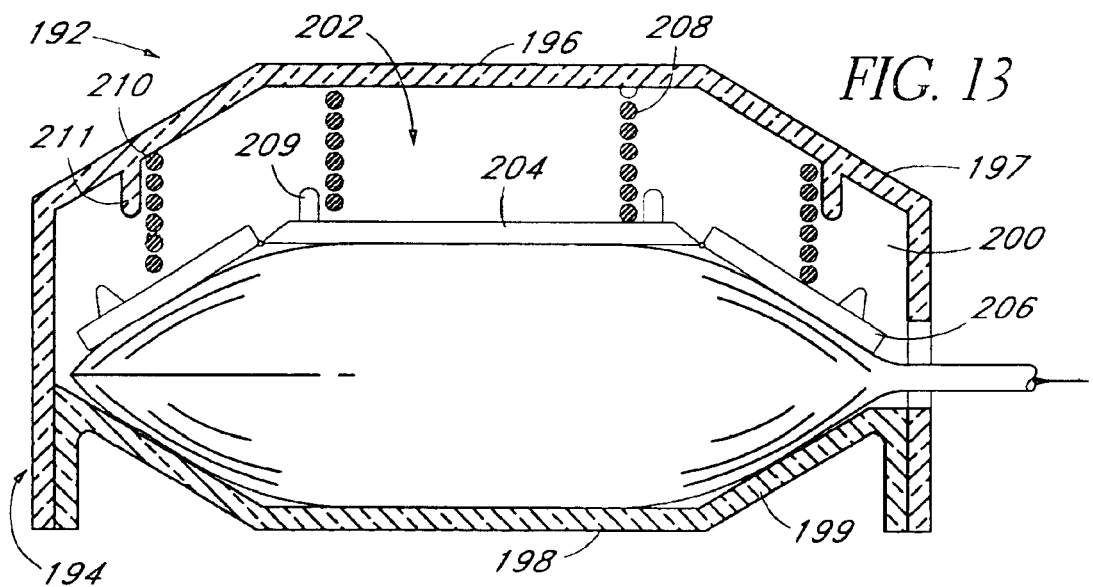
FIG. 13 is an elevational cross-sectional view of a multi-segment platen embodiment in accordance with the present invention, at the commencement of the dispensation cycle.

In accordance with a further aspect of the present invention, there is disclosed an alternate multi-segment platen embodiment at FIGS. 13–17. Referring to FIG. 13, infusion pump 192 comprises a housing 194 having an upper wall 196 and lower wall 198. Upper wall 196 and lower wall 198 may be rigidly secured with respect to one another, or removably secured with respect to one another such as by threadable engagement or other previously disclosed means.

Figure 14:
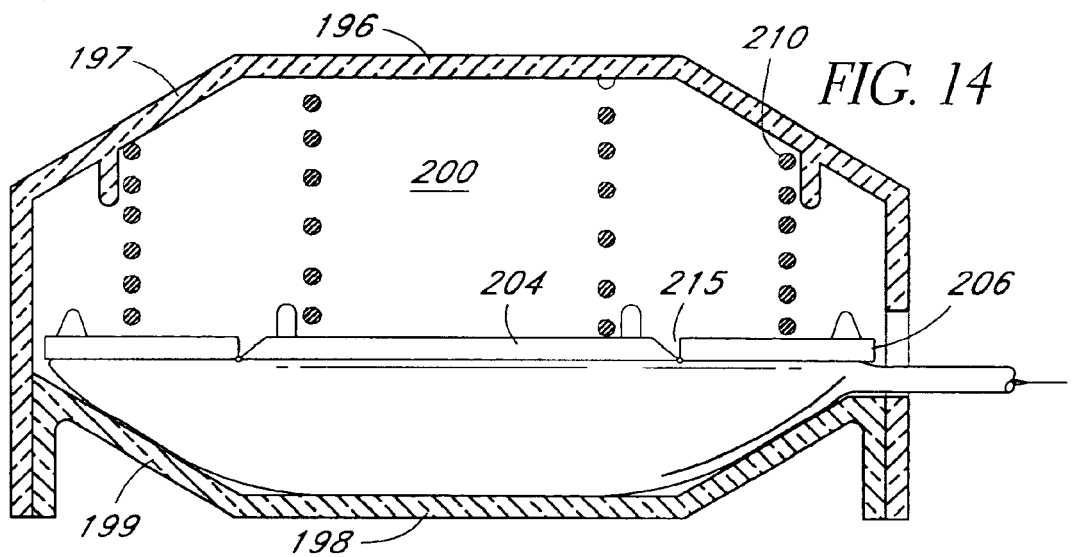
FIG. 14 is a cross-sectional elevational view of the pump of FIG. 13, partway through the dispensation cycle.
Figure 15:
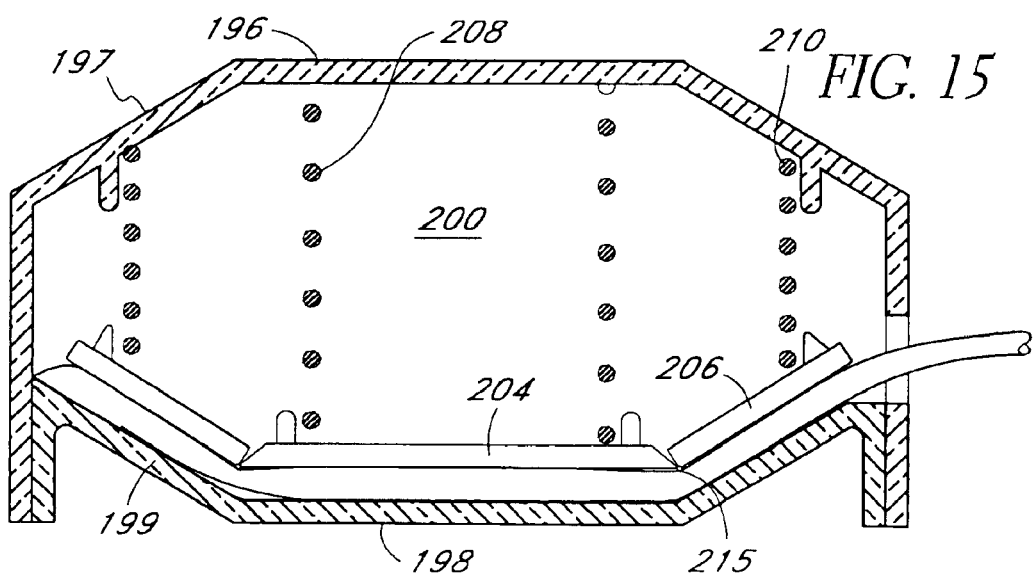
FIG. 15 is a cross-sectional elevational view of the pump illustrated in FIG. 13, at the completion of the dispensation cycle.

Upper wall 196 can be substantially planar throughout the width of the pump 192, or, as illustrated in FIGS. 13–15, can have a substantially planar central region and a sloped annular region 197. Sloped region 197 is provided on the interior surface with a peripheral spring guide 211, which is preferably an integrally molded annular ring.

Figure 16:
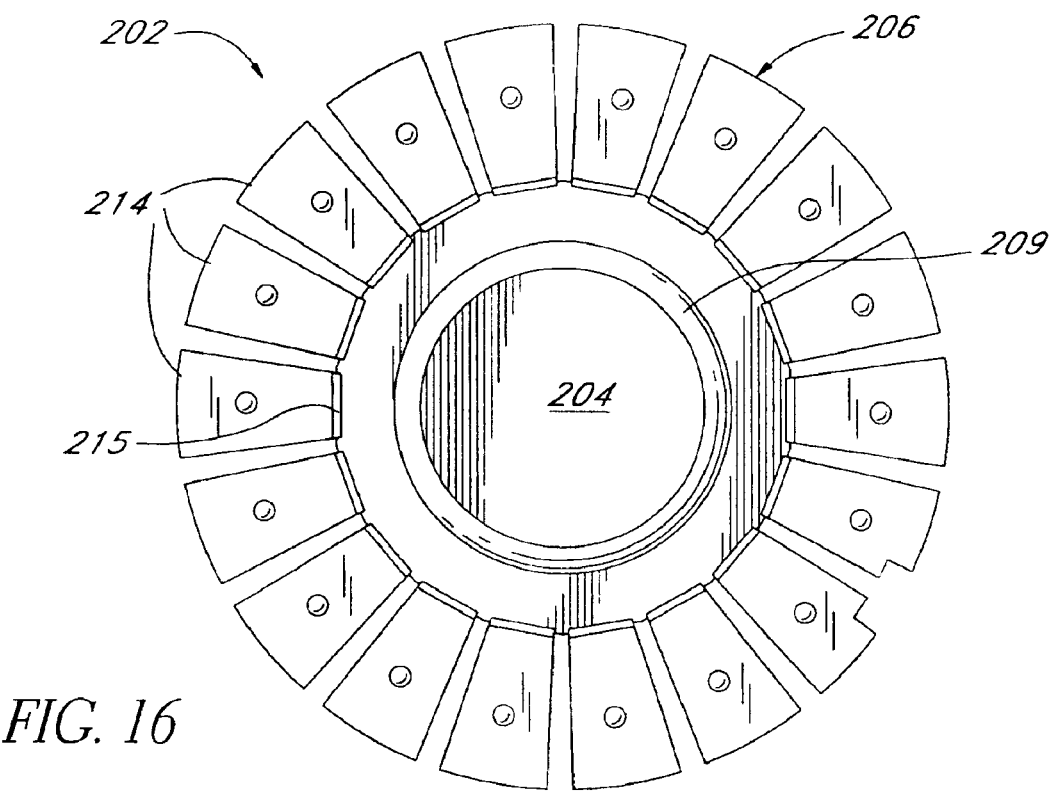
FIG. 16 is a top plan view of a multi-segment platen in accordance with one aspect of the invention.

A chamber 200 is formed between upper wall 196 and lower wall 198 to receive the functional components of the infusion pump 192. A platen 202 is movably disposed between upper wall 196 and lower wall 198. Platen 202 comprises a central region 204 and a peripheral region 206. Referring to FIG. 16, a multi-segment peripheral region 206 is illustrated.

Central region 204 is biased in the direction of lower wall 198 by at least one central spring 208. Central spring 208 is preferably maintained in position with the assistance of central spring guide 209, which may comprise a plurality of axially extending projections or an annular ring. Alternatively, spring 208 can seat within an annular recess disposed on the spring side of central region 204 of platen 202.

The peripheral region 206 is biased in the direction of lower wall 198 by one or more peripheral springs 210. Although each of the peripheral segments 214 can be provided with independent biasing means, a single annular peripheral spring 210 has been determined to perform satisfactorily in embodiments of the present invention.

An approximation of the deflation cycle is illustrated in FIGS. 13–15. At the completion of the infusion cycle, the platen 202 is biased against the lower wall 198 to substantially completely expel all of the contents of the fluid bag. In this embodiment, the lower wall 198 is provided with an axially upwardly inclined peripheral zone 199, which is dimensioned to be complementary with the peripheral region 206 on platen 202.

Referring to FIG. 16, each of the peripheral segments 214 on platen 202 is connected to the central region 204 by way of a hinge 215. Hinge 215 can be provided in any of a variety of ways, and still accomplish the objectives of the present invention. For example, the entire platen 202 can be formed from a sheet of material having sufficient flexibility that the biasing forces due to central spring 208 and peripheral spring 210 will deform the platen, as illustrated in FIG. 14. Preferably, however, the hinge 215 comprises a relatively more flexible zone than the surrounding material of platen 202. This may be provided, for example, by reducing the thickness of the platen material in the region of each hinge 215, as illustrated, for example, in FIGS. 13–15. Alternatively, the central zone 204 can be formed separately from the peripheral segments 214, and assembled thereafter such as by mounting the central zone 204 and peripheral segments 214 on a flexible sheet of material. reduced thicknesses can be produced by injection molding of the platen. Any of a variety of stamping and/or milling or grinding techniques may also be utilized to produce an annular groove in the material of an integrally formed platen 202.

Figure 17:
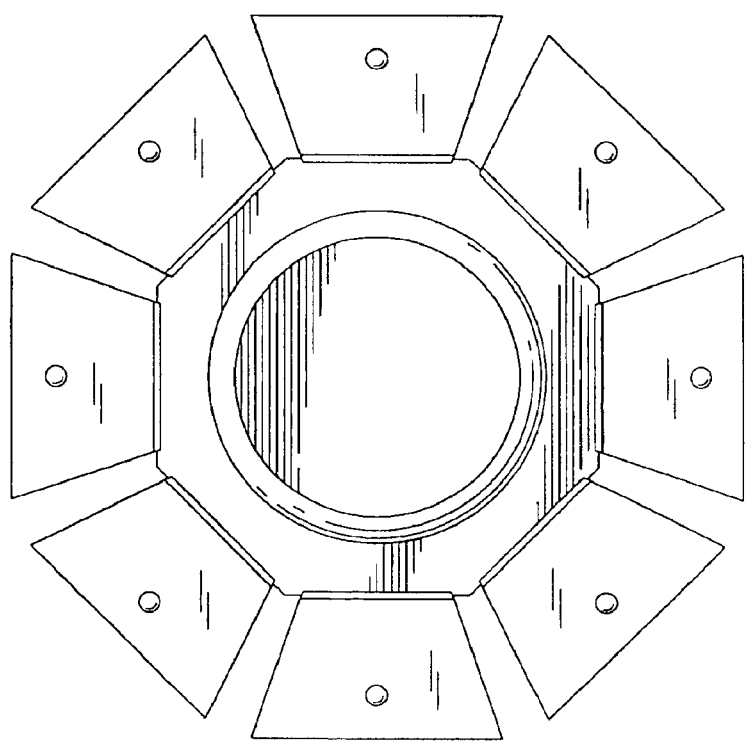
FIG. 17 is a top plan view of an alternate multi-segment platen.

Referring to FIG. 17, there is disclosed an alternate embodiment of the platen 202, particularly adapted for an infusion pump designed for use in an octagonal housing.

Spring rates and lengths may be selected to complement the respective surface areas of the central and peripheral zones to achieve the most acceptable internal bag pressure.

Figure 18:
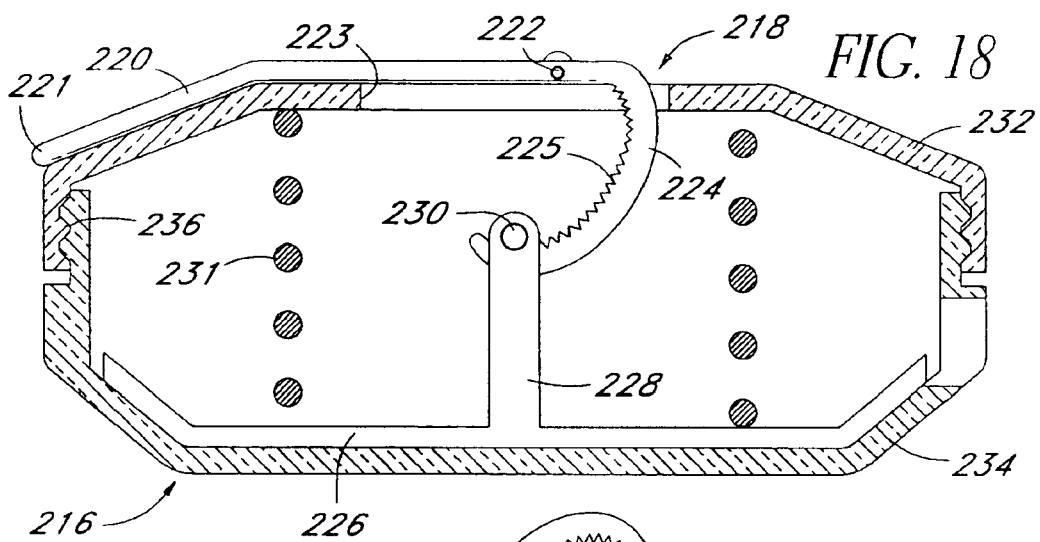
FIG. 18 is an elevational cross-sectional view of a lever assisted spring retractor in accordance with the present invention.
Figure 19:
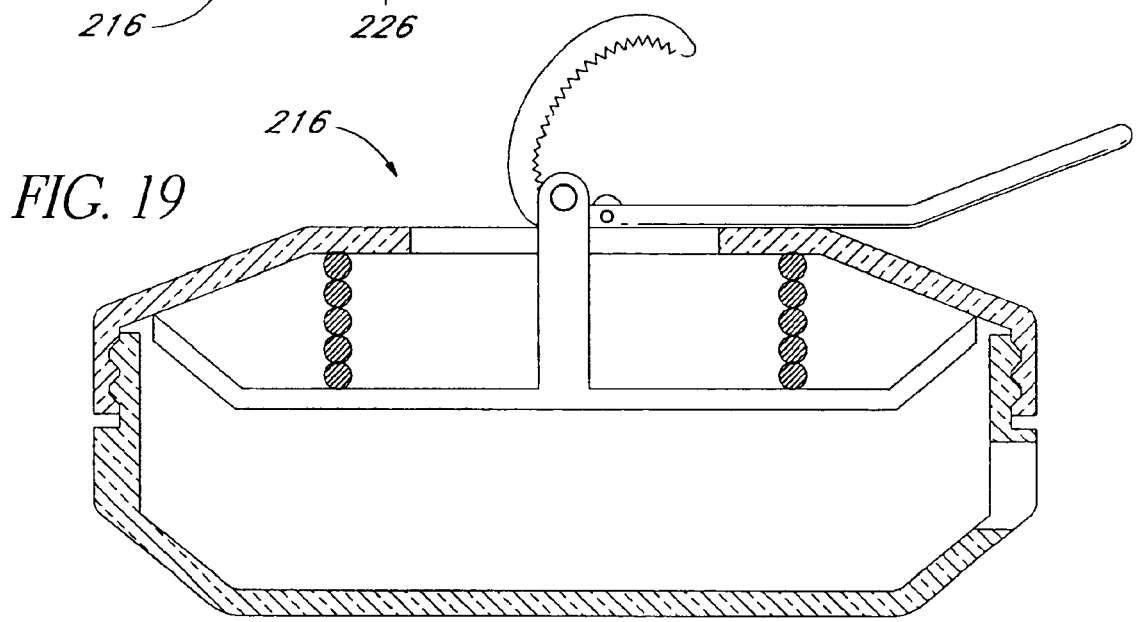
FIG. 19 is an elevational cross-sectional view of the embodiment of FIG. 18, with the platen in the retracted position.
Figure 20:
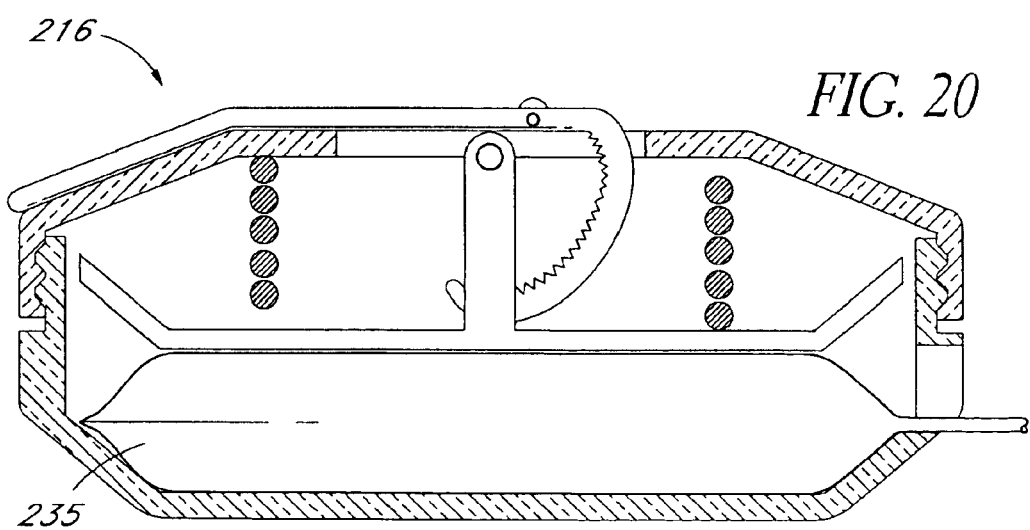
FIG. 20 is an elevational cross-sectional view of the embodiment of FIG. 18, at the commencement of the dispensation cycle.

Referring to FIGS. 18–20, there is disclosed a leverage assisted spring retractor for loading an infusion pump 216 in accordance with the present invention. The spring retractor is conveniently operated by a patient actuated lever, to retract the platen against the spring bias into the "ready" position. The fluid medication bag may thereafter be easily inserted either through a side opening on the device or by removing the bottom shell.

Referring to FIG. 18, infusion pump 216 is provided with a spring retractor 218. Spring retractor 218 is operated by lifting a patient actuated lever 220, which rotates about a fulcrum 222 on the housing of the infusion pump 216. The lever 220 extends through an opening 223 into the upper housing 232, and is thereafter provided with a ramp 224 such as a cam or other structure having a surface for slidably engaging a pin 230. The pin engaging surface of ramp 224 is preferably provided with friction enhancing surface structures such as a plurality of teeth 225. In this manner, the lever can be released by the patient at any point throughout its range of travel, and the teeth 225, pin 230 and curvature of ramp 224 cooperate to retain the partially retracted lever in position.

Pin 230 is connected to a support 228 for transferring force to the platen 226. Although illustrated as a unitary platen 226, the spring retractor in accordance with this aspect of the present invention can be readily utilized with the dual platen embodiment which has previously been disclosed.

To facilitate lifting of the lever 220, the lever 220 extends slightly beyond the outer periphery of the housing 232 to provide a tab 221. Alternatively, any of a wide variety of friction enhancing or gripping surface structures can be provided, as will be apparent to one of skill in the art.

In addition, the cam configuration is preferably such that the lever 220 has a minor amount of free play before the friction enhancing structures 225 engage the pin 230. In this manner, the lever 220 can be readily lifted slightly away from the upper housing 232 so that the patient can easily position fingers underneath the lever 220 before retracting the lever against the resistance provided by spring 231.

The spring retractor 218, in accordance with the present invention, can be utilized with any of a variety of housing structures. For example, in the embodiment illustrated in FIGS. 18–20, the housing comprises an upper housing 232 removably secured to a lower housing 234 by way of a plurality of threads 236. When the lower housing 234 is threadably removed from the upper housing 232, the combination of the ramp 224, pin 230, support 228 and platen 226 operate to limit the expansion of the spring to retain the desired prestressing. Thus, the housing can be disassembled with the platen either in the extended or retracted positions, and a fluid medication bag 235 can be placed within the lower housing 234.

Since reassembly of the lower housing 234 with upper housing 232 is not opposed by any force from the spring 231, any of a wide variety of securing means can be utilized in place of the illustrated threads 236. For example, snap fit structures, hinge and latch arrangements, and the like can be readily adapted for use. Alternatively, side installation embodiments are also contemplated by the present inventors. For example, the upper housing 232 and lower housing 234 can be integrally molded, or can be secured together in a permanent fashion following installation of the functional components. A port (not illustrated) on the side of the housing is then appropriately sized to receive a fluid medication bag 235 therethrough.

The embodiment illustrated in FIGS. 18–20 provides a uniquely low profile infusion pump 216, which may be readily loaded by the patient without the use of any additional tools, and which has a thickness of only slightly greater than the sum of the inflated medication bag and the length of the collapsed spring.

Figure 21:
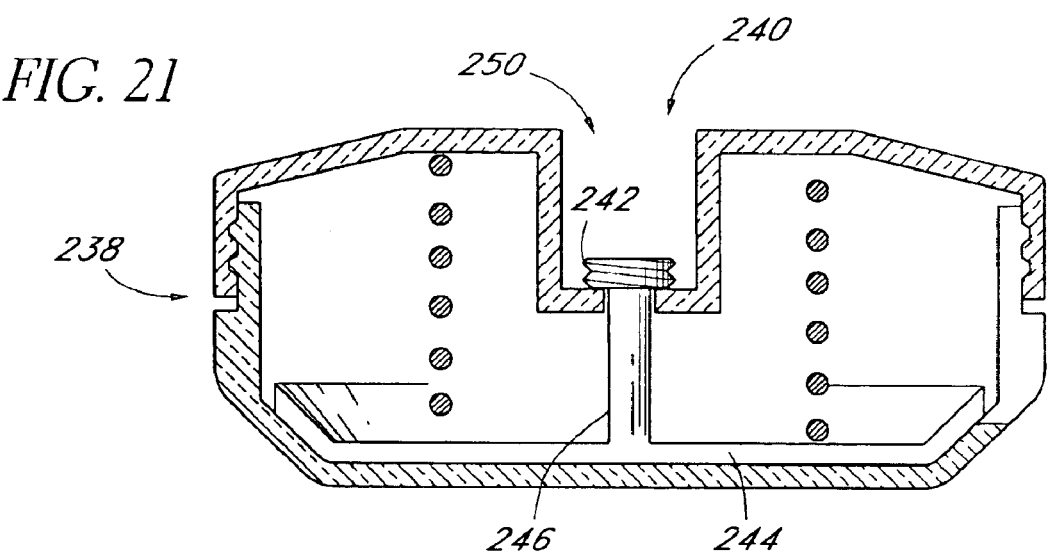
FIG. 21 is an elevational cross-sectional view of a key-operated platen retractor in accordance with the present invention.

FIGS. 21–24 illustrate a key operated platen retractor in accordance with a further aspect of the present invention. Referring to FIG. 21, there is disclosed an infusion pump 238 having a key operated platen retractor 240 thereon. Platen retractor 240 comprises a threaded member 242 such as a disk, which is connected to the platen 244 by way of a spacer 246. As will be appreciated by one of skill in the art, the threaded element 242 may comprise either a disk having an external thread on the circumferential surface thereof, or an aperture bored axially through spacer 246 and provided with a female thread for receiving a threaded key.

Figure 22:
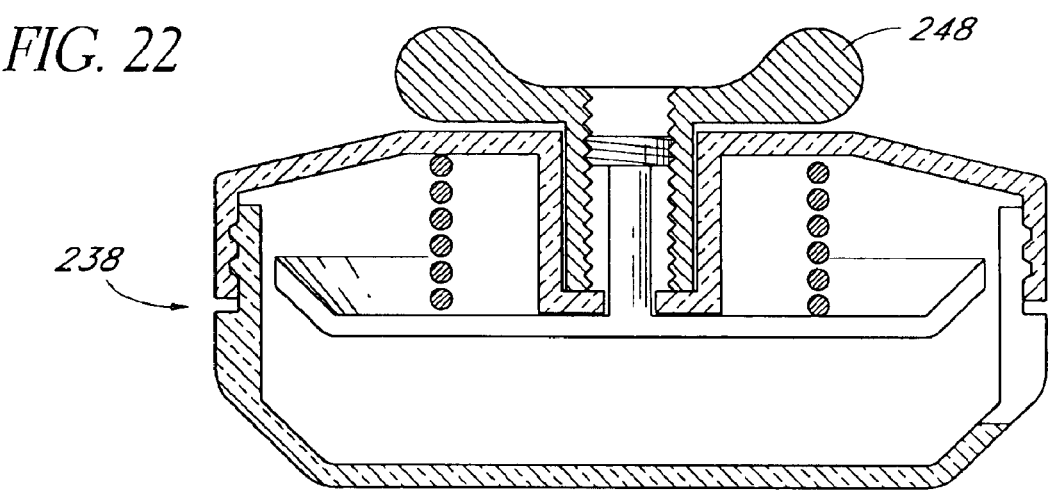
FIG. 22 is an elevational cross-sectional view of the embodiment of FIG. 21, with a key in place.

Referring to FIG. 22, a key 248 is provided for threadably engaging the threaded disk 242. Key 248 is provided with an aperture extending therethrough, and having a female thread thereon.

Threaded disk 242 operates as a stop by abutting against a portion of the housing, thereby limiting axial expansion of the spring. In this manner, the spring can be prestressed as desired.

Figure 23:
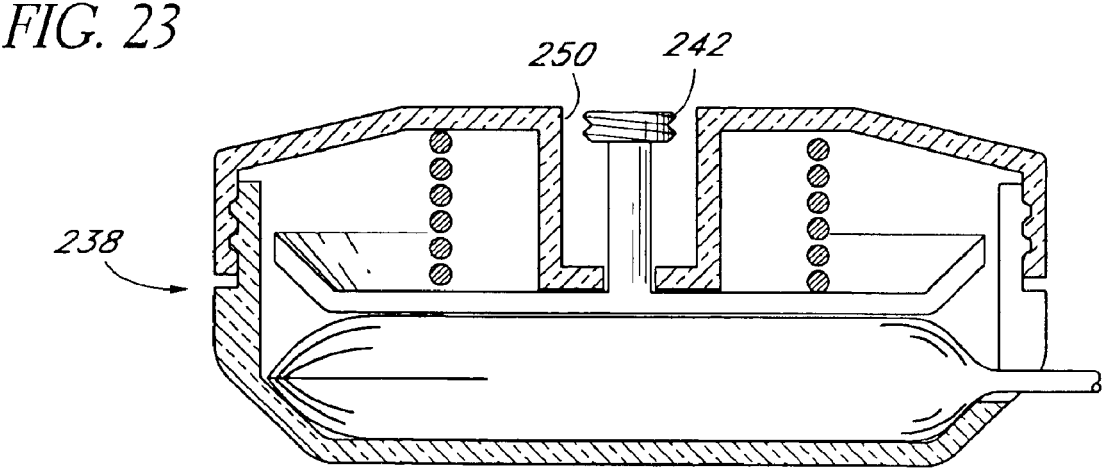
FIG. 23 is an elevational cross-sectional view of the embodiment in FIG. 21, at the commencement of the dispensation cycle.

Preferably, the threaded disk 242 is axially movably positioned within a well 250. Well 250 serves multiple functions, including permitting the loaded infusion pump 238 to retain the same exterior profile as the discharged infusion pump 238, as illustrated in FIGS. 23 and 21, respectively. In addition, the lower limit of the well 250 operates as a stop to prevent further expansion of the spring. Additionally, threaded disk 242 can serve as a liquid level indicator.

In use, the user inserts the key 248 into the well 250, and rotates the key to engage the threads on disk 242. Continued rotation of the key draws the disk axially against the bias provided by the spring, until the platen is in the fully retracted state. When fully retracted, the platen abuts the lower wall of the recess 250, as illustrated in FIG. 22. At this point, the lower portion of the housing can either be removed for installation of a fluid medication bag, or the fluid medication bag can be installed through a lateral or side entry port. It is therefore preferable that the distance between the platen when fully retracted and the bottom of the housing be slightly greater than the thickness of the filled medication bag, so that the bag may be conveniently slidably positioned therebetween.

Once the bag is in position, the user simply reverses the direction of rotation of the key, and spins the key to remove it from the threaded disk 242. Once the key is partially backed off of the threaded disk 242, the medication bag will be under pressure exerted from the platen 244.

Figure 24:
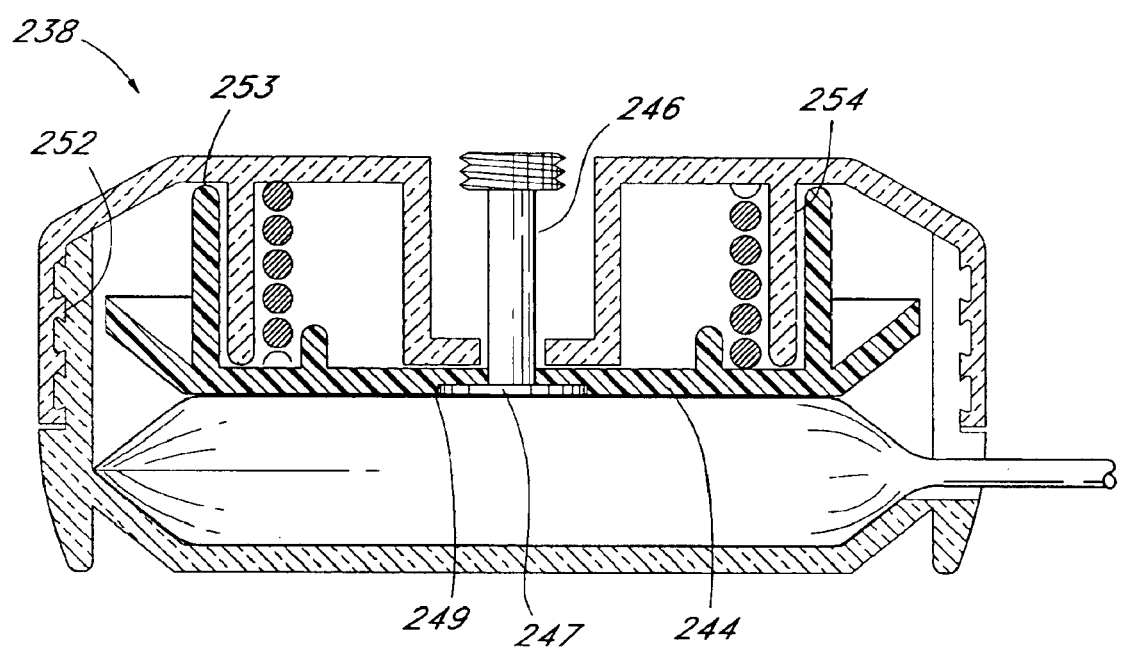
FIG. 24 is an alternate embodiment of the design illustrated in FIG. 23.

Referring to FIG. 24, there is disclosed a loaded and pressurized fluid medication delivery pump 238, similar to that illustrated in FIGS. 21–23, and including some additional details. For example, the cross-sectional view of the threads 252 reveals that the thread has a width which changes from a relatively narrow dimension at the point of attachment of the thread to the corresponding support structure, to a relatively wide width at the free end of the thread. Similarly, the channel for receiving each thread is provided with side walls which taper towards each other in a direction extending away from the bottom of the channel. In this manner, the threads are provided with a full or partial interlocking fit, which will permit the use of thinner, more flexible construction materials for the side walls of the housing, while minimizing the risk that plastic deformation of the side walls under bias from the spring will cause the threaded side walls to disengage from each other.

In addition, an annular platen guide 253 is provided to optimize the precision of the axial travel of the platen 244 throughout the dispensation and reloading cycles. Platen guide 253 cooperates with an annular spring guide 254. Platen guide 253 and spring guide 254 in one preferred embodiment comprise concentric annular flanges which are axially movable towards and apart from each other in a telescoping fashion.

An alternate means for connecting the spacer 246 to the platen 244 is also disclosed in FIG. 24. Although the spacer 246 may be integrally molded or otherwise formed with the platen 244, the spacer 246 may, for manufacturing reasons, preferably be separately manufactured and later connected to the platen 244. This may be convenient from a manufacturing standpoint or because of the desirability to utilize different construction materials for the platen and the spacer 246.

For example, referring to FIG. 24, the spacer 246 extends through an aperture in the platen 244. A shallow recess 249 is provided on the medication bag side of the platen 244, and preferably is radially symmetrically disposed about the axis of the spacer 246. Recess 249 receives an anchor 247 on the end of spacer 246. Anchor 247 may be an integrally formed disk or sheet on the end of spacer 246. Alternatively, anchor 247 is secured to spacer 246 in a post-forming operation, such as by spot welding, solvent bonding, thermal bonding, or attachment by screws or other fastening means.

In a preferred embodiment, the threaded disk 242, spacer 246 and anchor 247 are all manufactured from a suitable non-corrosive metal such as stainless steel to minimize the occurrence of stress fatigue following repeated usage of the infusion pump 238. As illustrated in FIG. 24, anchor 247 is preferably seated within recess 249 in such a manner that a smooth exterior surface is provided for compressing the fluid medication bag.

The overall thickness of the infusion pump 238 can be reduced by incorporating a collapsible platen retractor and restrainer. For example, referring to FIGS. 25 and 26, there is disclosed an infusion pump 256 having a collapsible platen retractor 258. Collapsible retractor 258 generally comprises a first segment 260 which is axially movably disposed with respect to a second segment 262. The first segment 260 and second segment 262 are assembled in such a manner that they operate to limit the distal travel of the platen as illustrated in FIG. 26. In this manner, the base of the infusion pump can be removed, and a medication bag inserted therein, while the collapsible platen retractor 258 retains a prestress on the spring.

In the illustrated embodiment, first segment 260 is conveniently provided in the form of a tubular body 261 having a longitudinal axis which extends at a perpendicular to the plane of platen 268. The tubular body 261 of first segment 260 may be integrally molded with the platen 268, or secured thereto using conventional techniques sufficient to withstand the forces generated by the spring for any given embodiment. The proximal end of the tubular body 261 of first segment 260 is provided in the illustrated embodiment with a radially inwardly directed flange 263 which operates as a limit on travel with respect to second segment 262, as will be discussed.

Second segment 262 in the illustrated embodiment comprises an elongate body portion 264 having a first end 265 and a second end 266. Preferably, first end 265 comprises a transverse element, such as a disk, extending generally in a plane which is transverse to the longitudinal axis of body 264, and adapted for reciprocal axial motion within a recess 267 provided on the housing of infusion pump 256. The recess 267 terminates in a stop such as a radially inwardly directed annular flange 269 for limiting travel of the disk shaped first end 265. See FIG. 26.

Similarly, the second end 266 of body 264 is provided with an enlargement for cooperating with the flange 263 on tubular body 261 to limit the extension of the platen 268. Thus, second end 266 preferably comprises one or more barbs having a ramped distal surface, and a proximally facing shoulder to cooperate with flange 263 as is illustrated in FIG. 26. In this embodiment, second end 266 is generally in the form of a rounded screw head, having a slot 270 extending axially therein. This design permits easy assembly of the components of the invention, such that the second end 266 can be press fit through the opening within annular flange 263, to provide an axially movably interlocking fit between first segment 260 and second segment 262.

Figure 25:
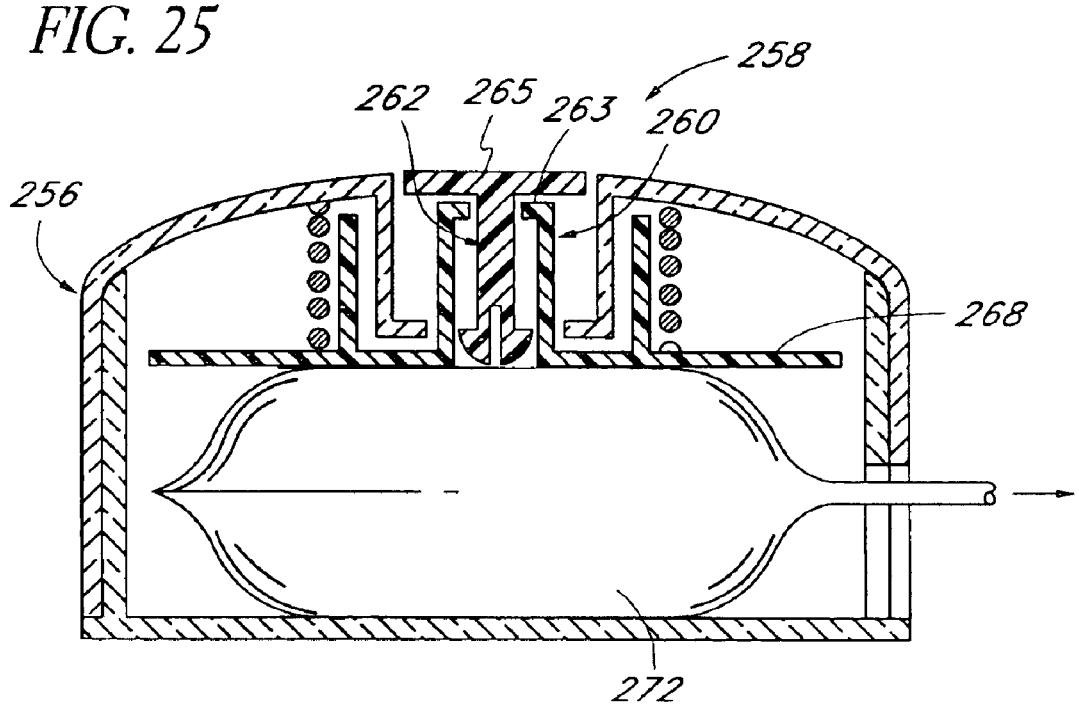
FIG. 25 is an elevational cross-sectional view of an infusion pump having a collapsible platen retractor.
Figure 26:
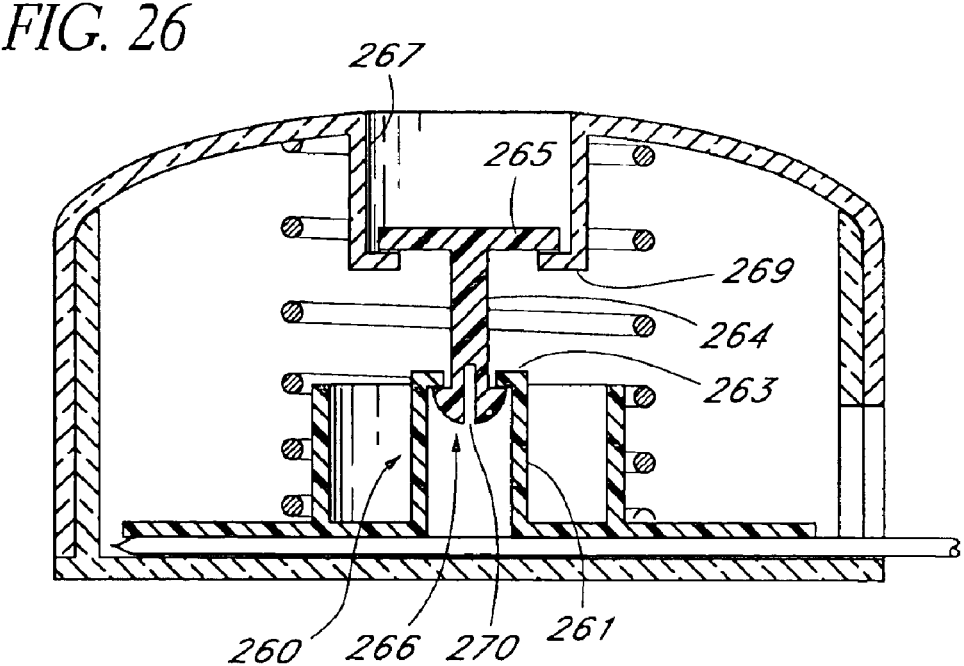
FIG. 26 is an elevational cross-sectional view of the pump of FIG. 25, at the completion of the dispensation cycle.

Retraction of the platen 268 against the spring bias in the embodiment illustrated in FIGS. 25–26 can be accomplished in any of a variety of ways disclosed elsewhere herein. For example, first end 265 can be provided with an exterior thread, for threadably receiving a key such as that illustrated in FIG. 22. In this manner, first end 265 can be drawn axially against the direction of force generated by the spring, to retract platen 268 to the position illustrated in FIG. 25. At that time, a medication bag 272 is inserted into the pump 256 such as by insertion through a lateral opening, or by removal of the base of the pump 256. Following introduction of the medication bag 272, the key (not illustrated) is removed from the first end 265. As illustrated in FIG. 25, the second segment 262 can thereafter be slidably collapsed within the tubular body 261 of first segment 260, to provide a sleek exterior profile of the infusion pump 256.

Alternatively, any of the additional retraction structures disclosed herein can also be incorporated into the present embodiment.

Figure 27:
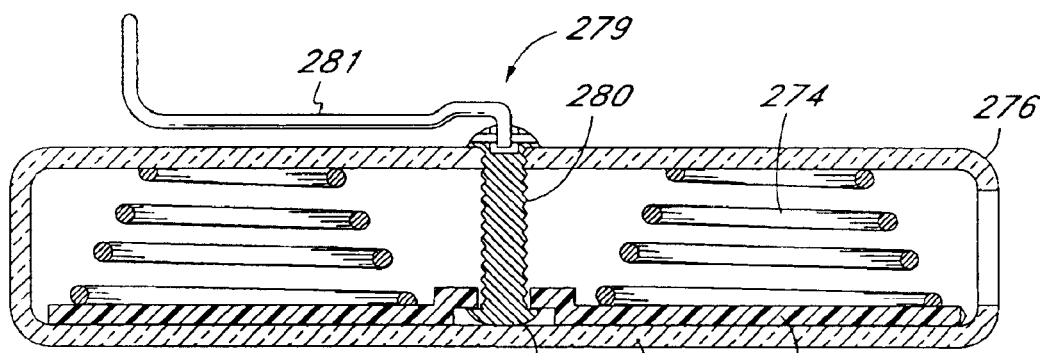
FIG. 27 is an elevational cross-sectional view of an ultra-low profile pump in accordance with the present invention.
Figure 28:
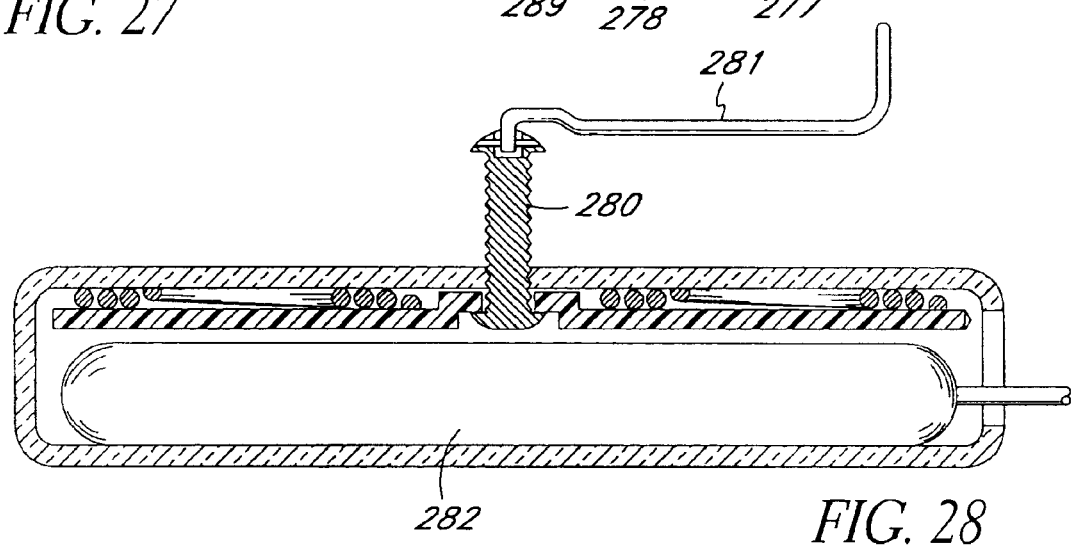
FIG. 28 is an elevational cross-sectional view of the pump of FIG. 27, with the platen fully retracted.
Figure 29:
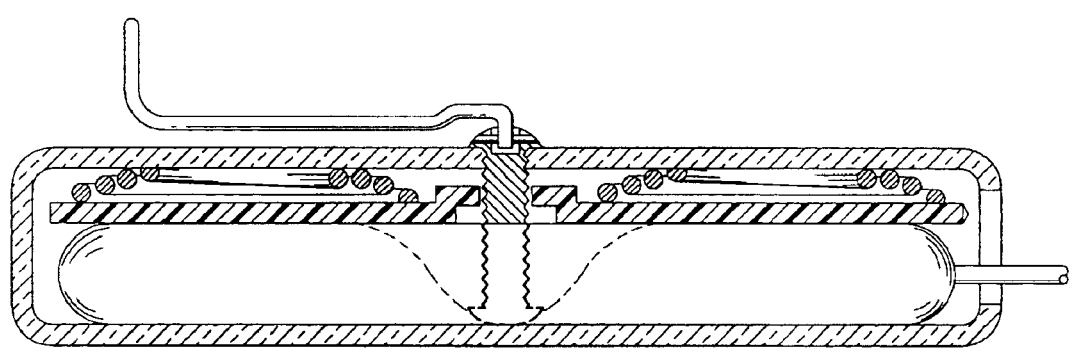
FIG. 29 is an elevational cross-sectional view of the pump of FIG. 27, at the commencement of the dispensation cycle.

Referring to FIGS. 27–29, there is disclosed an ultra-flat spring powered pump comprising at least one spring 274, positioned within a housing 276 for biasing a platen 277 against a base wall 278 for compressing a fluid medication bag therebetween. Platen 277 is retracted against the force of the spring 274 by a rotatable retraction mechanism 279.

Preferably, retraction mechanism 279 comprises a threaded shaft 280 which is rotatably linked to platen 277. This is conveniently accomplished by providing a radially enlarged anchor 289 on the end of shaft 280 and positioning shaft 280 through an opening in platen 278 which is too small to permit passage of anchor 289, as illustrated.

The proximal end of shaft 280 is adapted to receive a crank 281 to permit the patient to rotate the threaded shaft 280 to retract platen 277. In the illustrated embodiment, an opening in the upper portion of the housing is provided with a complementary female threaded surface for cooperating with the threads on threaded shaft 280.

In this embodiment, the platen 277 is retracted by rotating the threaded shaft 280 so that a medication bag 282 can be installed between the platen and the base. Thereafter, in order to reduce the profile of the pump, the threaded shaft 280 may be rotated in a reverse direction to advance fully or partially axially back into the medication bag 282 as illustrated in FIG. 29. For this purpose, medication bag 282 preferably comprises a material which will permit the flexible deformation illustrated in FIG. 29, and the volume of fluid contained in the medication bag 282 should be sufficiently low in relation to the elastic limit of the bag, to accommodate the displacement illustrated in FIG. 29.

Figure 30:
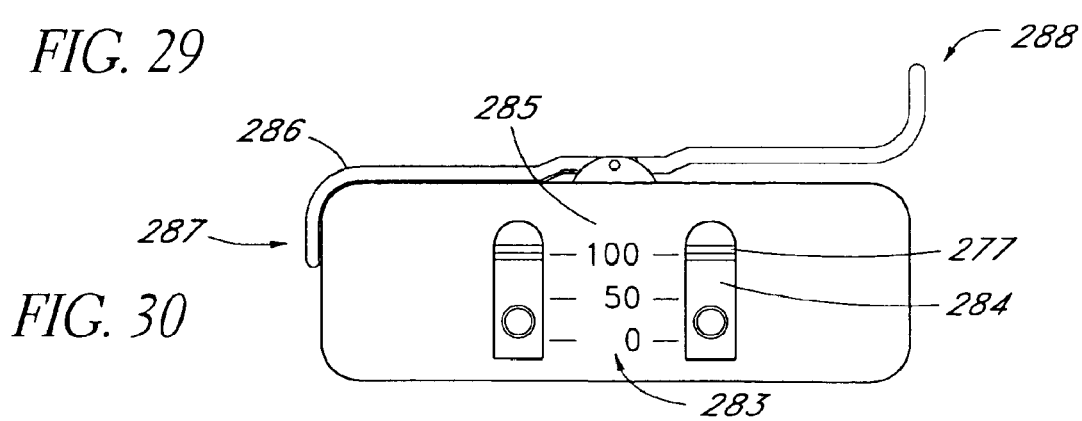
FIG. 30 is an elevational view of the pump illustrated in FIG. 29.

Referring to FIG. 30, there is disclosed an end elevational view of an infusion pump such as that illustrated in FIGS. 27–29. As illustrated therein, a scale 283 provides an indicium of the relative status of the pump throughout the dispensation cycle. In the illustrated embodiment, the platen 277, or an extension of the platen 277 is visible through an opening 284 on the side of the housing. Status indicium 285 are provided on the side of the housing for allowing the user to roughly quantitatively evaluate the remaining portion of the dispensation cycle.

For example, in the illustrated embodiment, the scale 283 runs from 100 to zero. This scale may represent the percentage of remaining medication in the bag. Alternatively, in a device which is dimensioned to accommodate a 100 cc delivery bag, the scale could indicate remaining milliliters of medication. In an embodiment having a single, known flow rate and medication volume, the indicium 285 can be provided in units of time such as hours or minutes, reflecting the remaining time of the dispensation cycle.

Also illustrated in FIG. 30 is an alternative crank arrangement for retracting the platen 277. Crank 286 is pivotally attached to threaded shaft 280, so that it can be conveniently moved from a first compact position 287 such as during storage or use, to a second ready position 288 in which the crank is positioned for use in retracting the platen 277.

Figure 31:
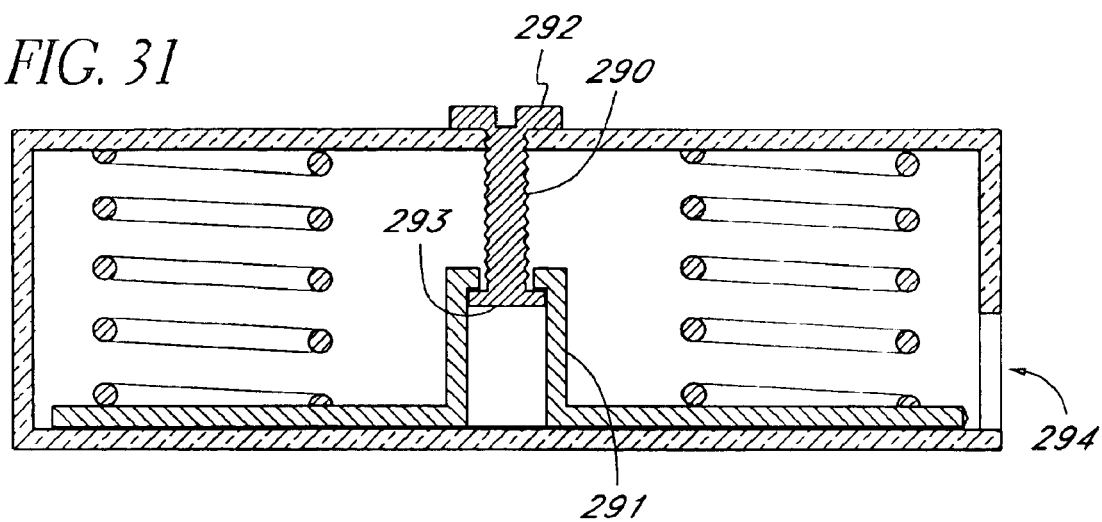
FIG. 31 is an elevational cross-sectional view of an alternate platen retractor in accordance with the present invention.
Figure 32:
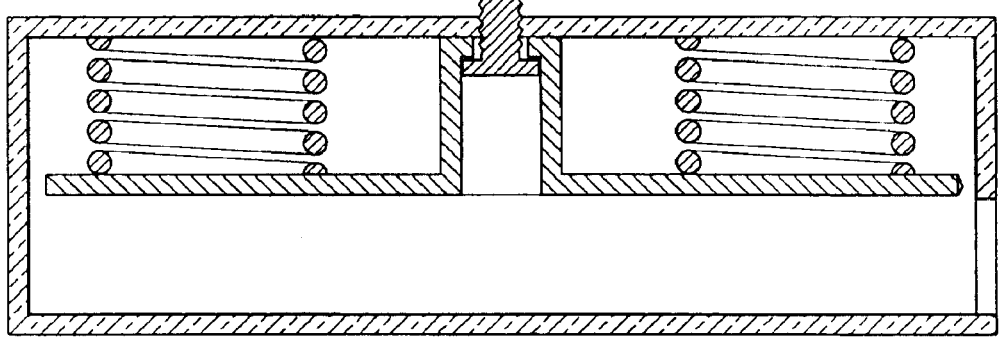
FIG. 32 is an elevational cross-sectional view of the retractor of FIG. 31, in the fully retracted position.
Figure 33:
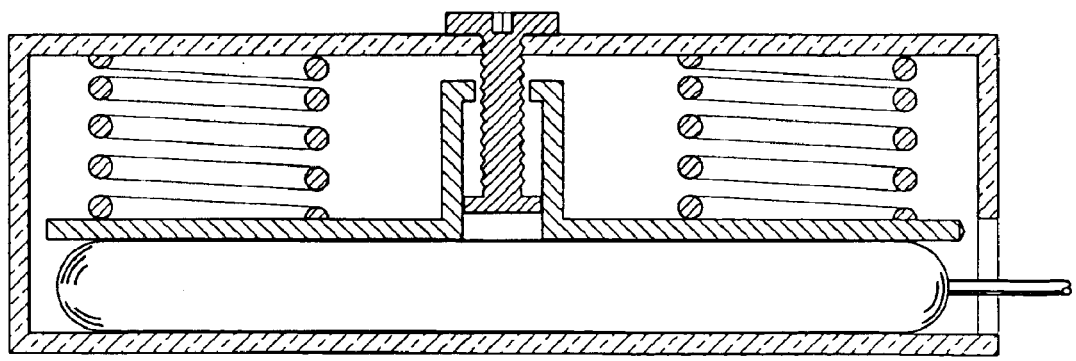
FIG. 33 is an elevational cross-sectional view of the retractor of FIG. 31, at the commencement of the dispensation cycle.

Referring to FIGS. 31–33, there is disclosed an alternate embodiment of an infusion pump having a collapsible, segmented, platen retraction and retention structure. This embodiment permits the use of a threaded retractor such as that illustrated in FIGS. 27–29, yet permits the threaded retractor to be reinserted into the pump to provide a generally smooth exterior configuration, without indenting the medication bag.

Referring to FIG. 31, a first segment 290 preferably comprises a threaded post which engages complementary threads in an opening in the top of the pump housing, so that rotation of the threaded post draws the post axially through the opening of the housing. First end 292 and second end 293 of first segment 290 are provided with an enlargement such as a disc-shaped stop, for reasons which have been previously discussed, for example, in connection with the embodiments illustrated in FIGS. 25–29. Similarly, second segment 291 preferably comprises a tubular element analogous in structure and function to the segment 260 illustrated in FIG. 25. In either embodiment, however, a variety of alternative structures for retracting and restraining the platen such as only partially indenting the medication bag, will be apparent to those of skill in the art in view of the disclosure herein.

Referring to FIG. 32, rotation of the threaded shaft 290 draws the platen against the bias provided by the spring, to produce an opening for receiving a fluid medication bag. In the illustrated embodiment, two coil springs are illustrated in cross section. However, anywhere from about one to about five or more springs can readily be incorporated into a design of the present invention.

Threaded post 290 can be rotated using any of a variety of implements, such as an "ALLEN WRENCH" or similar multi-sided tool, a crank, a rotatable nut, an electric drill, or others as will be apparent to one of skill in the art.

The dimensions of the embodiment illustrated in FIGS. 31–33 can be varied throughout a considerable range, depending upon the desired volume of medication to be infused in a given dispensation cycle, as well as other considerations that will be apparent to one of skill in the art. In general, however, the thickness of the pump along an axis parallel to the longitudinal axis of the spring is preferably no thicker than about 2 inches, and more preferably within a range of from about 1.4 inches to about 1.6 inches in an embodiment adapted for receiving a 0.5-inch thick medication bag. In this embodiment, the distance between the retracted platen and the base is preferably about 0.6 inch, to permit sufficient clearance to easily install a medication bag.

Preferably, as discussed in connection with FIGS. 27–30, the edge of the platen is visible through the opening 294 or other window to permit the user to assess the remaining fluid volume in the medication bag.

Figure 34:
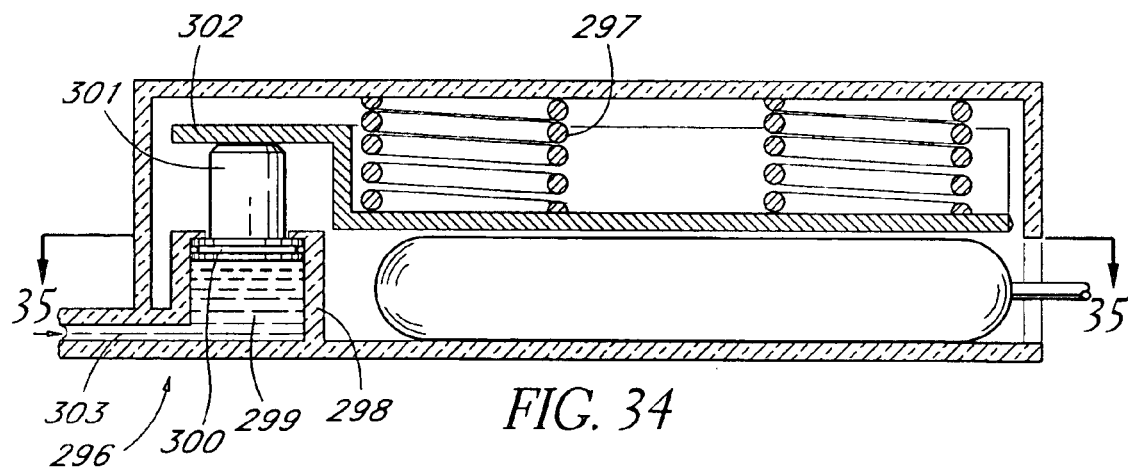
FIG. 34 is an elevational cross-sectional view of a pneumatic platen retractor embodiment of the present invention.
Figure 35:
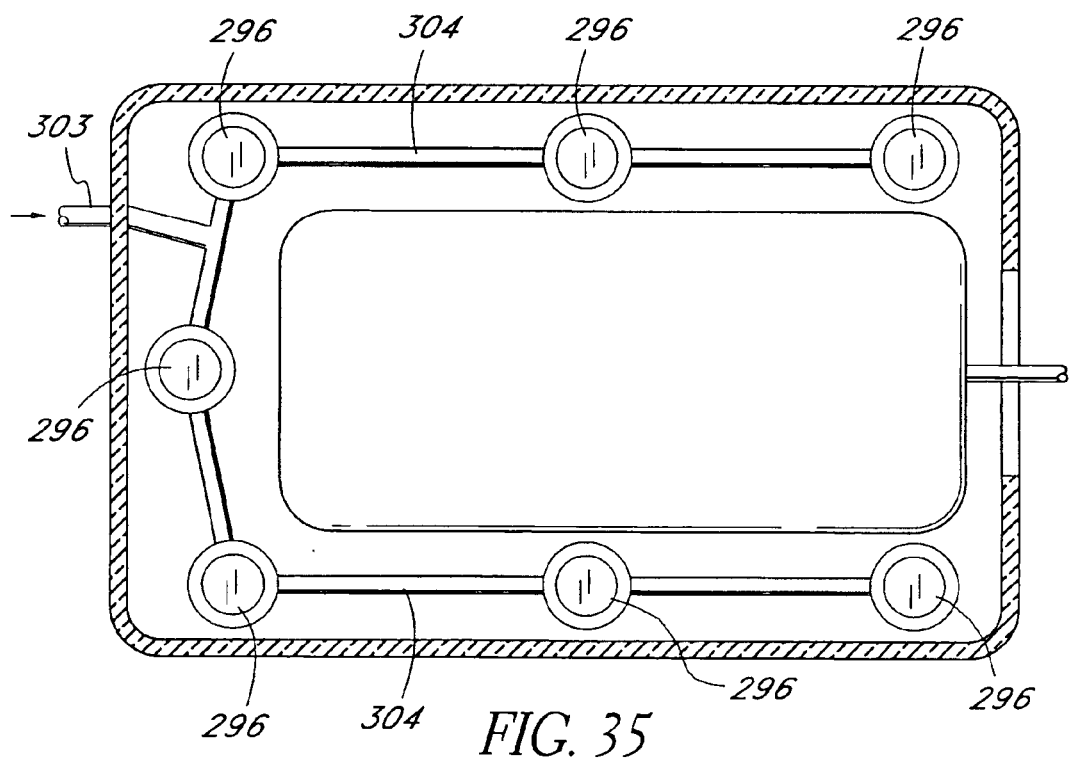
FIG. 35 is a top plan view of the embodiment illustrated in FIG. 34.

Retraction of the platen in order to facilitate introduction of a medication bag can alternatively be accomplished through any of a variety of hydraulic or pneumatic means. For example, referring to FIGS. 34 and 35, there is provided a pneumatic lift for moving the platen from a second distended position to a first retracted position to facilitate introduction of a medication bag. In this embodiment, there is provided one or more pneumatic cylinders 296 for advancing the platen against the bias provided by one or more springs 297. Pneumatic cylinder 296 generally comprises a housing 298 for defining a chamber 299, having at least one movable wall 300 axially slidably disposed within the housing 298 to enlarge or contract the volume of chamber 299. Movable wall 300 is mechanically linked to platen 302 by a spacer 301. Movable wall 300 is provided with any of a variety of known sealing rings or other means for providing a seal between the movable wall 300 and housing 298.

At least one port 303 is provided on the housing for communicating with the chamber 299. In operation, a source of a pressurized material such as a fluid or gas is placed in communication with port 303 and forced into chamber 299 under sufficient pressure to advance wall 300 against the force resulting from one or more springs 297.

In a preferred embodiment, two or more pneumatic cylinders 296 are provided. Thus, for example, there is disclosed in FIG. 35 a top plan view of an infusion pump having seven pneumatic cylinders 296 positioned about the periphery of a medication bag. To facilitate retraction of the platen by infusing pressurized fluid or gas through only a single port 303, each of the chambers 299 of the pneumatic cylinders 296 are in communication with each other by way of a flow path 304.

In accordance with one embodiment, four pneumatic cylinders 296 are provided, each having an internal diameter of about one-half inch. This provides a surface area on movable wall 300 of approximately 0.196 square inches per pneumatic cylinder, for a total of 0.784 square inches for the set of four. To provide a lift of 150 pounds, assuming no friction, a fluid will need to be introduced into port 303 at approximately 190 psi. By doubling the piston area to 1.57 square inches, such as by providing eight pistons instead of four, the required pressure of the pneumatic fluid drops to about 95 psi. A variety of pressure sources can be utilized, as is discussed infra.

Figure 36:
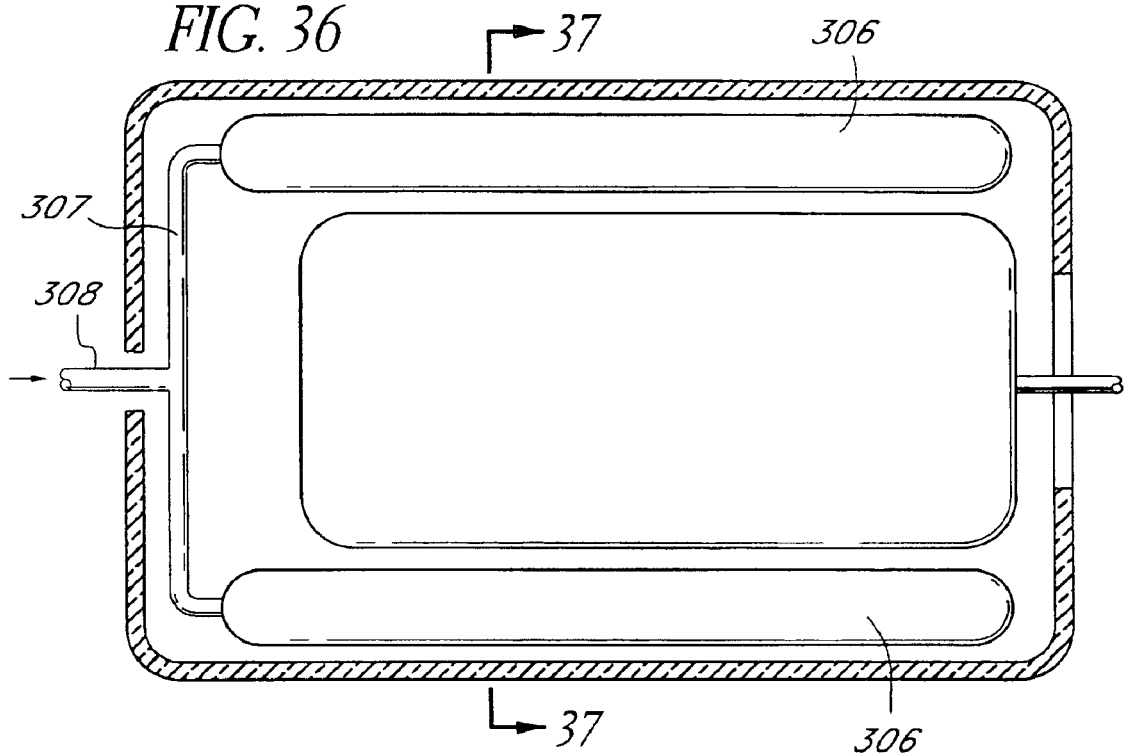
FIG. 36 is a top plan view of a flexible platen retraction device in accordance with the present invention.
Figure 37:
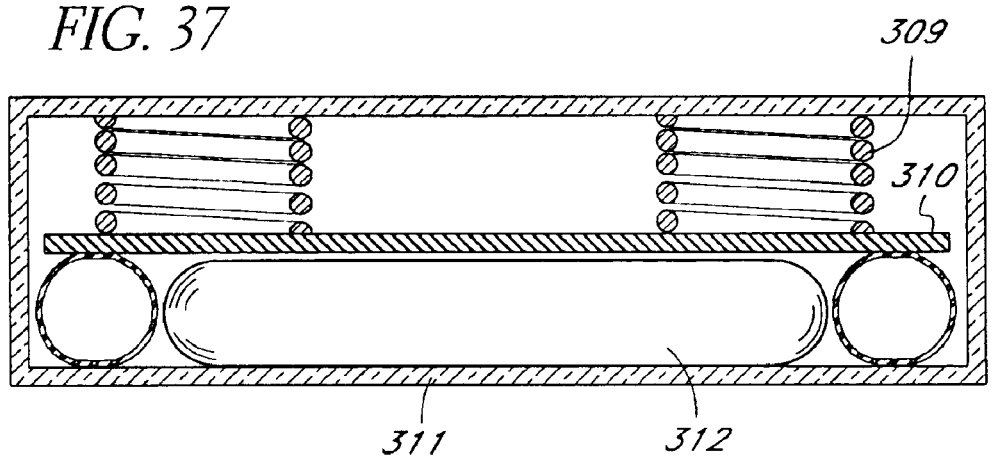
FIG. 37 is an elevational cross-sectional view of the embodiment of FIG. 36.
Figure 38:
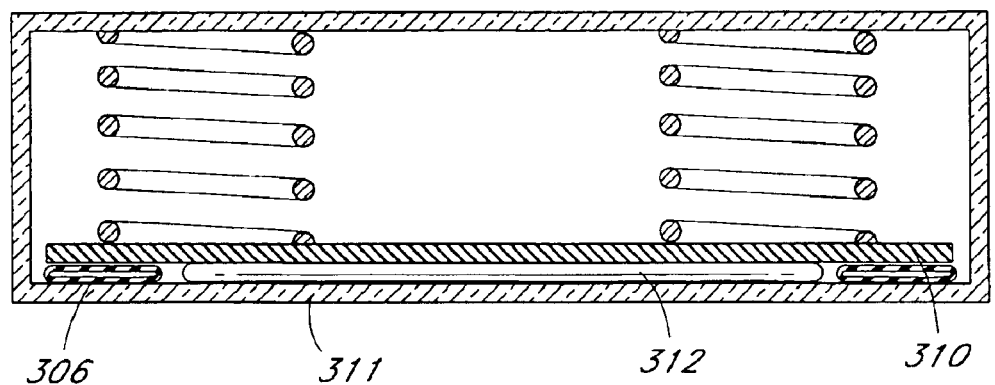
FIG. 38 is an elevational cross-sectional view of the embodiment of FIG. 36, at the completion of the dispensation cycle.

Alternatively, referring to FIGS. 36–38, there is disclosed a pneumatic retraction embodiment in which one or more flexible bladders are utilized to provide the force necessary to retract the platen against the spring bias. Thus, referring to FIG. 36, there is disclosed a top plan view of an embodiment of the present invention having two elongate tubular bladders 306 in communication with a fill port 308 by way of lumen 307. As illustrated in FIGS. 37 and 38, inflation of the bladders 306 advances the platen against the spring bias provided by one or more springs 309 to provide sufficient space between platen 310 and base 311 to accommodate a full medication bag 312.

Any of a variety of configurations for bladder 306 may be utilized in accomplishing the present embodiment of the invention. In general, the bladder comprises one or more elongate tubular bodies having a diameter which is sufficient in its inflated state to provide a sufficient distance between the platen 310 and base 311 to accommodate the medication bag 312. The axial length of the bladder 306 will depend upon the size of the medication bag contemplated, together with factors such as the maximum acceptable pump housing size, and the maximum acceptable pressure required to retract the platen. In general, the larger volume of bladder 306 will enable the use of less compressive force to retract the platen, but will require a larger housing as will be apparent to one of skill in the art.

Motive force for filling the bladder 306 can be provided in any of a variety of ways, utilizing either a fluid or a gas medium. For example, the fill port 308 can be provided with a luer connector or other conventional means for establishing fluid communication with a conventional syringe having a volume sufficient to inflate the bladder 306. The syringe may be filled with water, or air, depending upon the relative force characteristics of the bladder and spring. In the hospital or clinical setting, pressurized air from a house compression system, such as is commonly available through a wall outlet in the patient's room, can be utilized. Alternatively, compressed $CO_2$ cartridges or other convenient sources of pressurized air or liquid can be readily utilized.

Figure 40:
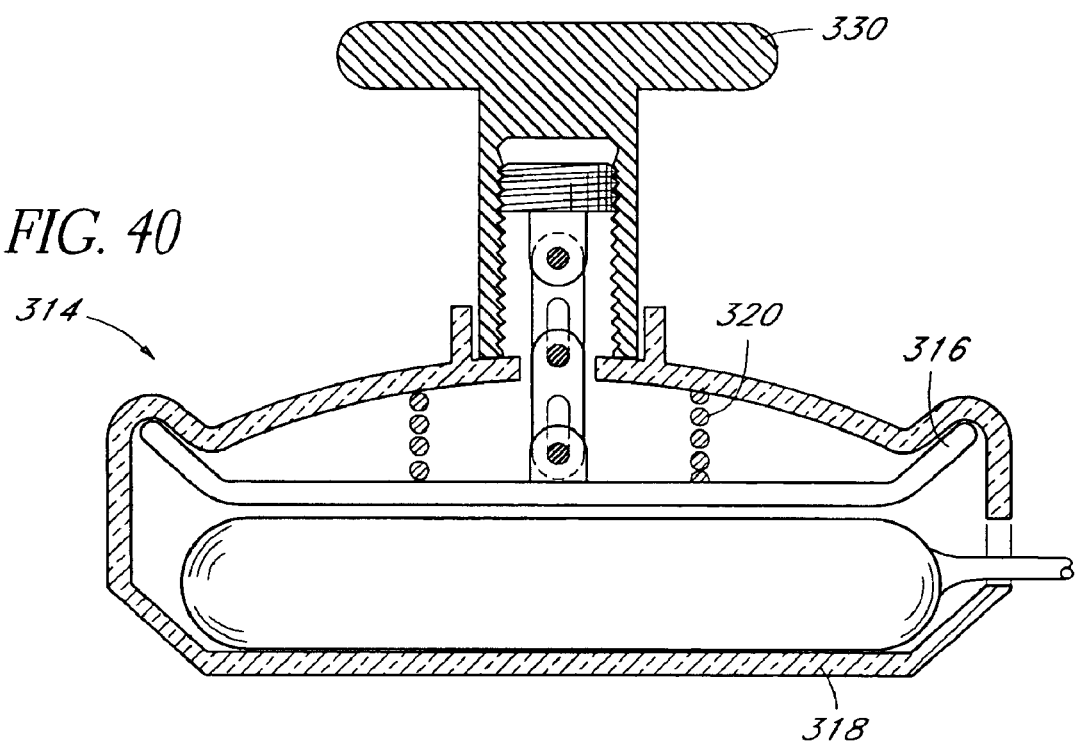
FIG. 40 is an elevational cross-sectional view of the embodiment of FIG. 39, with a retracting key in place.
Figure 41:
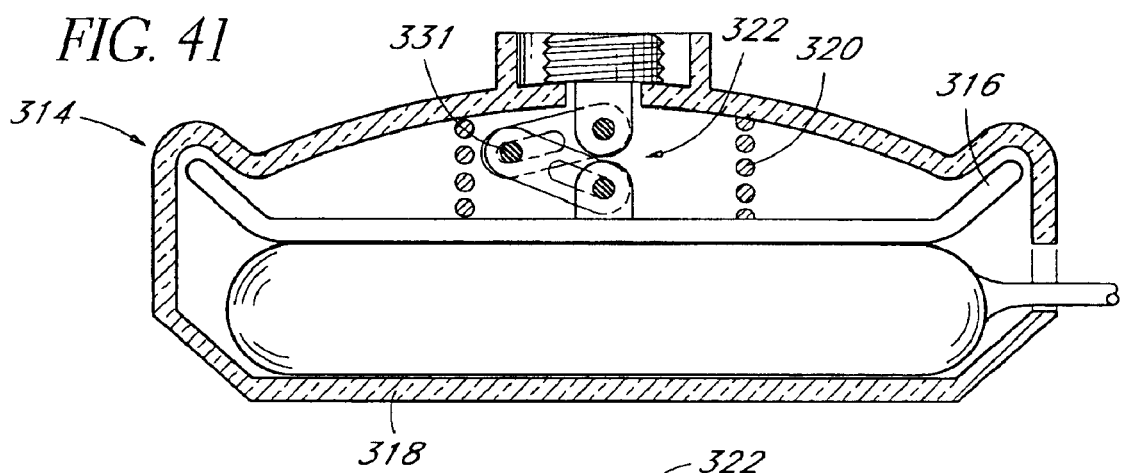
FIG. 41 is an elevational cross-sectional view of the embodiment of FIG. 39, at the commencement of dispensation cycle.
Figure 39:
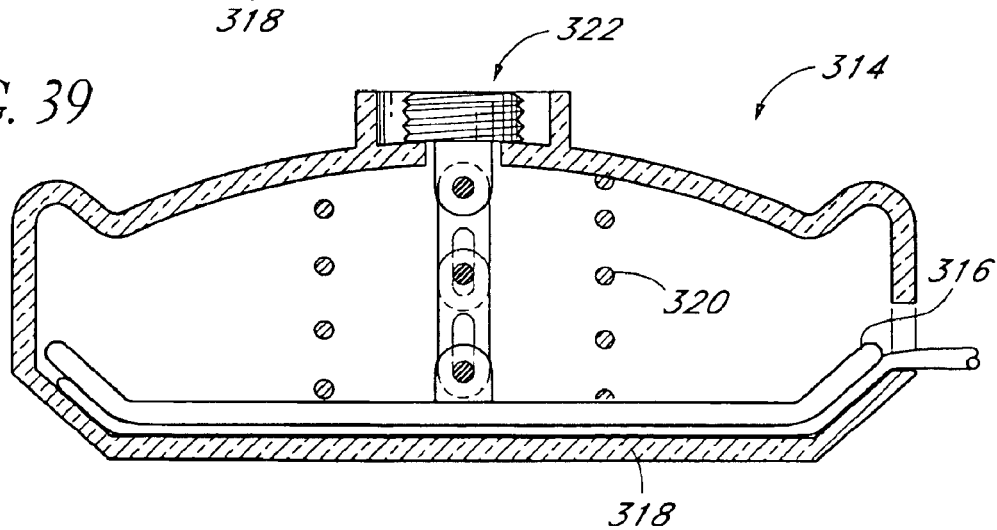
FIG. 39 is an elevational cross-sectional view of the folding link platen retractor in accordance with the present invention.

Referring to FIGS. 39–41, there is disclosed a further embodiment of the infusion pump in accordance with the present invention. In this embodiment, retraction of the platen is accomplished by the use of a threaded key, as has been previously discussed, and the overall thickness of the infusion pump is minimized through the use of a folding link lift mechanism.

In this embodiment, infusion pump 314 is provided with one or more springs 320 for biasing a platen 316 in the direction of base 318, as has been previously discussed. In order to limit the distal travel of platen 316, such as when the base 318 is removed, and to retract the platen 316 against the bias provided by spring 320, a retraction and retention structure 322 is provided.

Figure 42:
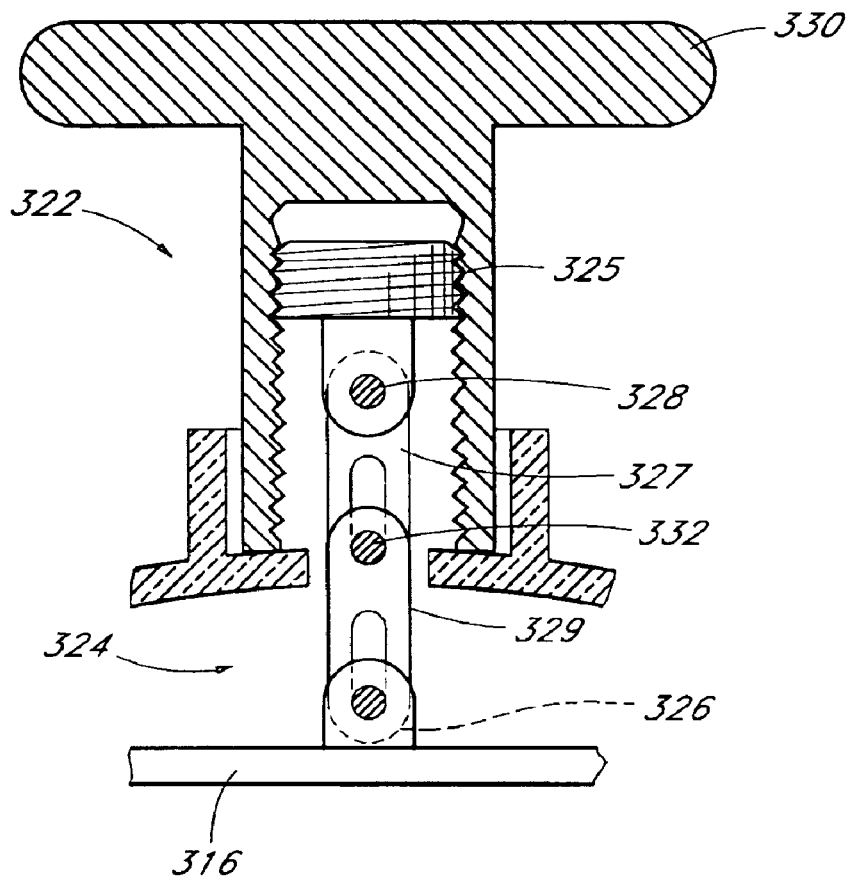
FIG. 42 is an elevational view of a linkage assembly.

Referring to FIG. 42, the retraction and retention structure 322 generally comprises a folding linkage assembly 324. The linkage assembly 324 permits the relative movement of proximal end 325 and distal end 326 between a first position in which proximal end 325 and distal end 326 are spaced apart by a predetermined maximum distance, and a second position in which proximal end 325 and distal end 326 are spaced apart by a lesser distance.

In the embodiment illustrated in FIG. 42, linkage assembly 324 is provided with a first segment 327, which is pivotably secured to the proximal end 325 such as by a pin 328. The distal end of linkage 327 is provided with a slip joint connection with a second linkage 329. The slip joint connection is conveniently accomplished by providing one of the first and second linkages with an axially extending slot, and the other of the first and second linkages with a pin 332 for extending through the slot, together with an anchor such as a nut, soldered washer or pin for preventing removal of the pin 332 from the slot.

The second linkage 329 is thereafter pivotably connected to the platen 316, such as by providing a proximally extending flange on the platen 316 for pivotally engaging the distal end of the second linkage 329.

Preferably, this embodiment is provided with a threaded plug at the proximal end 325 of folding linkage 324, adapted to be received within a key 330, as has been discussed in connection with previous embodiments. Alternatively, other retraction structures such as a lever can also be used in the present embodiment. One function of the linkage 324 in the threaded plug embodiment is to resist rotation of the plug during rotation of the key. Thus, if an alternative to linkage 324 such as a multistrand braided cable is used, some additional registering structure should be provided to resist rotation of the threaded plug.

In use, the threaded plug is engaged within the key 330, and withdrawn by rotation of the key 330 to retract the platen 316 to the loaded position. While the platen is being retracted against the spring bias, the first linkage 327 and second linkage 329 become extended to their axial limit.

After installation of the medication bag, the key is removed by reverse rotation with respect to the housing, and the linkage assembly 324 can be collapsed back into the housing, as illustrated in FIG. 41, by pressing upon the proximal end 325. Preferably, releasable retention structures are provided for retaining the proximal end 325 within or against the housing, to maintain the outer profile of the pump at a minimum during the dispensation cycle. For example, any of a variety of recesses and snap-fit interrelationships between the proximal end 325 and the housing can be incorporated, which take advantage of the plastic deformability of the materials of the housing.

In accordance with one embodiment of this aspect of the present invention, the linkage assembly 324 is configured so that the maximum length between the proximal end 325 and distal end 326 is about 1.0 inches. Thus, a coil spring having a relaxed length of about 7 inches will be permitted to expand no more than about 1.0 inches in axial length by the end of the dispensation cycle. Preferably, the loaded infusion pump 314 will have a thickness of no more than about 1.2–1.6 inches, so that the collapsed distance between proximal end 325 and distal end 326 of linkage assembly 324 is within the range of from about 0.3 to about 0.5 inches.

Linkages 327 and 329 can be manufactured in any of a variety of ways which will be well known to those of skill in the art. For example, linkages 327 and 329 may be pressed or stamped from sheet metal stock, such as aluminum or stainless steel, and thereafter drilled or punched with the appropriate slots and pivot holes, or may be molded from any of a variety of plastic moldable materials having sufficient strength for this intended application.

In one embodiment of the invention, linkages 327 and 329 are punched out of 0.1 inch thick stainless steel sheet, with a width of about 0.25 inches and a length of about 0.6 inches. The axial length of the slot is about 0.4 inches, and pivots are formed using rivets, screws or the like.

In an alternate embodiment, the first and second linkages are pivotally connected together without the use of a slip joint. This construction may extend pivot 331 (FIG. 41) farther in a lateral direction than pivot 332 (FIG. 42) when the platen is in the retracted position and the proximal end 325 of linkage 324 is pressed back inside the housing. Depending upon other design parameters, as will be apparent, the embodiment of FIG. 42 may be utilized with a relatively smaller diameter spring 320.

Figure 43:
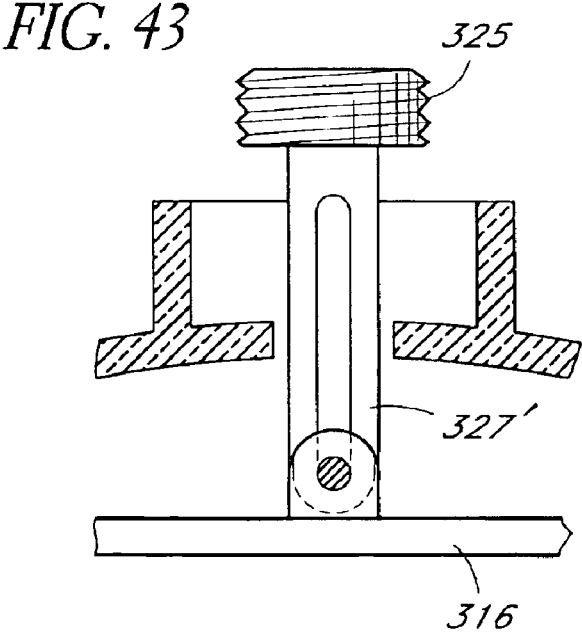
FIG. 43 is an elevational view of an alternate linkage assembly.

As a further alternative, the linkage connection comprises a unitary link 327', as illustrated in FIG. 43. As will be apparent to one of skill in the art, the outer profile of an infusion pump having the linkage 327' of FIG. 43 will be relatively larger than an embodiment having a collapsible linkage assembly. In addition, compressive force such as by the patient upon the threaded plug 325 in the embodiment illustrated in FIG. 43 will be additive to the spring force, and potentially cause changes in the effluent fluid flow rate. Thus, this embodiment, although relatively simply to manufacture, may be desirably utilized only in circumstances where the outer profile and compression issues are not of concern.

The foregoing designs have been determined to produce a relatively constant output profile throughout the dispensation cycle of devices incorporating these designs. However, even with reasonable prestressing of the spring, output pressure generally declines over the dispensation cycle as the spring relaxes and the pressure contact area on the bag changes. Provision of a spring having a higher spring constant or higher pretension can change the starting force and ending force throughout a dispensation cycle, but generally not appreciably flatten the output force or contact area profile.

Figure 60:
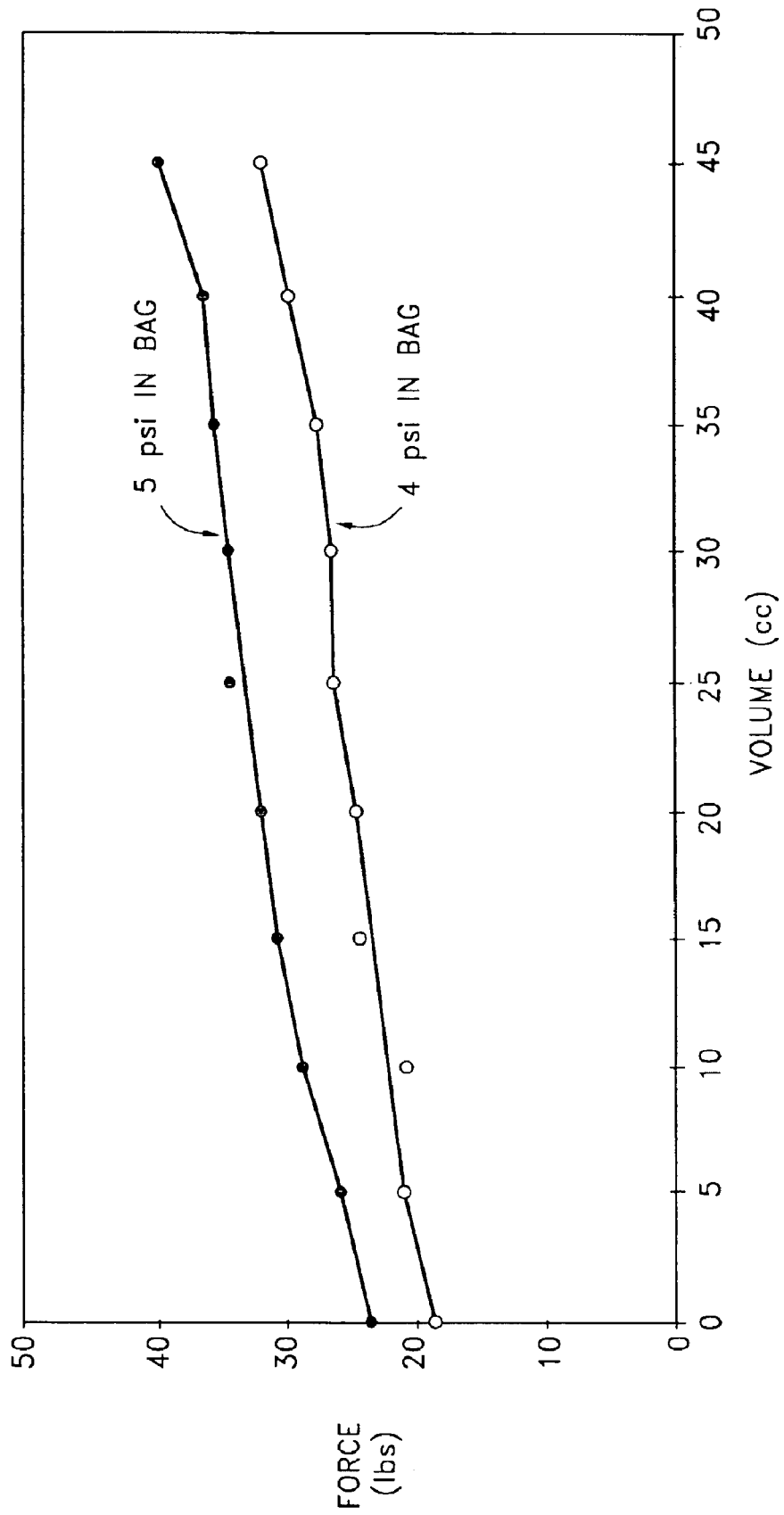
FIG. 60 is a plot of force versus volume.

In a test where the internal pressure of the bag was maintained at a constant 5 lbs./in² while the contents were delivered, it was found that the force applied to the bag needed to be increased from 24 lbs. force at the beginning of the dispensation cycle to 40 lbs. force near the completion of the dispensation cycle. See FIG. 60.

Thus, in accordance with a further aspect of the present invention, there is provided an element for introducing a drag or resistance to distal travel of the platen to produce a flattening of the output pressure profile. Preferably, the amount of drag on the distal movement of the platen changes continuously over a portion or all of the dispensation cycle, having a maximum value at the commencement of the dispensation cycle and reaching a minimum value at some point between the commencement and end of the dispensation cycle. Preferably, the declining drag provided by the drag elements complements the declining spring force throughout the dispensation cycle in a manner that produces a substantially flat net spring and bag contact area and force throughout the dispensation cycle. Of the two, the changing bag contact area is a greater negative influence than the declining spring force.

Figure 44:
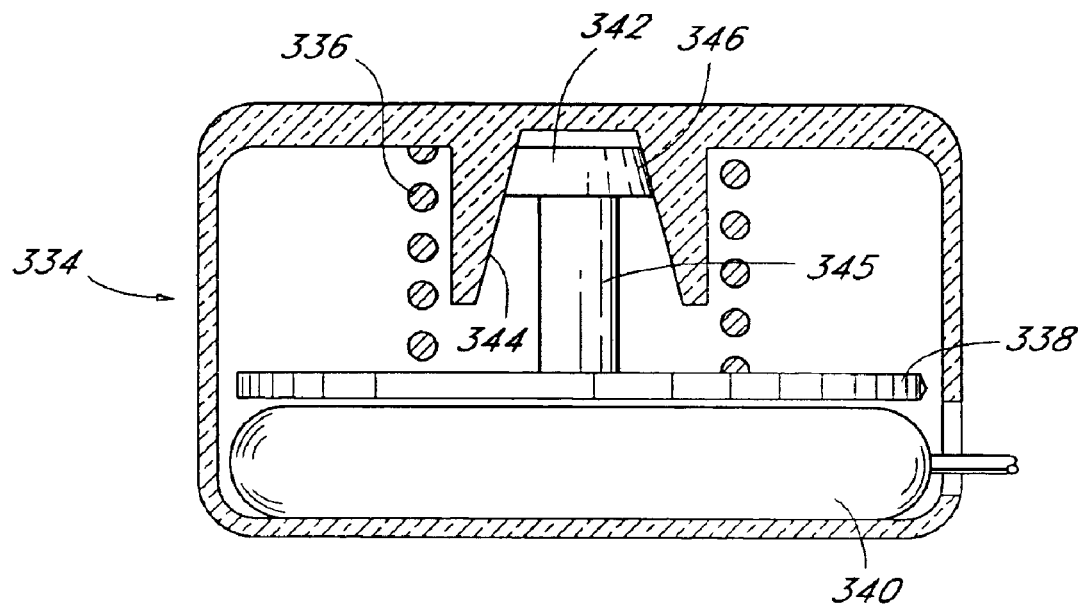
FIG. 44 is an elevational cross-sectional view of an infusion pump having a drag element in accordance with the present invention.

Thus, referring to FIG. 44, there is disclosed an infusion pump 334 having one or more springs 336 for biasing a platen 338 against a medication bag 340. Platen 338 is provided with at least one drag element 342 for contacting a friction surface 344 throughout at least a portion of its axial length of travel. Drag element 342 can be provided in any of a variety of forms, and can extend radially outwardly within the plane of the platen 338, or be spaced apart axially from the plane of the platen, such as is illustrated in FIG. 44.

In the illustrated embodiment, drag element 342 comprises an axially extending support 345, having a generally transverse element 346 at the proximal end thereof. Element 346 engages at least one friction surface 344, which, in the illustrated embodiment, ramps radially outwardly away from element 346 as the element 346 travels in the distal direction. Element 342 preferably comprises a resilient material such as a rubber or other elastomer, such as neoprene.

Element 346 and surface 344 can take any of a variety of configurations. For example, in the illustrated embodiment, element 346 can take the shape of a circular disk, extending within a generally frusto-conically shaped well, having annular surface 344 extending around the well. Alternatively, surface 344 can be provided on only one side or opposing sides of a bilaterally symmetrical element 342. Retraction of platen 338 in the proximal direction forces element 342 against surface 344, to provide a relatively tight fit, which dissipates as element 342 is drawn axially in the distal direction.

In a simplified embodiment, the interior wall of the pump housing is ramped or stepped slightly in the radially inward direction along all or a portion of its interior circumference. This ramped or stepped region extends radially inwardly in the proximal direction, so that the smallest cross-sectional area occurs at the beginning of the dispensation cycle. At that point, the radially exterior edge of the platen 338 frictionally engages the step or ramp to provide a resistance to distal travel which dissipates or disappears at some point along the distal travel of the platen.

In general, in a stepped friction surface embodiment, the step will extend throughout no more than about the first one half or one third of the travel. However, the extent of friction desired and the rate of taper or location of the distal edge of the step will vary depending upon the spring constant and amount of prestress, and the bag contact area, and can be optimized for any particular embodiment through routine experimentation by one of skill in the art.

In accordance with one embodiment of the present invention, a drag element is constructed as shown in FIG. 44. A 50 cc medication bag is inserted within the infusion pump, and the change in spring force exerted against the bag, as well as the drag due to the resistance element, are measured at each 10-cc increment of fluid dispensation. The following results are obtained:

TABLE 1

| fill | spring force | output pressure w/o drag element | drag w/ element | net change w/ drag element | output w/ drag element |
| --- | --- | --- | --- | --- | --- |
| 50 ml | 40 lbs. | +8 psi | −13 lbs. | 0 | 5 psi |
| 40 ml | 39 lbs. | +7 psi | −11 lbs. | 0 | 5 psi |
| 30 ml | 38 lbs. | +5.9 psi | −8.8 lbs. | 0 | 5 psi |
| 20 ml | 37 lbs. | +4.4 psi | −6.4 lbs. | 0 | 5 psi |
| 10 ml | 36 lbs. | +2.4 psi | −3.4 lbs. | 0 | 5 psi |
| 0 ml | 35 lbs. | 0 psi | 0 lbs. | 0 | 5 psi |

Figure 45:
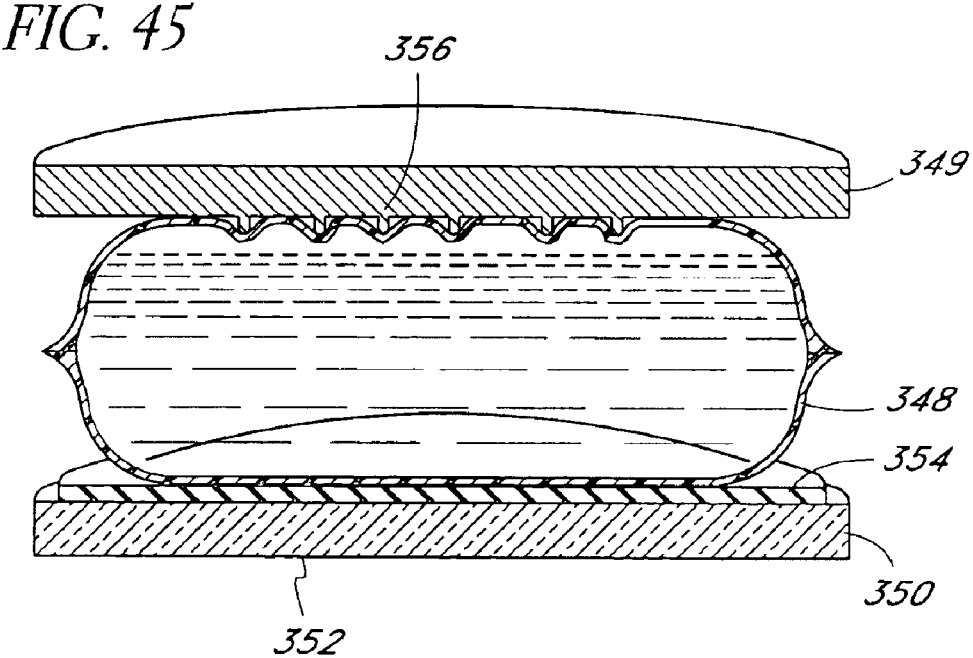
FIG. 45 is an elevational cross-sectional view of an empty indicator in accordance with the present invention.
Figure 46:
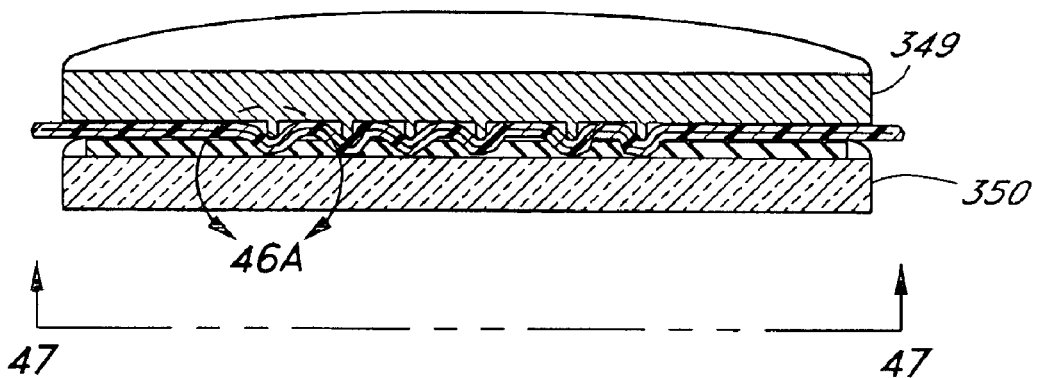
FIG. 46 is an elevational cross-sectional view of the embodiment of FIG. 45, at the completion of the dispensation cycle.
Figure 46A:
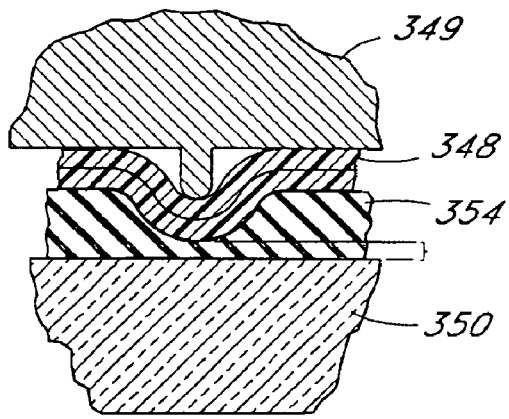
FIG. 46A is an enlarged portion of an elevational cross-sectional view of the embodiment of FIG. 45, at the completion of the dispensation cycle.
Figure 47:
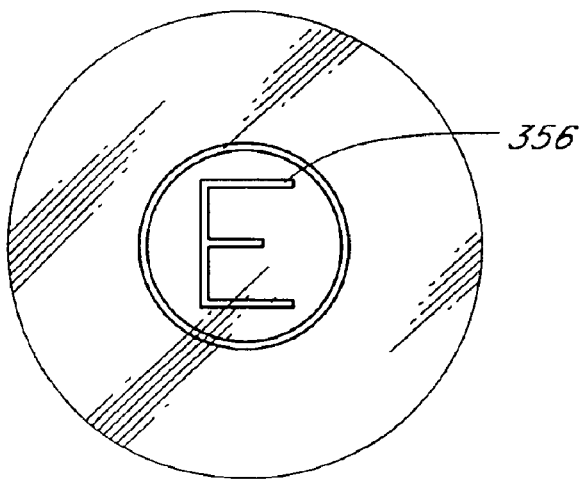
FIG. 47 is a bottom plan view through the transparent window of the embodiment of FIG. 45.

In accordance with a further aspect of the present invention, there is provided an indicium of the status of the dispensation cycle, which can be readily incorporated into any of the previously disclosed embodiments. Referring to FIG. 45, there is disclosed a fluid medication bag 348, positioned between a platen 349 and the base 350 of an infusion pump. Preferably, at least a portion of base 350 comprises a transparent window 352, such as polycarbonate or clear polypropylene, or other materials well known in the art. Disposed between the medication bag 348 and the platen 349 is a membrane 354, which will be discussed in detail infra.

The platen 349, or a cover for the platen, is provided with at least one embossed symbol 356, such as an E indicating "empty." The embossed symbol is preferably raised from the planar surface of the platen.

When the medication has been fully expelled from bag 348, the embossed symbol 356 is pressed by the platen 349 into the membrane 354 and the symbol 356 embossed on the platen becomes visible through the window 352 in the base 350 of the infusion pump. For this purpose, membrane 354 may comprise any of a variety of materials such as rubber or silicone. Membrane 354 is preferably has a thickness within the range of from about 0.020 inches to about 0.030 inches. However, the thickness of the membrane 354 and material can be varied considerably, depending upon the native pigmentation in the membrane and compressibility under the force due to the spring. The embossed letters are preferably raised to a height of about 0.04 inches from the surface of the platen.

Figure 49:
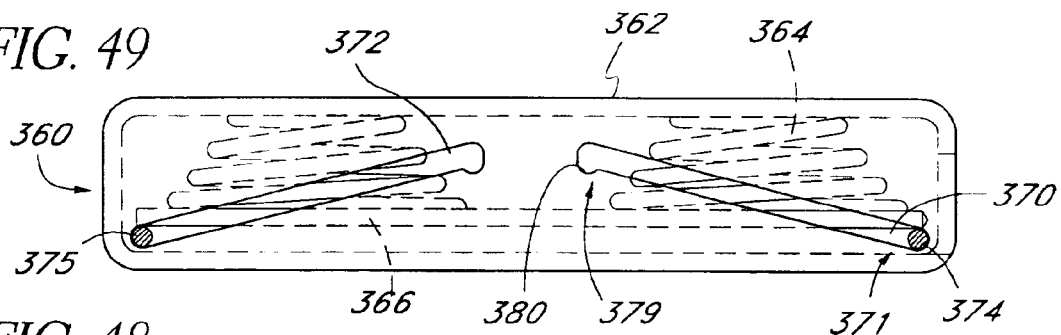
FIG. 49 is a side elevational view of the embodiment of FIG. 48.
Figure 48:
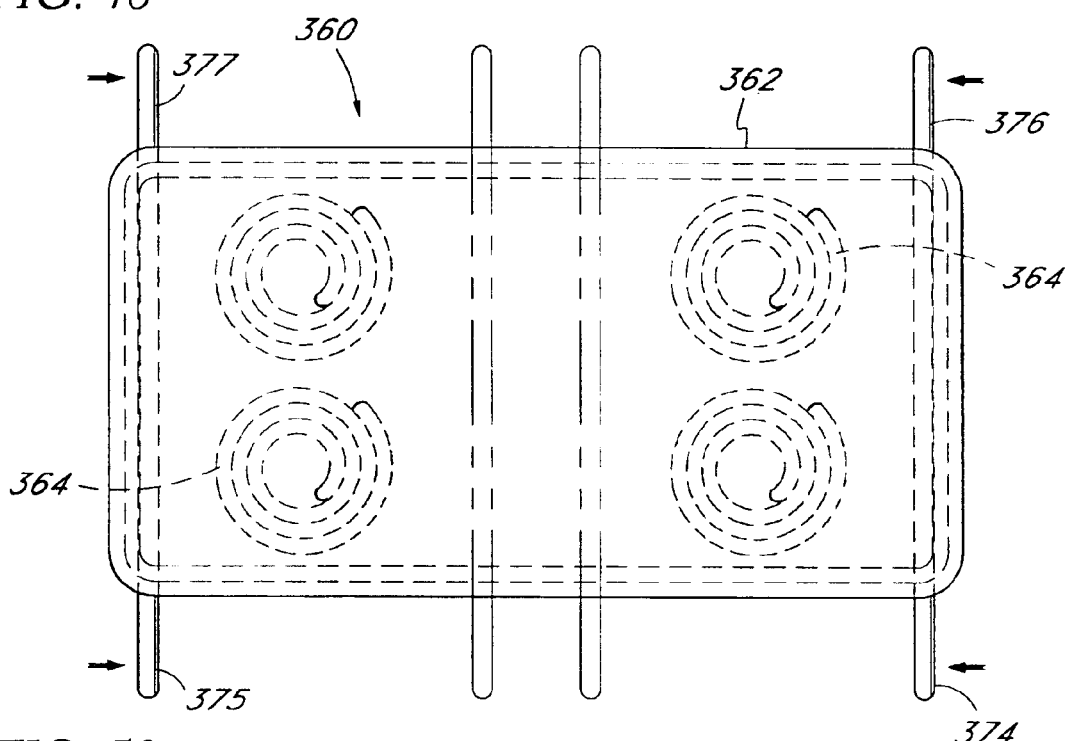
FIG. 48 is a top plan view of a low-profile sliding spring retractor embodiment of the present invention.
Figure 50:
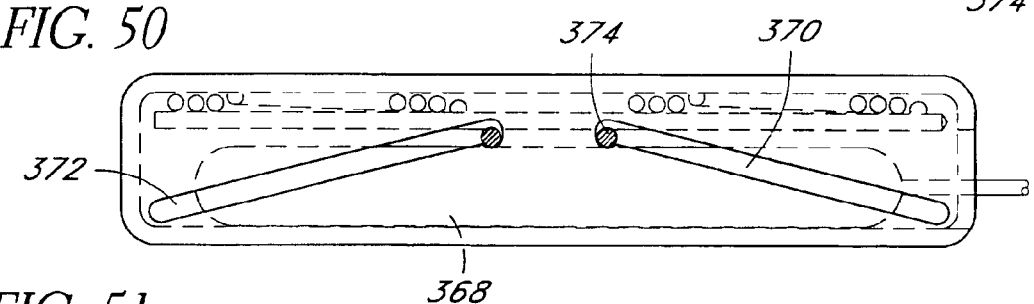
FIG. 50 is a side elevational view of the embodiment of FIG. 48, at the commencement of the dispensation cycle.

Referring to FIGS. 48 through 51, there is disclosed an ultra low profile sliding spring retractor embodiment in accordance with a further aspect of the present invention. Infusion pump 360 is provided with a housing 362, having a platen 366 contained therein which is biased in the direction of a fluid medication bag 368 by one or more springs 364. In the illustrated embodiment, four coil springs 364 are provided, each having a generally conical configuration so that the axial length of the compressed spring is no more than the diameter of the spring coil wire, as illustrated in FIG. 50.

The platen 366 is retracted against the bias from spring 364 by one or more levers 374 movably disposed along an inclined path such as slot 370 with respect to the housing 362. Preferably, at least one pair of opposing levers 374 and 376 are provided, and, in the illustrated embodiment, a second pair of levers 375 and 377 are also provided. Referring to FIG. 49, lever 374 rides in a slot 370 formed in a housing 362. Slot 370 is inclined from a first end 371 to a second end 379 in an axial and medial direction. Similarly, lever 375 travels in slot 372, which inclines medially in the axial direction. In this manner, the user can place a thumb on lever 375 and a forefinger on lever 374, and compress the two levers together to advance the platen against the spring bias. Inclusion of a mirror image pair of levers 376 and 377 for traveling in corresponding inclined slots (not illustrated) on the opposite side of the housing 362, the amount of force required to be exerted by each hand of the user is divided in half, and provides a more convenient force distribution within the platen pump 360.

In one embodiment of the invention, each of levers 374, 375, 376 and 377 are separately movably mounted within their respective slots in the housing 362. For example, each lever is integrally molded with or secured to the platen 366, and, preferably, provided with a bearing such as a roller bearing (not illustrated) for minimizing friction during reciprocal travel within the corresponding inclined path of travel.

Alternatively, each opposing member of a pair of levers are joined through the center of the device, to provide a single post extending therethrough. For example, lever 374 and 376 can comprise opposite ends of a single shaft, which extends through or adjacent to the platen 366. This design simplifies the construction of the pump in some aspects, such as by eliminating the torque which would otherwise occur at bearing and or connecting of the lever to the platen 366. The unitary post can either be permanently mounted within the housing, or removably positionable within a through lumen, so that the posts can be removed from the unit once the medication bag has been inserted.

Figure 51:
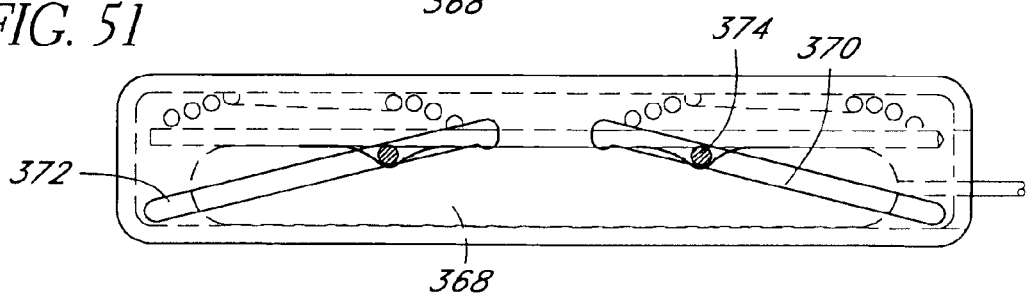
FIG. 51 is a side elevational view of the embodiment of FIG. 48, partway through the dispensation cycle.

In the illustrated embodiment, opposing levers 374 and 376 are opposite ends of a unitary post, and opposing levers 375 and 377 are similarly opposing ends of a unitary post. The posts in this embodiment extend along the medication bag 368 side of platen 366, as is illustrated in FIGS. 50 and 51. FIG. 50 illustrates a side elevational view of an embodiment of the invention in which the posts are retained in the retracted position, such as for insertion of the medication bag 368. FIG. 51 illustrates a point in the dispensation cycle of the embodiment of FIG. 50, with the posts remaining in position adjacent the platen 366.

Referring to FIG. 49, the medial most extent 379 of the path of travel for lever 374 is provided with a detent 380, for removably retaining the lever 374 at the fully retracted position such as during loading. After each of the levers has been advanced to the detent 380, the platen 366 will be releasably retained in the retracted position to permit insertion of a fluid medication bag 368 between the platen 366 and the bottom of housing 362. This can be accomplished in any of a variety of ways disclosed elsewhere herein, such as by introduction of the fluid bag 368 through a side opening in the housing 362, or by providing the housing 362 with a hinged bottom wall which can be opened to insert the fluid medication bag 368. Following installation of the bag, each lever 374 can be advanced laterally slightly out of the corresponding detent 380, so that the lever 374 is no longer retaining the spring bias. The levers thereafter may be withdrawn from the device, or folded at a hinge point (not illustrated) to reduce the peripheral profile of the device.

Preferably, the angle of the path of travel of lever 374, which, in the illustrated embodiment is governed by the angle of the slot 370 is within the range of from about 10° to about 20° from the plane of the central region of the platen 366. As will be apparent to one of skill in the art, as the axis of the path of travel of lever 374 approaches perpendicular to the plane of the platen (i.e. approaches the longitudinal axis of travel of spring 364), the leverage obtained in advancing the platen against the spring bias diminishes. Thus, in one embodiment, the slot 370 could extend at a perpendicular to the plane of the platen. However, the patient would be required to exert a significant force in order to retract the platen against the spring bias.

The lower limit on the range of angles between the path of travel of lever 374 and plane of platen 366 is governed by several factors. The axial component of the path of travel must be sufficient to fully retract the platen 366 so that a medication bag 368 can be inserted. Thus, as the angle decreases beyond a certain limit, the length of the path of travel must be increased to obtain the same axial component, thereby requiring a larger outer peripheral dimension of the device. In one preferred embodiment, the housing 362 has a length of about 5 inches and a thickness along the longitudinal axis of spring 364 of about 0.9 inches. Slot 370 inclines at an angle of about 15° from the plane of the central region of the platen 366, and has a length of about 2.2 inches.

Figure 52:
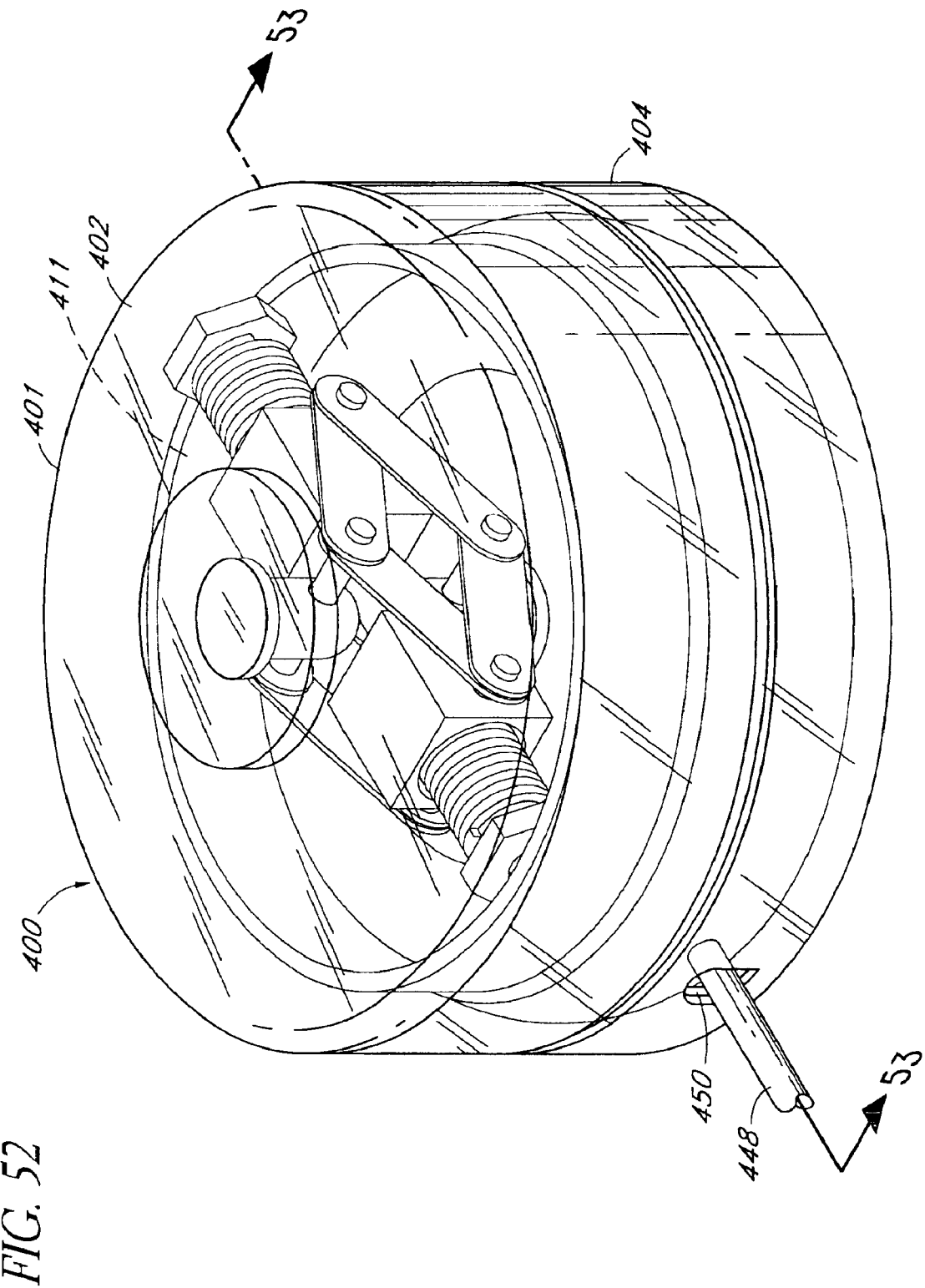
FIG. 52 is a top perspective view of a scissor-type biasing means in accordance with the present invention.

In accordance with a further embodiment of the present invention, there is provided an improved spring biased intravenous infusion pump having a parallelogram "scissor"-type linkage for transferring spring force to the medication reservoir. Referring to FIG. 52, the pump 400 comprises a housing 401 which may be formed as an integral unit, or from two or more detachably connected components as has been previously described.

Figure 53:
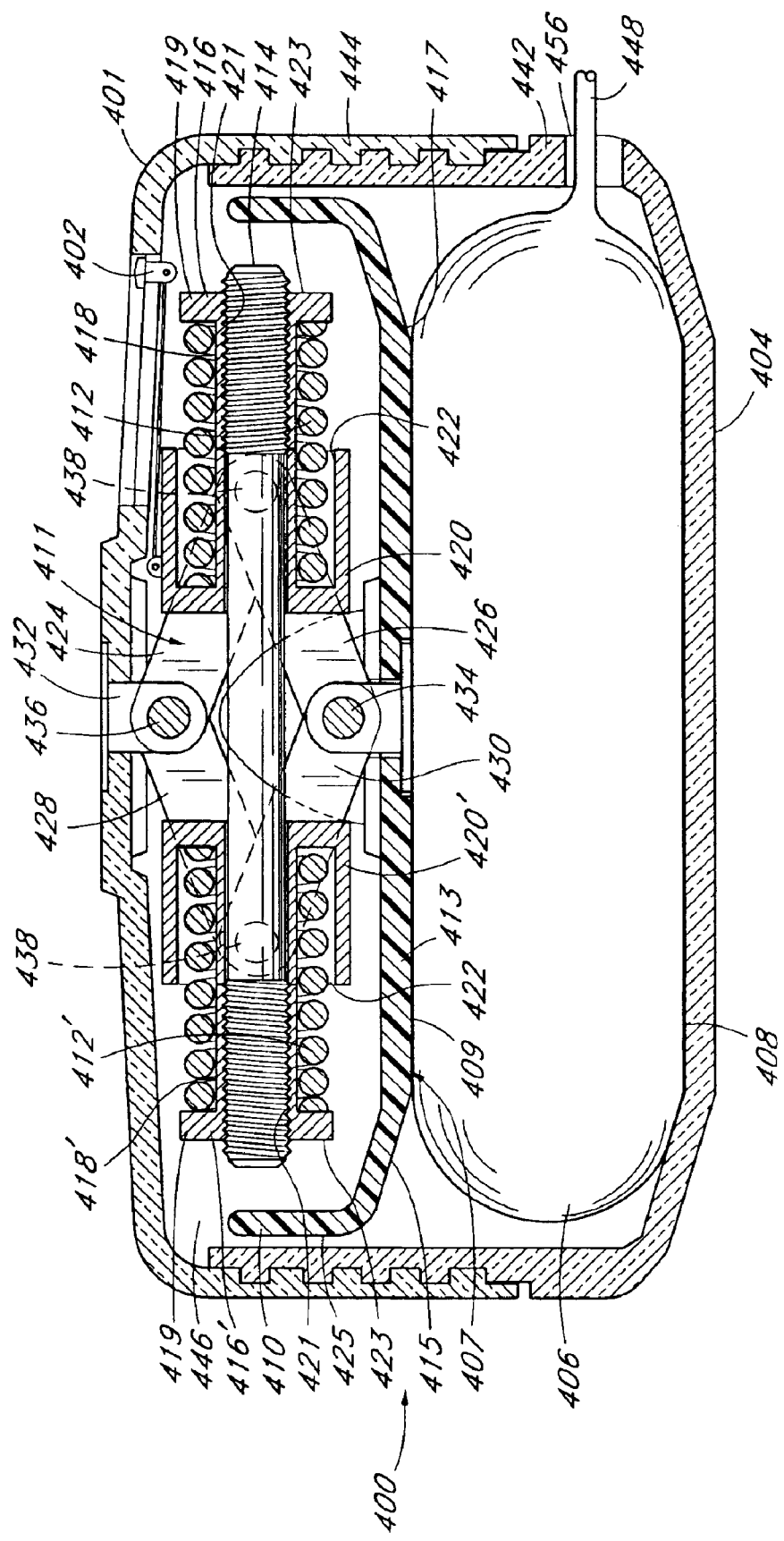
FIG. 53 is an elevational cross-sectional view of the embodiment of FIG. 52.
Figure 54:
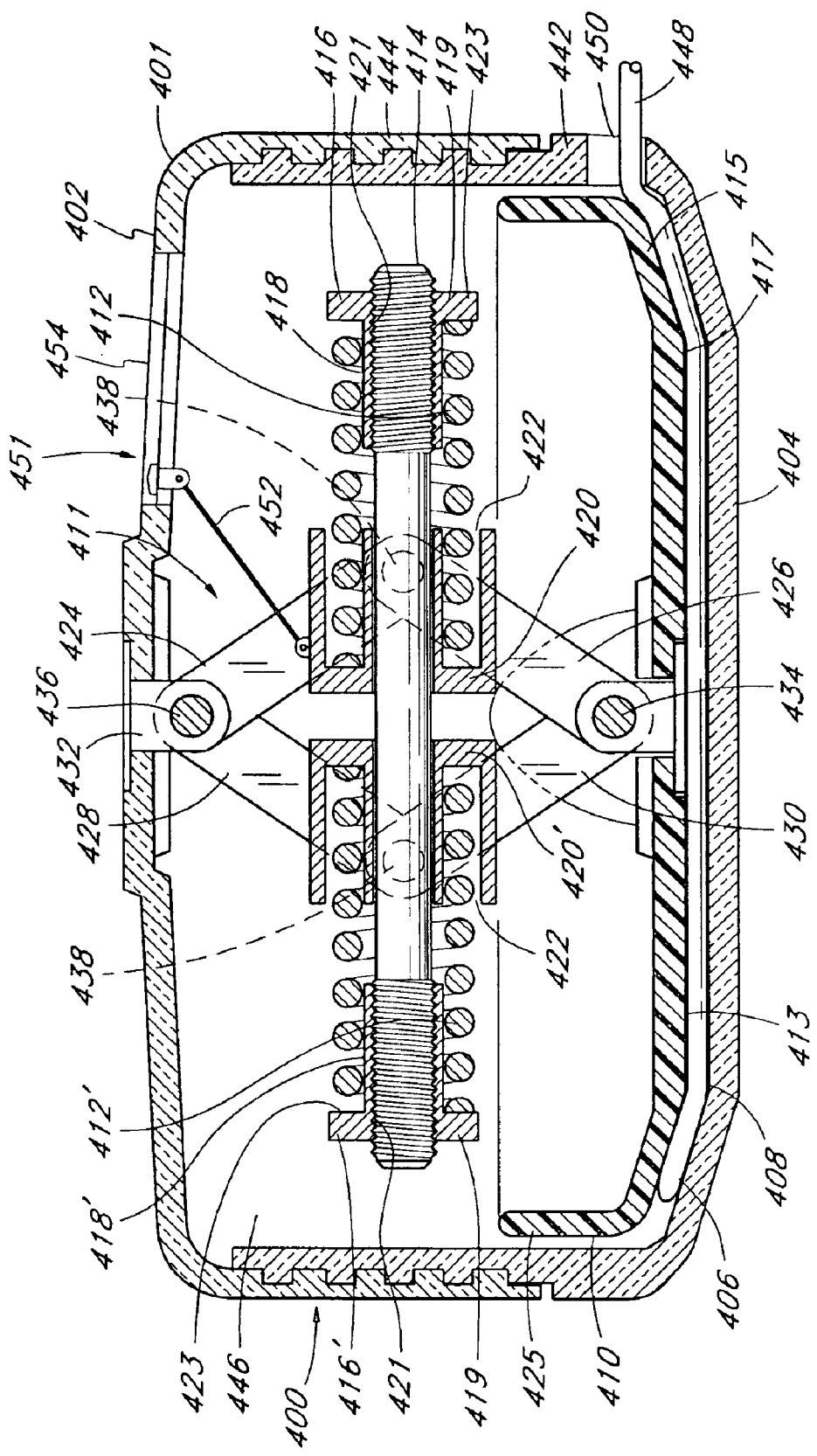
FIG. 54 is an elevational cross-sectional view of the embodiment of FIG. 52, at the completion of the dispensation cycle.

Referring to FIGS. 53 and 54, the preferred detachable component housing 401 comprises a cover 402 and a base 404. Each of the cover 402 and the base 404 contain an annular wall 442 and 444 extending in the axial direction. Complementary threads are preferably provided on the outer surface of the annular wall 442 of the base 404 and inner surface of the annular wall 444 of the cover 402, to facilitate threadable engagement of the cover 402 and base 404 as has been discussed. Alternatively, the contacting surfaces of the cover 402 and base 404 are provided with complementary pins and J- or L-shaped grooves to permit a press-and-twist fit interlock. Any of a variety of alternative interlocking structures may be utilized for the housing 401 of the invention, as will be apparent from the previous disclosures herein.

The cover 402 and base 404 are preferably formed in accordance with conventional techniques for the production of medical device housings, such as injection molding of thermoplastic or thermoset polymers. Alternatively, any of a variety of other techniques may be utilized, including fabrication from sheet metal stock, as will be well understood by one of skill in the art.

In general, base 404 annular wall 442, annular wall 444 and cover 402 cooperate to form a chamber 446 for containing the functional components of the infusion device. In the illustrated embodiment, a platen 410 is biased against a reservoir such as a flexible medication bag 406 by means of a spring and linkage assembly 411.

Fluid bag 406 is in fluid communication with the patient by way of effluent fluid line 448, which extends through the housing 401 by way of a port 450. Modification of the port 450 to accommodate the various relationships between the cover 402 and base 404 will be apparent to one of skill in the art. A flow regulator (not illustrated) to regulate the flow of medication is provided on fluid line 448.

In general, the fluid bag diameters contemplated for use in accordance with the present invention are in the area of from about 3.5 inches in diameter to about 5 inches in diameter and from about 0.5 inches to about 1.0 inches thick. However, infusion pumps adapted to receive other size bags can be readily produced in accordance with the disclosure herein.

Referring to FIGS. 53 and 54, the platen 410 embodiment designed for use with a 3.8 inch diameter, one inch thick, 100 cc. medication bag 406 has both a flat, circular central contact surface 413, having a diameter within the range of from about 2.4 to about 2.8 inches, and an annular ring portion 415 which inclines away from the reservoir contacting side of platen 410. The outside diameter of annular ring portion 415 is generally within the range of from about 3.4 to about 3.6 inches for use with a 3.8-inch diameter flat medication bag 406. Medication bag 406 is approximately 3.5 inches in diameter when full. The angle of the surface of annular ring portion 415 with respect to an extension of the plane of central contact surface 413 is preferably within the range of from about 10° to about 45°, and more preferably within the range of from about 10° to about 30°.

In general, the transition 417 between the central contact surface 413 and the radially inwardmost extent of annular ring portion 415 is positioned so that the circular central contact surface 413 substantially completely covers the planar portion on the upper surface of fluid medication bag 406. Referring to FIG. 53, medication bag 406 comprises a generally planar upper surface, having an outer limit or transition 407 where the peripheral region of bag 406 commences deviation from the plane of upper surface 409.

As illustrated in FIG. 53, the transition point 407 on the bag 406 is roughly coincident with the transition point 417 on the platen 410. Referring to FIG. 54, the interior surface of bottom plate 408 is configured with a complementary nesting surface for platen 410. Preferably, platen 410 contains a guide 425 such as an annular flange extending in the axial direction for stabilizing the platen 410 as it compresses the medication bag 406 against the base 404 of the housing 401.

The platen 410 is biased towards the medication bag 406 through a linkage assembly 414. In general, linkage assembly 411 comprises one or more biasing elements having a longitudinal axis which extends at an angle with respect to the longitudinal axis of travel of platen 410. Preferably, the biasing element axis extends approximately at about a perpendicular to the axis of travel of platen 410. As is discussed below, the biasing element preferably comprises one or more springs having at least one concentric or parallel spring guide such as a central shaft or tubular cover.

In the illustrated embodiment, a spring guide 414 extends along an axis which is generally perpendicular to the axial direction of travel of platen 410. The spring guide 414 conveniently comprises a threaded metal rod having a length within the range of from about 3.0 to about 3.4 inches, and a diameter from about 0.125 inches to about 0.250 inches, although variations will be readily apparent to one of skill in the art.

In an embodiment in which the spring guide 414 comprises a unitary or segmented shaft having a continuous thread extending throughout its length, a tubular sleeve may be conveniently disposed over the portions of the threaded shaft which will slidably carry other moving parts, as will be discussed. Alternatively, the spring guide 414 can be constructed from a generally smooth rod, having a threaded region only on the distal ends thereof for receiving nuts 416 and 416'.

A spring stop is carried at either end of the spring guide 414. As will be readily apparent to one of skill in the art, any of a variety of means can be utilized for retaining a spring under tension. For example, a nut or nut and washer threadably engaged to the spring guide 414 is convenient, both from a manufacturing standpoint, and due to the ability of the manufacturer to adjust the spring tension by simply rotating the nut.

In the illustrated embodiment, a spring stop 419 is provided on each lateral end of the spring guide 414 for limiting the lateral expansion of each spring. The spring stop 419 generally comprises a radially outwardly extending annular flange 423, having an aperture 421 extending axially therethrough for receiving a threaded portion of spring guide 414. Spring stop 419 also has a cross-sectional area through a radial plane sufficient to limit expansion of the spring. Each spring stop 419 is preferably provided with an axially extending tubular sleeve 418 and 418', which in the assembled pump extends medially along the spring guide 414 and within the spring. In the illustrated embodiment, the sleeves 418 and 418' have internal threads complementary to the thread on spring guide 414 to securely threadably retain the spring stop 419 in place.

In an alternate embodiment (not illustrated), the spring stop 419 comprises a radially outwardly extending annular flange 423 and an axially extending tubular sleeve 418, as in the foregoing embodiment. However, the spring stop 419 is held in place by a threaded nut secured directly to the spring guide 414 on the lateral side of outwardly extending annular flange 423. In this embodiment, the internal thread on aperture 421 and interior wall of axially extending tubular sleeve 418 is unnecessary. Although the use of a lateral threaded nut is convenient from a manufacturing standpoint, it adds to the overall lateral length of the spring guide 414, which may be undesirable in a given embodiment.

The springs 412 and 412' are compressed between the spring stops 419 and two axially moveable blocks 420 and 420'. In one embodiment, the springs 412 and 412' comprise music wire having a wire diameter of approximately 0.085 inches. Lower diameters such as 0.080 may also be used by increasing the preload.

Preferably, springs 412 and 412' have a spring constant within the range of from about 80 lbs. per inch to 130 lbs. per inch in a dual spring embodiment. Each spring 412 and 412' is approximately 1.7 inches long in its un-compressed state and approximately 0.9 inches long in its fully compressed state, shown in FIG. 53, and ½ inch in diameter. The sum of the axial travel of springs 412 and 412' is approximately 0.7 inch between the compressed state as shown in FIG. 53 at the beginning of the dispensation cycle and the state shown in FIG. 54 at the end of the dispensation cycle.

Blocks 420 and 420' function as medial spring abutments to mechanically link the medial travel of the spring to the linkage assembly 411 and platen 410. In the illustrated embodiment, blocks 420 and 420' are generally rectangular in exterior configuration and contain an annular or tubular recess 422 on the lateral side which does not go through the entire axial length of the block 420 and 420'. The springs 412 and 412' fit into the recess 422 in each block 420 and 420'. The blocks 420 and 420' also contain an axially extending tubular opening through the center of the block to allow the blocks to slide axially along the spring guide 414.

Each block 420 and 420' may comprise any of a variety of durable materials such as aluminum, stainless steel or other metal known in the medical device arts. Preferably, however, a strong lightweight plastic material such as "DELRIN," available from DuPont is used. Polymeric blocks or coatings are preferred, due to their ability to slide relatively freely on the spring guide 414 when biased by the springs 412 and 412'.

Each of two opposing sides of the blocks 420 and 420' parallel to the spring guide 414 contains a block pivot 438. The relative positioning of pivots and corresponding recesses discussed herein can readily be reversed, as will be apparent to one of skill in the art.

Figure 55:
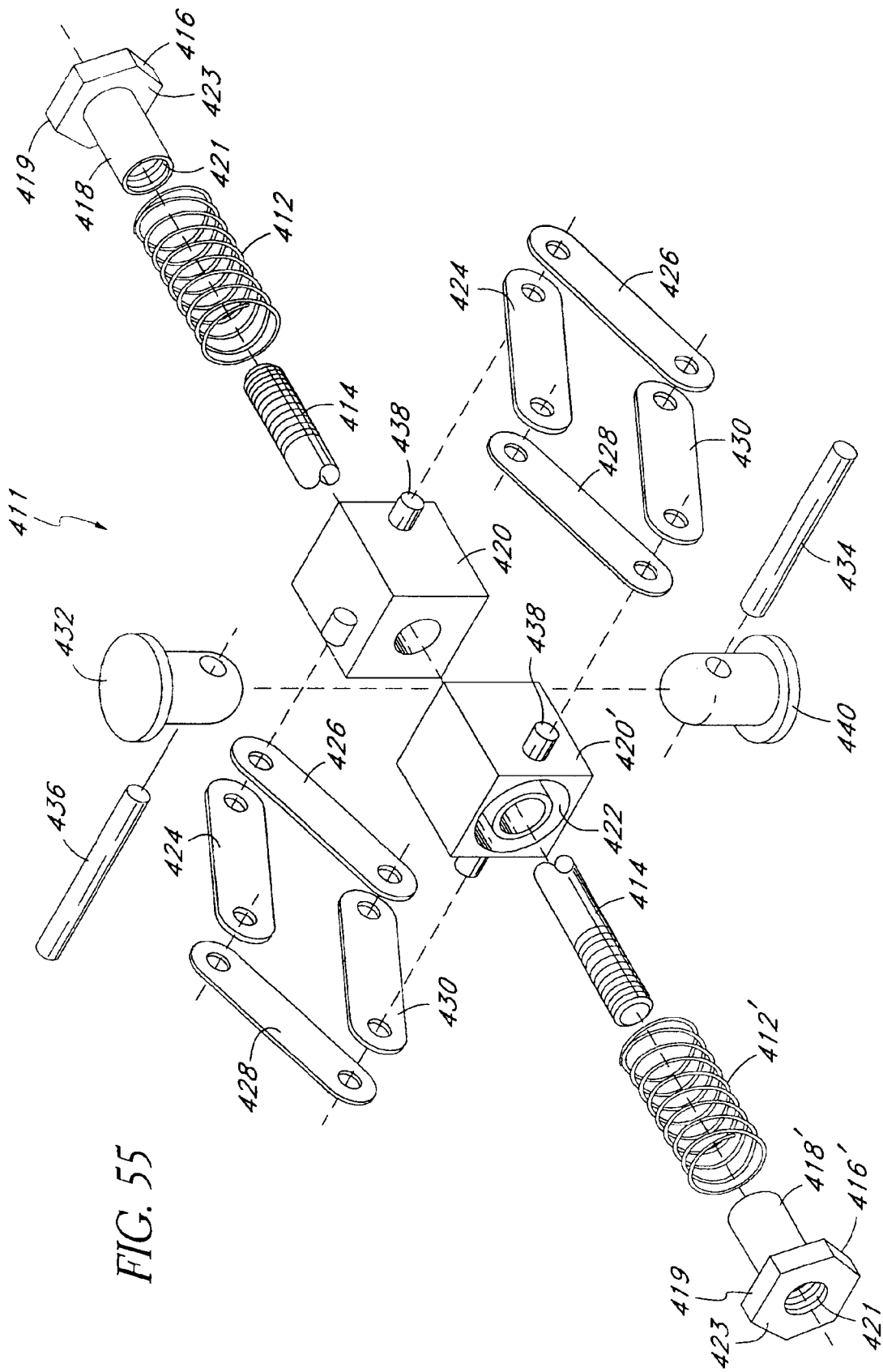
FIG. 55 is an exploded view of the embodiment of FIG. 52.

Two link arms 424 and 426 are pivotably affixed to one pivot 438 at a first end thereof. Link arm 424 is connected at a, second end to an anchor pivot 436 which is connected to the cover 402. Link arm 426 is connected at its second end to a platen pivot 434 which is connected to the platen 410. Link arms 424 and 426 form a scissor-type configuration which is a mirror image of the configuration of link arms 428 and 430. Together, the four link arms 424, 426, 428 and 430 form an adjustable parallelogram linkage, as will be understood by one of skill in the art. Preferably, an identical parallelogram linkage exists on the opposing vertical wall of blocks 420 and 420', as shown in FIG. 55.

Anchor pivot 436 is secured to attachment 432, which is preferably fixed to cover 402. Platen pivot 434 is affixed to platen attachment 440, which is preferably pivotably attached to platen 410.

In a preferred embodiment, platen attachment 440 is provided with an upper cam shaped profile that is shaped and sized to follow the path of the lower inside edge of each of blocks 420 and 420'. Suitable cam shaped surfaces can be provided by either an annular, dome shaped element 440, or by providing one or more generally parallel planer elements having a cam shaped outer profile, as will be apparent to one of skill in the art. Provision of a cam surface which tracks the path of the lower inside edge of the blocks 420 and 420' operates to limit the extent to which the plane of platen 410 is permitted to deviate from its normal position which is generally parallel to the plane of the bottom plate 408. Preferably, the outer surface of the cam shaped portion of anchor 440 is sufficiently close to the path of travel of each of blocks 420 and 420' so that the tilt of the platen is limited no more than about 5%.

As a further option on the scissor embodiment of the present invention, a fluid level indictor 451 is provided. See FIG. 54. Fluid level indicator 451 generally comprises a linkage 452 which is pivotably connected to a moving portion of the scissor assembly, and also to the fluid level indicator 451. Level indicator 451 is preferably slidably mounted in a track 454 adjacent to scale (not illustrated) and calibrated such that the level indicator 451 and scale will indicate the remaining fluid volume.

After a medication bag 406 has been inserted into the base 404 and the base 404 engaged with the cover 402, the springs 412 and 412' are at their point of highest compression. As the springs 412 and 412' release force in a direction perpendicular to the axial direction of platen travel, the blocks 420 and 420' slide towards each other on spring guide 414, causing the medial ends of link arms 424, 426, 428 and 430 to move further apart in the axial direction. Through this mechanism the force exerted by the springs 412 and 412' is transmitted through the link arms 424, 426, 428 and 430 to the platen 410 through the platen attachment 440. The spring force component transmitted by the link arms 424, 426, 428 and 430 to the platen 410 increases throughout the dispensation cycle as the tension of the spring decreases so as to maintain a surprisingly substantially constant medication output pressure until the bag is substantially collapsed, as shown in FIG. 54. This surprising result shown in the experiments discussed infra is desirable in applications such as infusion of chemotherapy chemicals into a patient over a period of time at a constant rate. The mechanical advantage obtained by the link arms 424, 426, 428 and 430 compensates for the decrease in spring tension and the increase in the bag contact area over the dispensation cycle.

Experiment 1

Constructing the Pump

A platen was constructed in accordance with the embodiment illustrated in FIGS. 52–55, having springs 412 and 412' comprised of music wire having a wire diameter of approximately 0.085 inch. Springs 412 and 412' had an outside diameter of about 0.5 inches, a spring constant of approximately 111 lbs. per inch, and were approximately 1.7 inches long in the uncompressed state and approximately 0.9 inch long in the fully compressed state, as shown in FIG. 54. The sum of the axial travel of springs 412 and 412' was approximately 0.7 inch between the compressed state as shown in FIG. 53 at the beginning of the dispensation cycle and the state shown in FIG. 54 at the end of the dispensation cycle. The springs were preloaded to about 35 lbs. on each side, and were measured to generate a total spring force of about 160 lbs. Blocks 420 and 420' were constructed from available from DuPont. The length of each of the four link arms was about 0.8 inches from pivot to pivot. The platen and opposing wall were substantially flat to isolate the pressure effects due to the spring biasing assembly.

Experiment 2

Testing the Platen Pump

A 50 cc medication bag 406 was inserted in the platen pump of Experiment 1 and the output fluid pressure from the medication bag 406 was measured as the volume in the medication bag 406 decreased over the dispensation cycle. Table I below illustrates the data accumulated from this experiment.

TABLE I

| Volume Expelled from Medication Bag (cc) | Output Fluid Pressure (psi) |
| --- | --- |
| 0 | 5.0 |
| .5 | 5.0 |
| 1 | 5.0 |
| 2 | 5.0 |
| 3 | 5.0 |
| 4 | 5.0 |
| 5 | 5.0 |

TABLE I-continued

| Volume Expelled from Medication Bag (cc) | Output Fluid Pressure (psi) |
| --- | --- |
| 10 | 5.0 |
| 15 | 5.05 |
| 20 | 5.1 |
| 25 | 5.1 |
| 30 | 5.1 |
| 35 | 5.1 |
| 40 | 4.95 |
| 42.5 | 4.6 |
| 45 | 4.45 |
| 46 | 4.25 |
| 47 | 4.1 |
| 47.5 | 9.0 |
| 48 | 3.9 |
| 48.5 | 3.5 |
| 49 | 2.4 |
| 50 | 0 |

Figure 56:
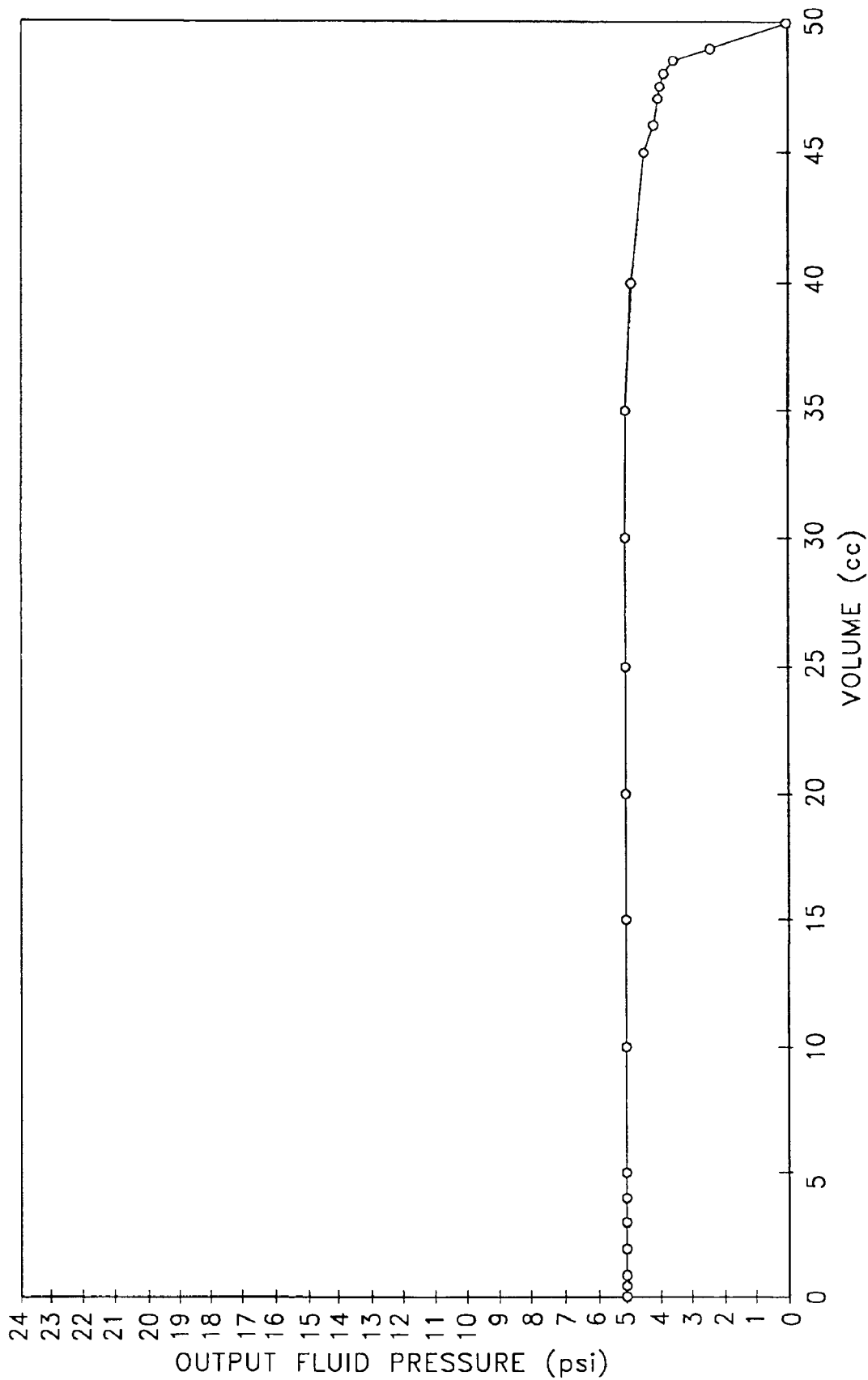
FIG. 56 is a plot of fluid pressure versus volume.
Figure 57:
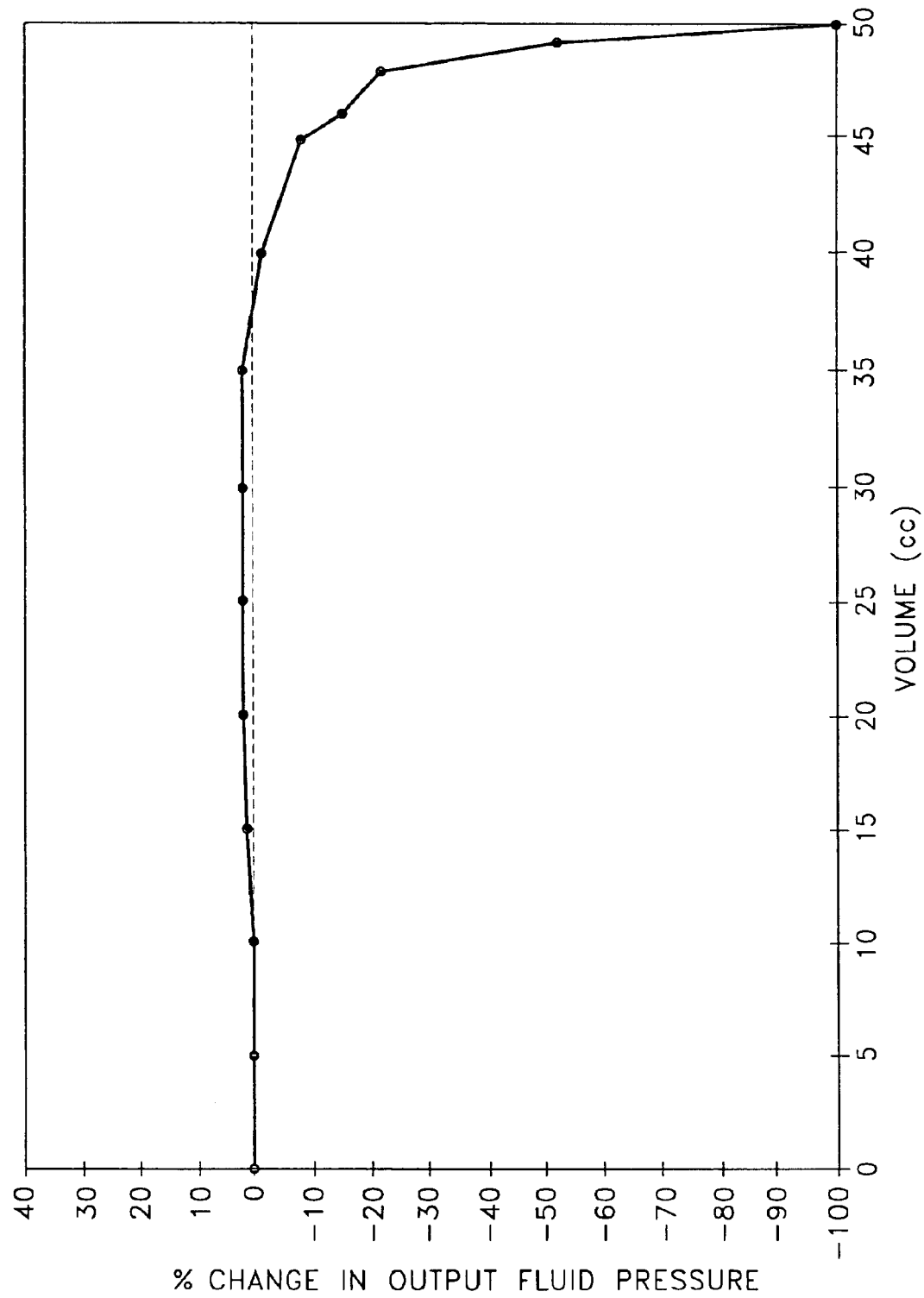
FIG. 57 is a plot of percent change in pressure versus volume.

The data obtained from the above experiment is reproduced in FIG. 56, which plots the volume of the medication dispelled in cubic centimeters versus the output pressure in lbs/sq. in. The percent change in output pressure versus the volume expelled is illustrated in FIG. 57 illustrates the remarkably steady output pressure of the medication contained in medication bag 406 during the dispensation cycle produced by the platen pump 400.

Experiment 3

100 cc Volume Test

In Experiment 3, the 50 cc medication bag 406 was replaced with a 100 cc medication bag. The experiment conducted in Experiment 2 above was repeated and the following data recorded.

TABLE II

| Volume Expelled from Medication Bag (cc) | Output Fluid Pressure (psi) |
| --- | --- |
| 0 | 5.1 |
| 5 | 4.6 |
| 10 | 4.7 |
| 20 | 4.75 |
| 30 | 4.75 |
| 40 | 4.6 |
| 50 | 4.55 |
| 60 | 4.4 |
| 70 | 4.2 |
| 80 | 3.95 |
| 90 | 3.6 |
| 95 | 3.4 |
| 99 | 2.9 |
| 100 | 0 |

Figure 58:
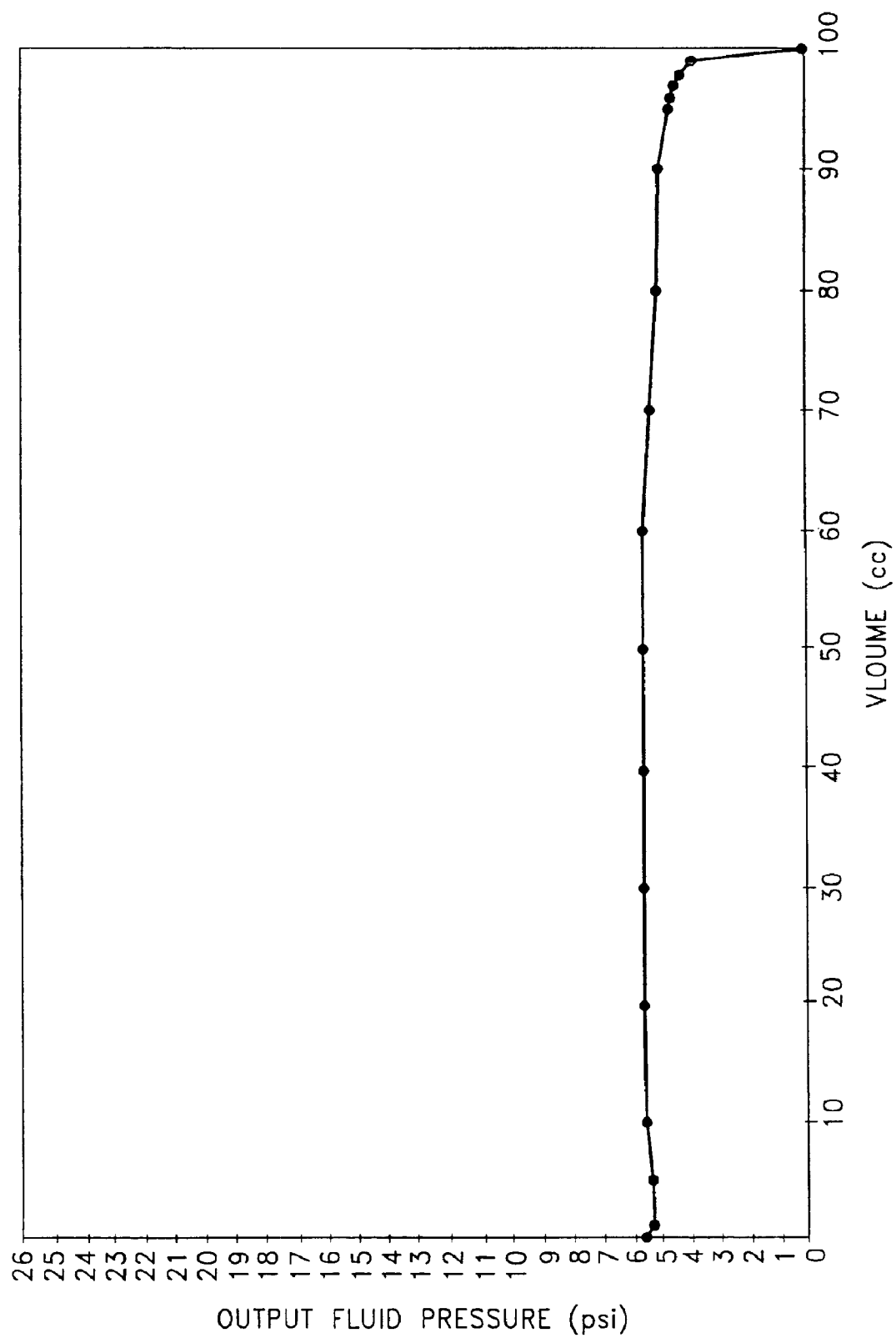
FIG. 58 is a plot of fluid pressure versus volume.
Figure 59:
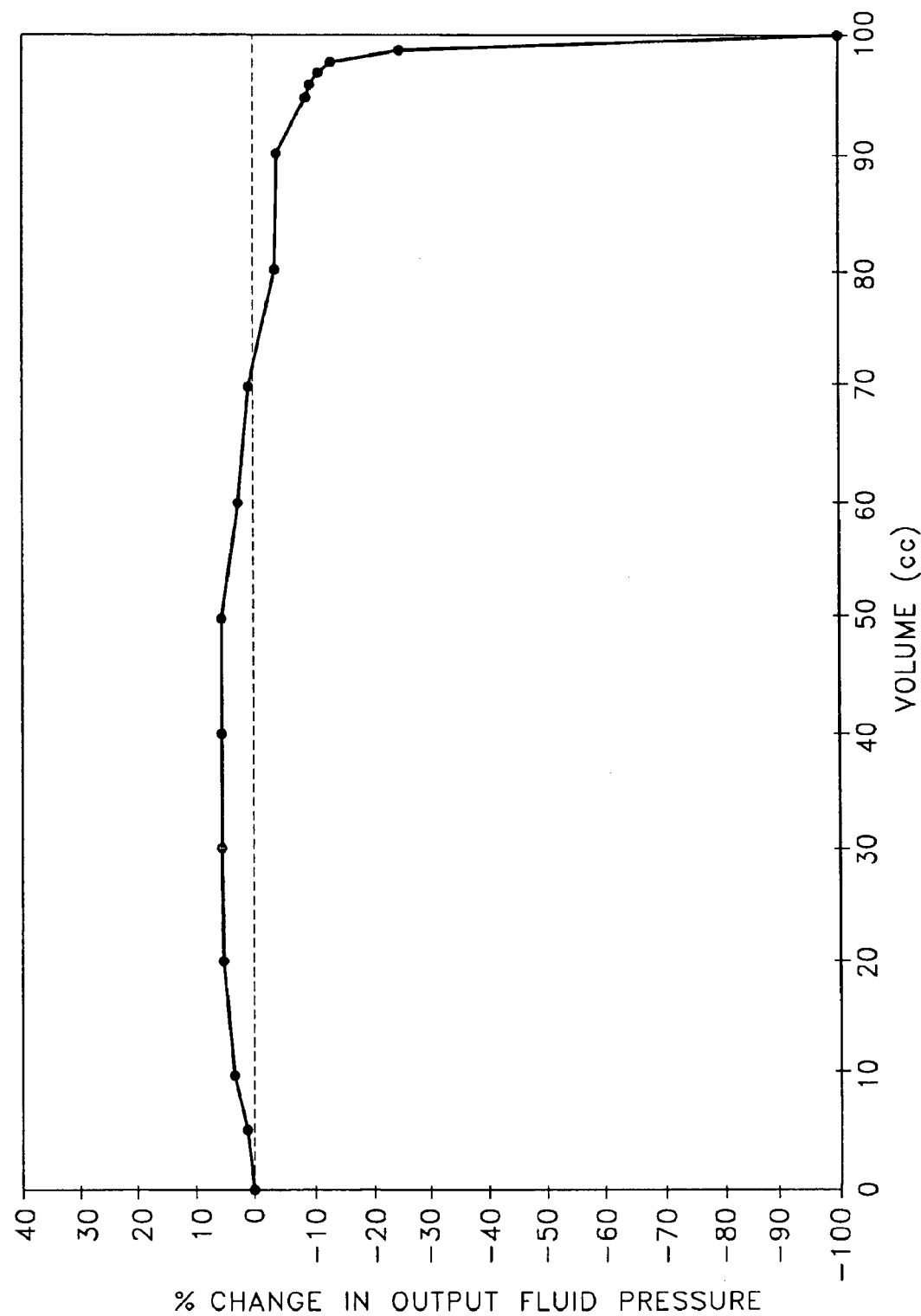
FIG. 59 is a plot of percent change in pressure versus volume.

FIG. 58 illustrates the output pressure over the dispensation cycle. FIG. 59 illustrates the percent change in pressure over the dispensation-cycle.

Increasing the volume of medication in the medication bag 406 from 50 cc to 100 cc remarkably did not dramatically affect the change in pressure over the dispensation cycle on the medication bag 406.

Referring to FIGS. 61–65, a fluid container 500 is provided which may be readily used with any of the previously disclosed embodiments of the platen pump. Preferably, the fluid container 500 consists of a collapsible medication reservoir or bag 510 in fluid communication with an effluent fluid line 530. The effluent fluid line 530 may lead to an administration set 540 shown in phantom in FIG. 61. An administration set is also shown in FIG. 7. The effluent fluid line 530 may be standard PVC tubing or other material known to those skilled in the art.

Preferably, the medication reservoir 510 has a first surface 508 and a second generally opposing surface 509. The first surface 508 and second surface 509 each have a substantially planar central portion 512 and 513. In a medication reservoir having a diameter of about 3.5 inches, the generally planar central portions 512 and 513 typically have a diameter in the range of from about 1.5 inches to about 3.0 inches, and preferably from about 2.4 inches to about 2.8 inches in the fully filled configuration.

Figures 61, 62:
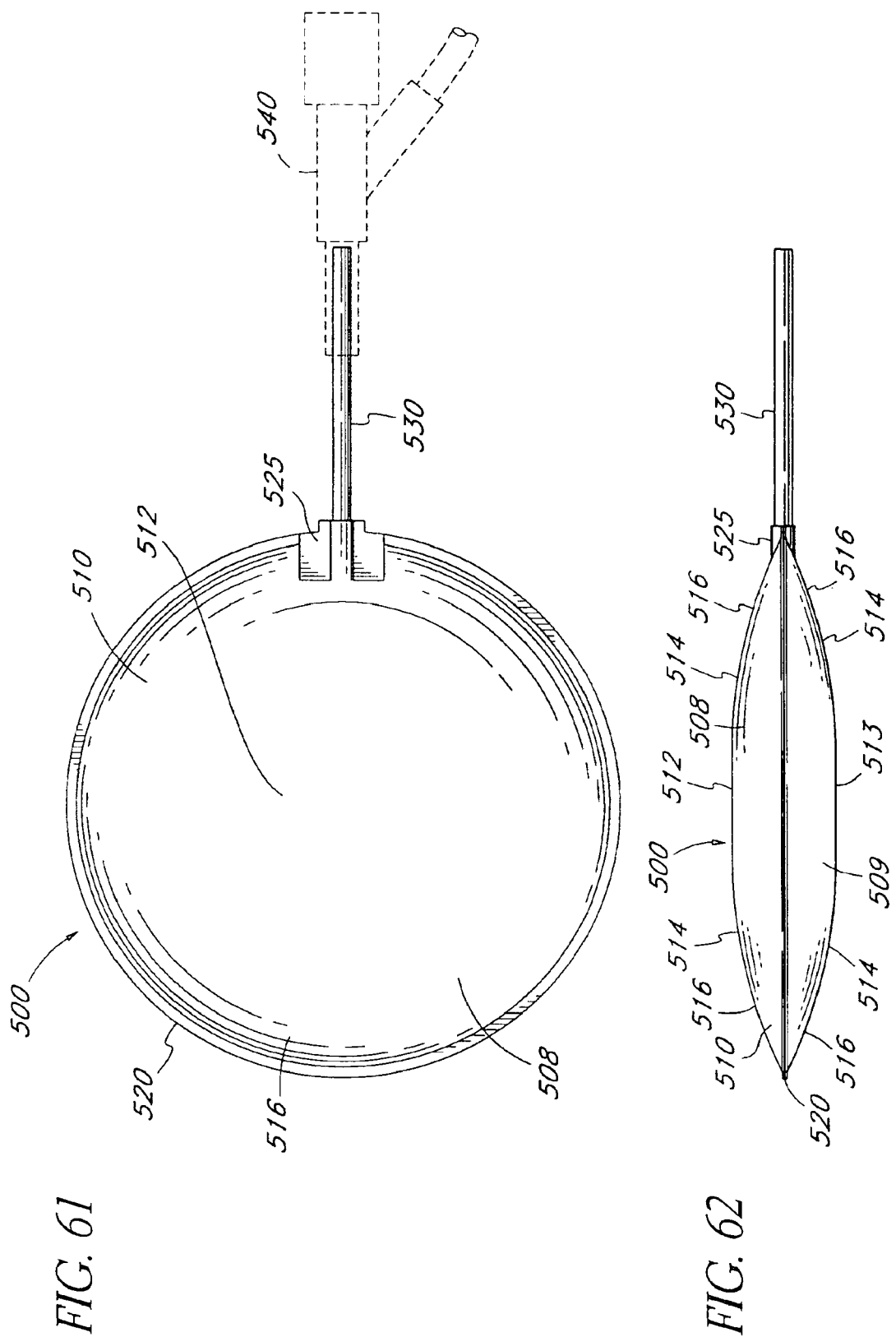
FIG. 61 is a top plan view of the fluid container embodying the present invention.
FIG. 62 is a left side view of the fluid container of FIG. 61.

A transition portion 514 surrounds the circular central portions 512 and 513 of the first surface 508 and second surface 509. Transition portion 514 comprises the portion of the surface of the reservoir 510 which deviates from the plane of first surface 508 or second surface 509. Thus, transition 514 joins the flat circular central portions 512 and 513 with radially exterior-most sloping portions 516 when the medication reservoir 510 is full as shown in FIG. 62.

The radially exterior-most opposing sloping portions 516 are preferably joined at seam 520. By "seam" the present invention also contemplates the outer peripheral edge of a "seamless" bag such as may be produced through any of a variety of molding or other plastic forming techniques known in the art.

The first surface 508 and second surface 509 are preferably formed from two sheets of a suitably bondable, inelastic material which exhibits suitable stability in the presence of the intended medication. The two sheets may be joined at seam 520 with the use of any of a variety of joining techniques, such as thermal bonding, solvent bonding, adhesives or by a radio frequency weld. Preferably, the medication reservoir is constructed from a PVC in U.S. Class 6 adequate for the delivery of drugs to a patient although other materials known to those of skill in the art are available and may be used.

Figure 63:
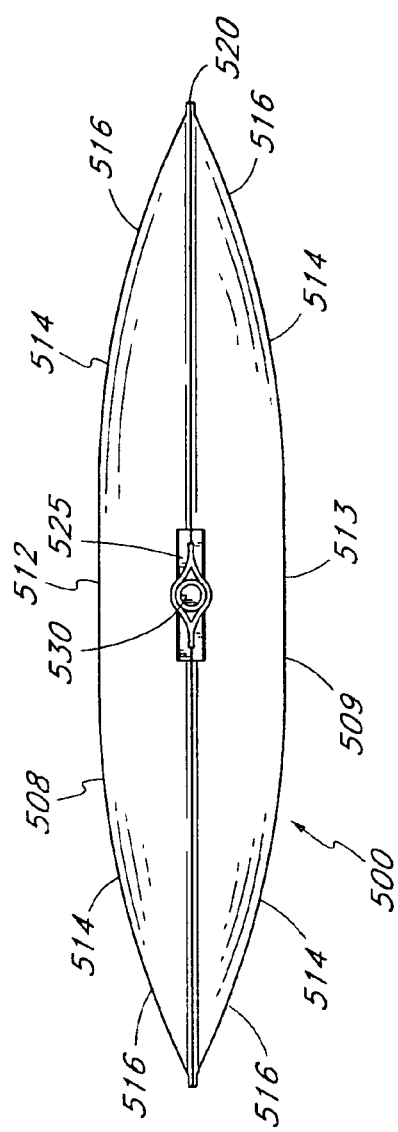
FIG. 63 is a front view of the fluid container of FIG. 61.
Figure 64:
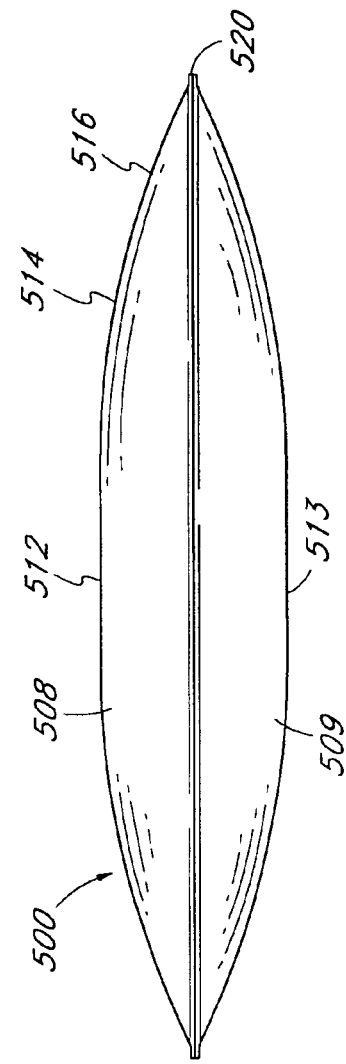
FIG. 64 is a rear view of the fluid container of FIG. 61.
Figure 65:
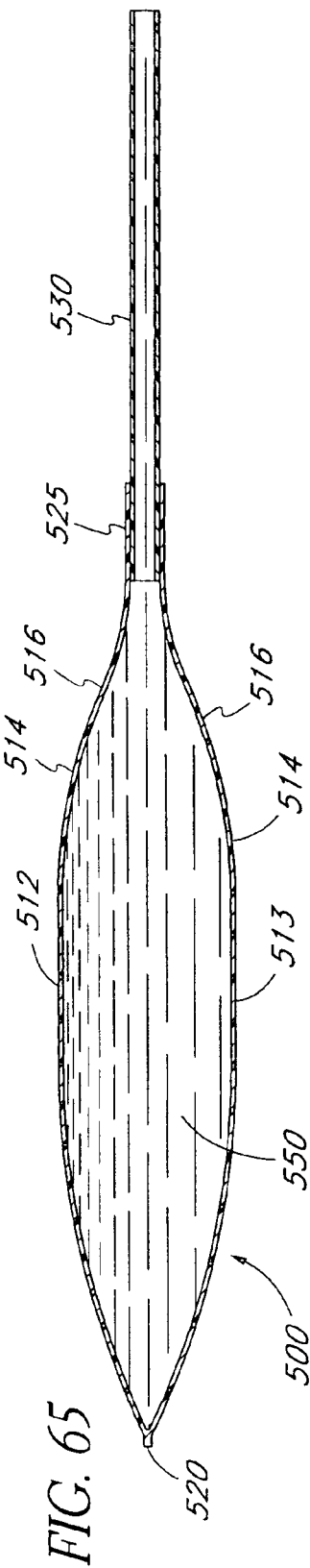
FIG. 65 is a left side cross-sectional view of the fluid container of FIG. 61 when full of fluid.
Figures 84, 85:
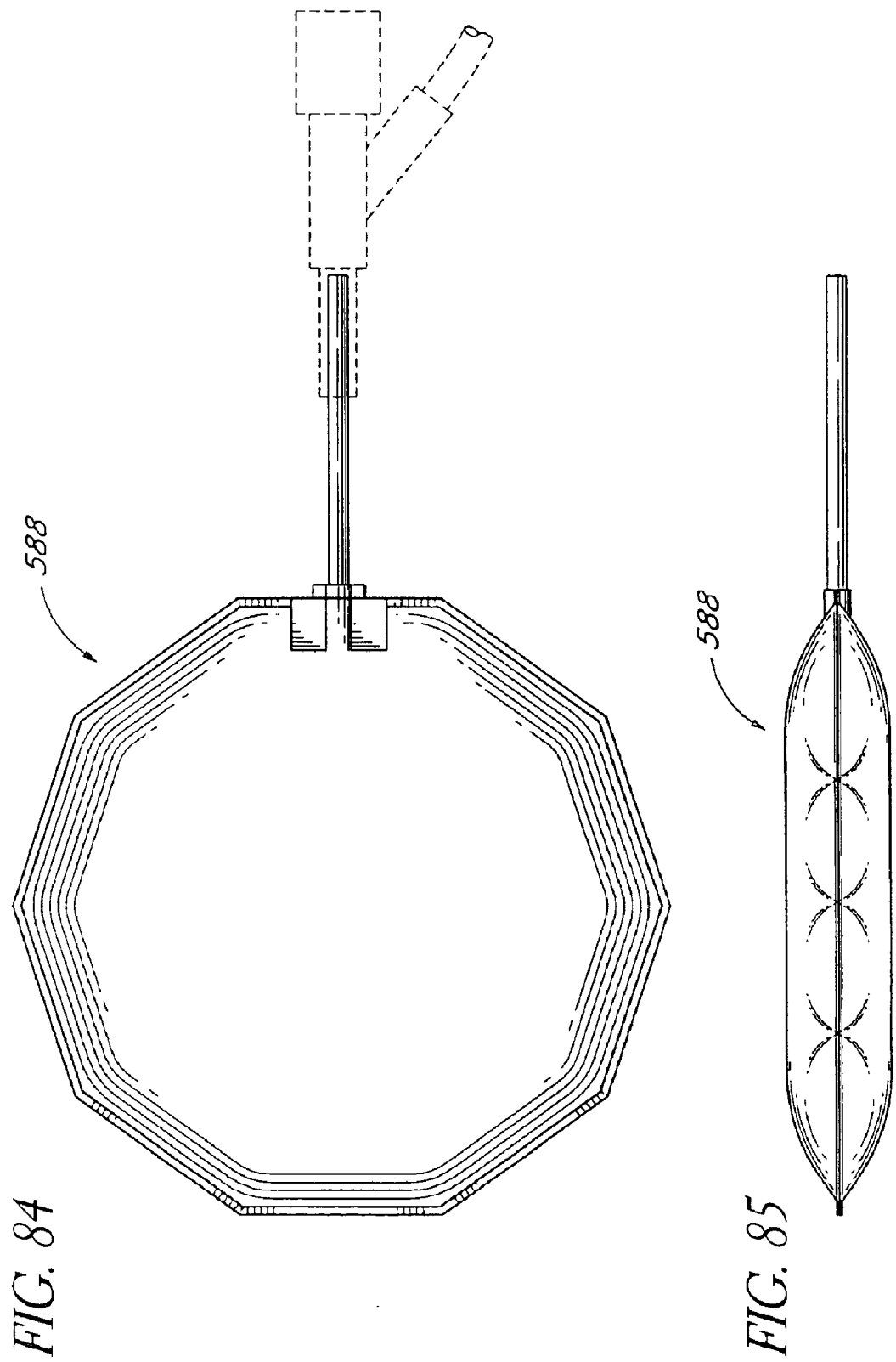
FIG. 84 is a top plan view of another alternative embodiment of the fluid container shown in FIG. 61.
FIG. 85 is a left side view of the alternative embodiment shown in FIG. 84.
Figure 88:
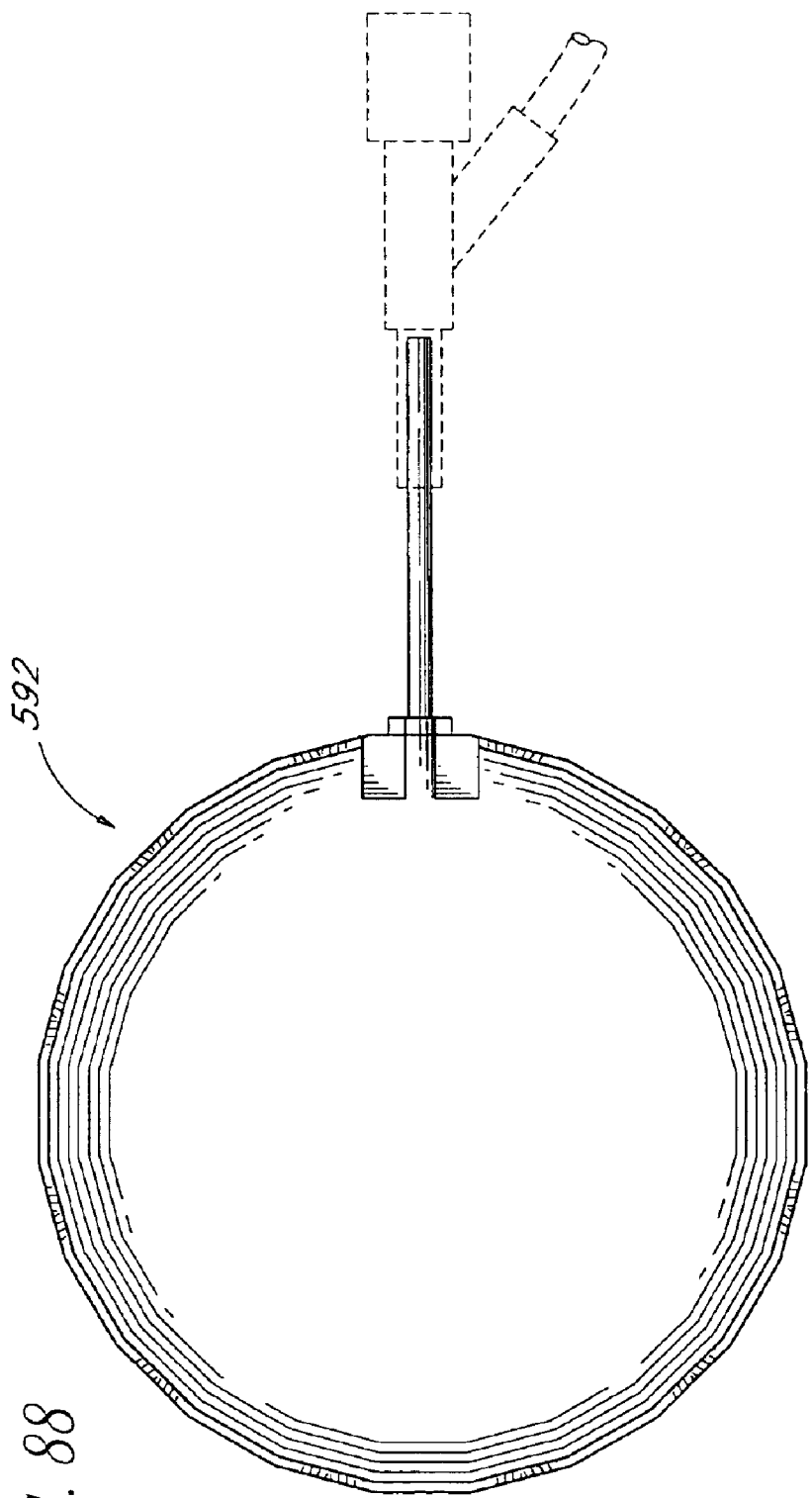
FIG. 88 is a top plan view of another alternative embodiment of the fluid container shown in FIG. 61.
Figure 89:
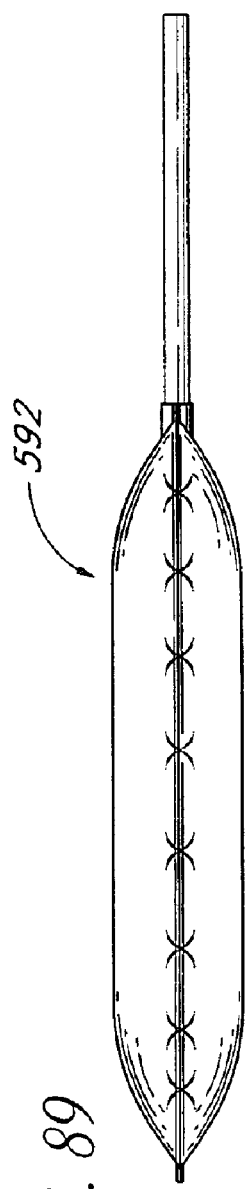
FIG. 89 is a left side view of the alternative embodiment shown in FIG. 88.

As shown in FIGS. 63 and 65, the effluent fluid line 530 may be joined to the medication reservoir 510 through the use of a radio frequency weld or other bond at a joint 525. Other means for joining the medication reservoir 510 and the effluent fluid line 530, such as thermal bonding, solvent bonding, adhesives or friction couplings will be readily apparent to those of skill in the art.

Preferably, the medication reservoir 510 shown in FIGS. 61–65 has a diameter within the range of from about 3.5 inches to about 5 inches and a height within the range of from about 0.5 inches to 1.0 inches. In general, the diameter of the bag is influenced by the type of compression mechanism used. For example, in the threaded clam shell embodiment of FIG. 1, a bag having a diameter of much greater than about four inches would require a pump having too big a diameter to be conveniently grasped by many patients. Other compression mechanisms, however, can be readily used with 5 inch, 6 inch, or larger diameter bags. The height, or thickness of the bag is typically governed by the desired volume and the maximum desired diameter.

For many applications of the present invention, the fluid container 500 preferably contains 50 cc of fluid. Although these volumes are preferred in the present invention, other sizes of fluid containers may be easily constructed using the disclosure of the present invention. These varying size fluid containers are contemplated by this disclosure.

An important aspect of the fluid container 500 is that it is able to withstand pressures applied to it by the platen pump disclosed herein. Further, preferably the fluid container 500 is relatively inelastic in order to minimize the change in pressure on the fluid by the platen pump. Advantageously, the disc like configuration of the present embodiment of the fluid container 500 results in substantially even pressure distribution throughout seam 520 when the medication reservoir 510 and effluent fluid line 530 are in the dispensation cycle. As discussed above, this uniform pressure distribution minimizes the buildup of localized stresses which could lead to a rupture of the container 500.

Another advantage of the fluid container 500 is that a plurality of filled fluid containers 500 may be easily stored such as in a refrigerator in a stacked configuration. Further, when the fluid containers 500 are empty, the volume required to dispose of them is very small because the fluid containers 500 are flat and flexible when empty.

In addition to a fluid container with a circular outer profile, other shaped reservoirs may be constructed in accordance with the disclosure of the present invention. For example, referring to FIGS. 66–69, a square medication reservoir 560 having a generally planar square top surface 562 and bottom surface 563 may be used in connection with the various embodiments of the platen pump. In a similar fashion to the circular medication reservoir, the top and bottom surfaces of the square medication reservoir 560 have generally square flat central portions, transition portions 564 and radially exterior-most sloping portions 566. Preferably, a high frequency weld is used to join seam 572 and attach the medication bag 560 to the effluent fluid line 570 at a joint 568.

Referring to FIGS. 70–73, a diamond-shaped fluid reservoir 561 may be provided. Further, a hexagonal fluid reservoir 580 and 581 (FIGS. 74–81) with a joint 582 on one of the sides of the hexagonal medication reservoir 580 (FIGS. 74–77) or a joint 583 at one of the corners of the hexagonal medication reservoir 581 (FIGS. 78–81) may be provided. Referring to FIGS. 82–89, fluid containers having medication reservoirs with eight sides (586), ten sides (588), twelve sides (590) or twenty-four sides (592) may be provided.

Figure 90:
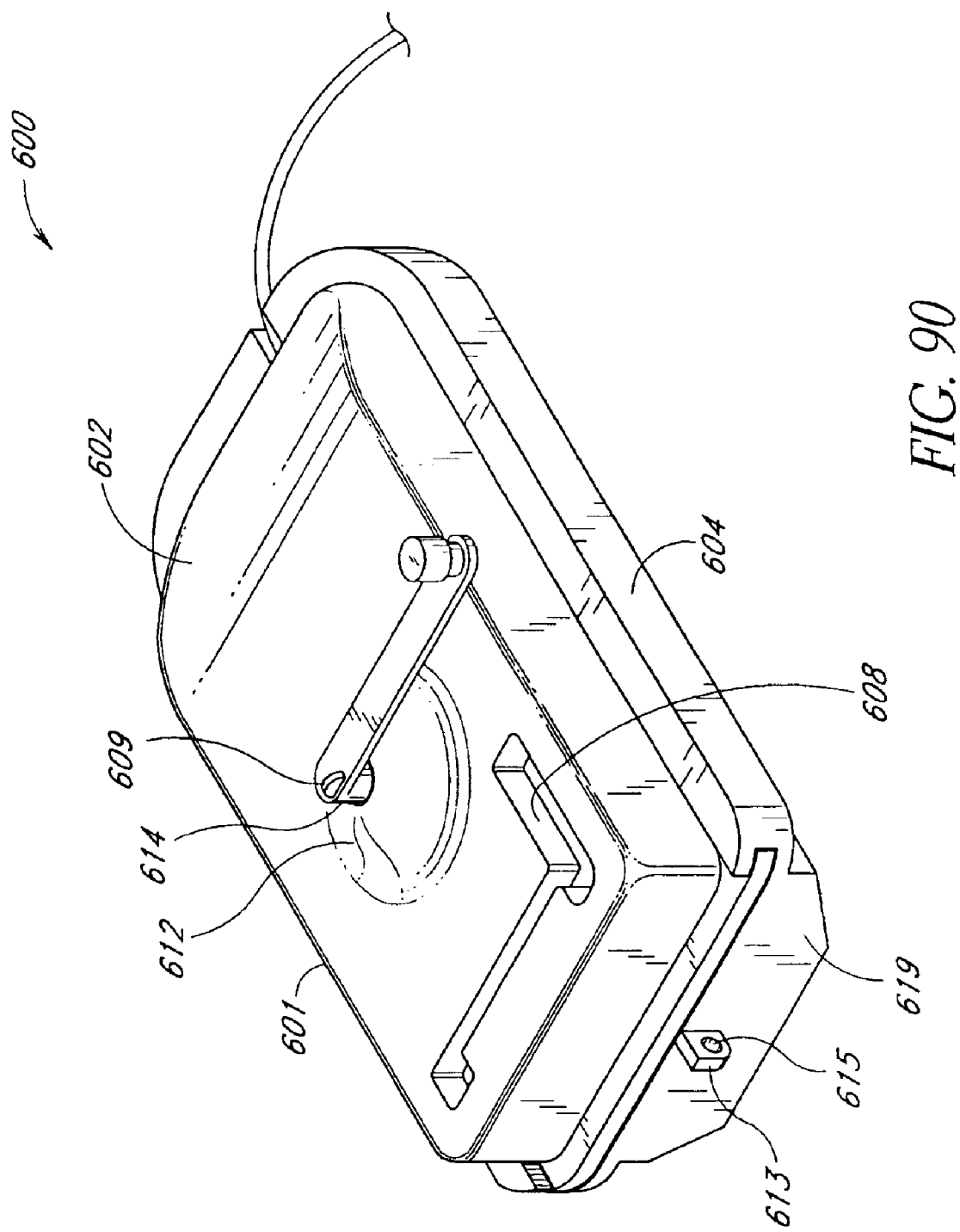
FIG. 90 is a perspective view of an alternative embodiment of the platen pump.

In a further embodiment, the present invention includes a platen pump designed for use with rectangular medication bags. Referring to FIG. 90, the pump 600 comprises a housing 601 formed from a cover 602 and a base 604. The cover 602 and base 604 are preferably formed in accordance with conventional techniques for the production of medical device housings, such as injection molding of thermoplastic or thermoset polymers. Alternatively, any of a variety of other techniques may be utilized, including fabrication from sheet metal stock, as will be well understood by one of skill in the art.

A handle storage recess 608 may be formed in the cover 602 during fabrication. As will be described below, a handle 610 is used to raise and lower the platen in the pump 600. When the platen is applying force to a medication bag (not shown), the handle 610 preferably separates from the pump 600. The handle 610 can be inserted into the handle storage recess 608, providing a convenient location to store the handle 610 when not in use. A lift tab 609 may be included on the handle 610. The lift tab 609 provides assistance to the user in removing the handle 610 from the handle storage recess 608.

The cover 602 also may contain a ridge 612. In one embodiment, the ridge 612 is formed as a mound with an aperture 614 in the center of the ridge 612 for insertion of the handle 610. However, other configurations for the ridge 612 are contemplated as will be easily understood by those of skill in the art. A portion of the handle 610 is preferably spaced above the cover 602 in operation, thereby allowing a user to turn the handle 610 without interference from the cover 602.

A connecting tab 613 may be located on a face 619 of the base 604. The connecting tab 613 includes an aperture 615. Because the pump 600 is designed to be carried over an extended period of time by the patient, the connecting tab 613 provides a convenient way to tote the pump 600. A split ring, string or other material can be placed through the aperture 615 in the connecting tab 613. The pump 600 can then be secured to an I.V. pole or a patient. Of course, the connecting tab 613 may be integral with the cover 602. In addition, other connecting means may be used to assist a patient in transporting the pump 600.

Figure 91:
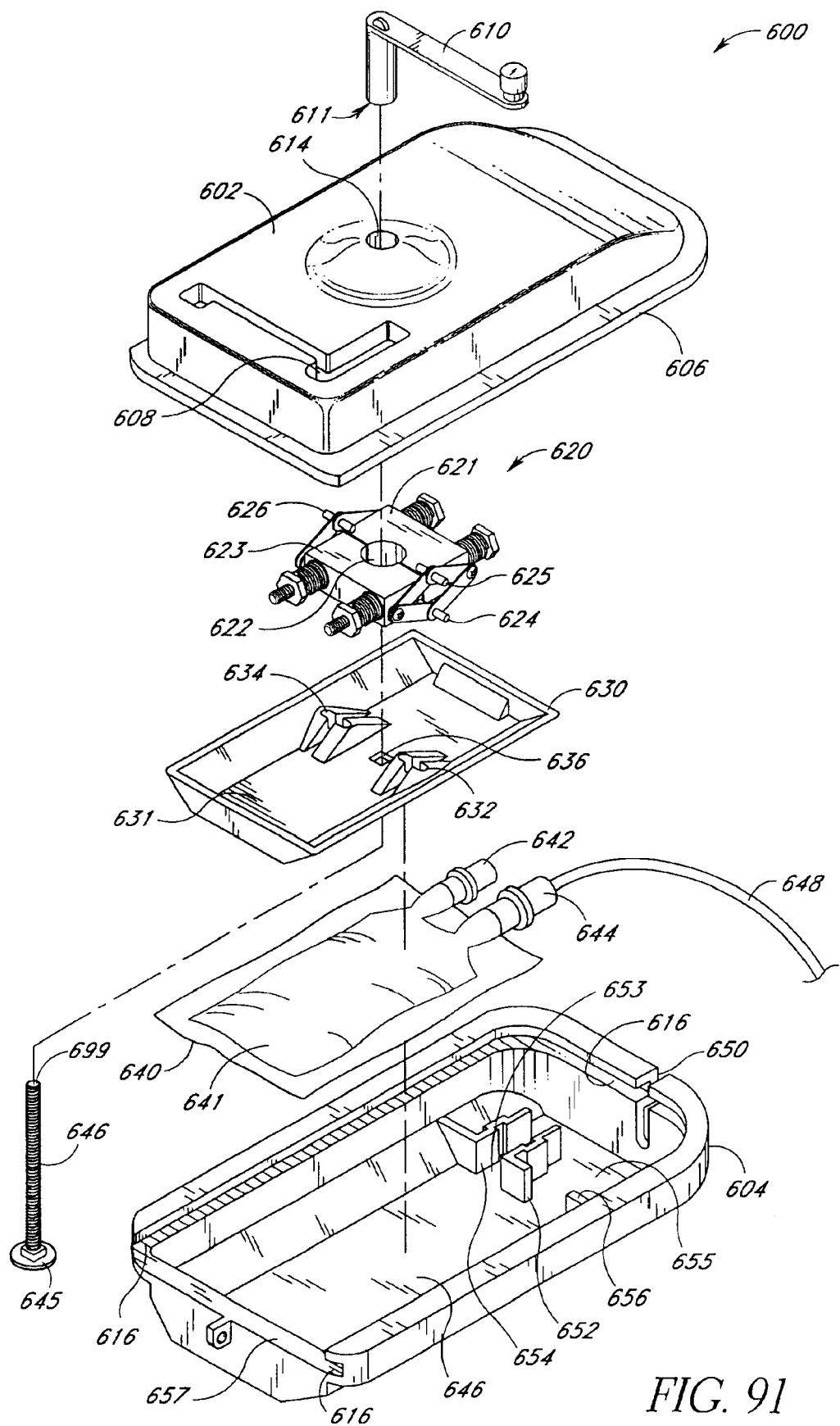
FIG. 91 is an exploded perspective view of the alternative embodiment shown in FIG. 90.

FIG. 91 shows an exploded view of the pump 600. The pump 600 includes the cover 602, the handle 610, a spring and linkage assembly 620, a platen 630, a connecting bolt 645 and the base 604. A rectangular medication bag 640 is inserted into the base 604 during pump 600 operation to provide a medication reservoir.

The cover 602 has an outer rim 606. This outer rim 606 slidably engages a corresponding groove 616 in the base 604. When the rim 606 of the cover 602 is inserted into the groove 616 of the base 604, the base 604 and cover 602 cooperate to form a chamber 646 for containing the functional components of the infusion device and the medication bag 640. Alternatively, the base 604 may contain a rim and the cover 602 may contain a groove for slidable engagement of the cover 602 and the base 604.

Figure 92:
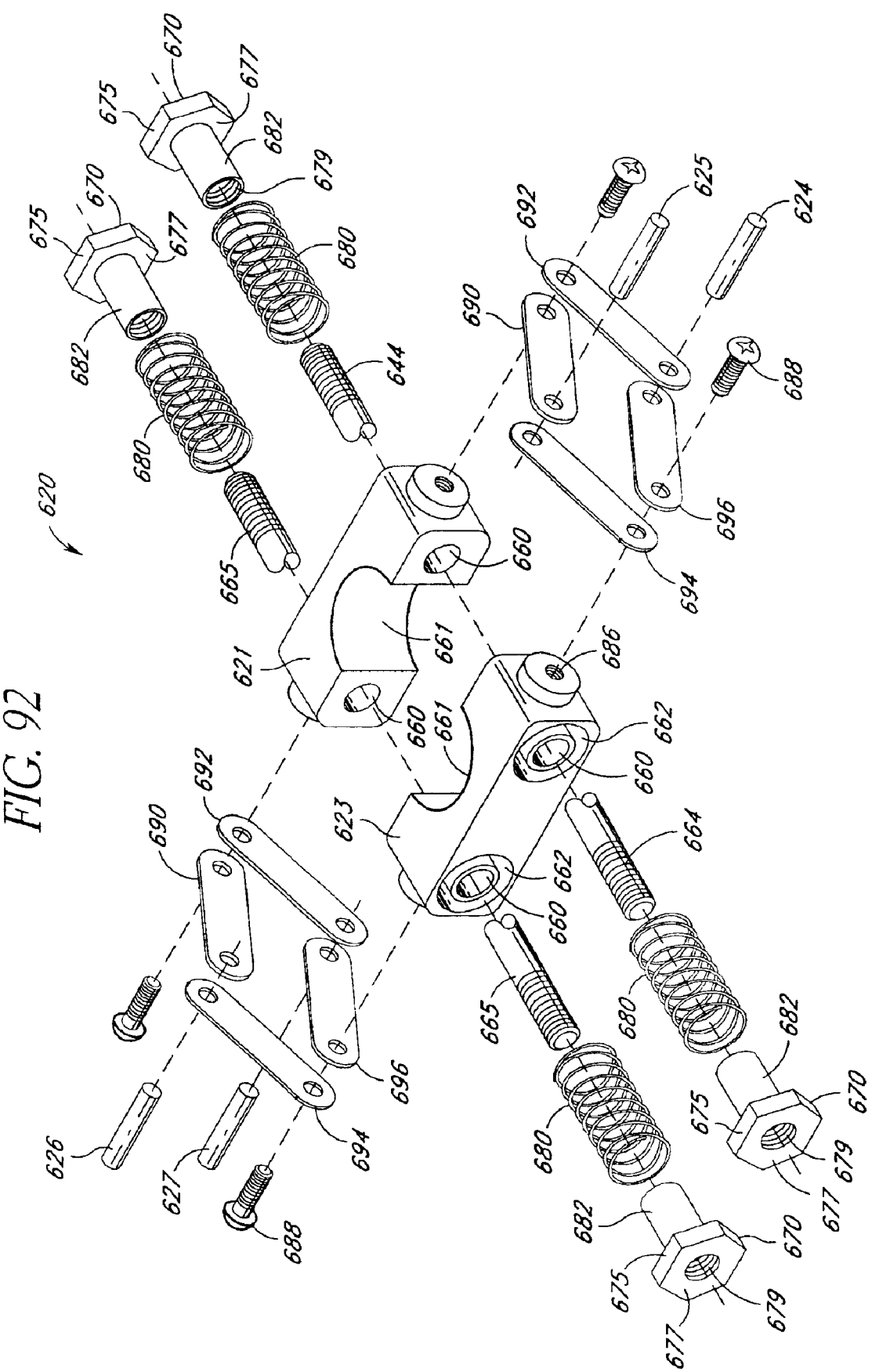
FIG. 92 is an exploded view of the scissor-type biasing means shown in FIG. 91.

In the illustrated embodiment, the spring and linkage assembly 620 is connected between the platen 630 and the cover 602. The spring and linkage assembly 620 contains connector bars 624–627 (FIG. 92). A pair of bar receivers 632 and 634 are formed on the top side 631 of the platen 630. The connector bars 624 and 627 insert in the bar receivers 632 and 634. A corresponding pair of bar receivers (not shown) are located on a bottom side of the cover 602. The connector bars 625 and 626 insert in the bar receivers of the cover 602. This connection secures the spring and linkage assembly 620 between the platen 630 and the cover 602.

As shown in FIG. 91, the connecting bolt 645 is preferably inserted through an aperture 636 in the platen 630, through an aperture 622 formed by movable blocks 621 and 623 and through the aperture 614 in the cover 602. A threaded bore 611 of handle 610 has threads corresponding to threads 646 on the connecting bolt 645. The threads in the handle 610 engage with the threads 646 on the bolt 645 allowing movement of the platen 630 via the spring and linkage assembly 620 upon turning the handle 610, as will be described below. When the handle 610 is fully engaged with the bolt 645, the pump 600 is in an open position. When the pump 600 is in the open position, the platen 630 is fully stored within the cover 602. This allows the cover 602 to separate from the base 604 without interference from the platen 630. As the handle 610 is turned to separate the handle 610 from the bolt 645, the platen 630 begins to lower into the base 604 via the spring and linkage assembly 620.

The medication bag 640 is preferably in fluid communication with the patient by way of an effluent fluid line 648, which extends through the base 604 by way of a port 650. Modification of the port 650 to accommodate the various relationships between the cover 602 and base 604 will be apparent to one of skill in the art. A flow regulator (not illustrated) to regulate the flow of medication may be provided on fluid line 648.

In general, the medication bags 640 contemplated for use in accordance with this embodiment of the present invention are standard medication bags well known and used in the art. Standard bags are currently produced by Abbott Laboratories and Baxter Healthcare. However, medication bags adapted for use in the pump 600 can be readily produced in accordance with the disclosure herein. The medication bags 640 include a fluid reservoir segment 641, an injection port 642 and a fluid delivery port 644.

When delivering medication from a medication bag 640 to a patient, only the fluid reservoir segment 641 is compressed by the platen 630. The injection port 642 and the fluid delivery port 644 are generally not compressed. The platen 630 is approximately the same size as the fluid reservoir segment 641 of the medication bag 640. To protect both the injection port 642 and the fluid delivery port 644 of the medication bag 640, the base 604 preferably contains walls 652, 654 and 656 forming two compartments 653 and 655. The injection port 642 fits inside compartment 653 and the fluid delivery port 644 fits inside compartment 655. When the medication bag 640 is inside the pump 600, the injection port 642 and the fluid delivery port 644 are protected by compartments 653 and 655. Only the fluid line 648 is exposed from the pump 600.

Figure 93:
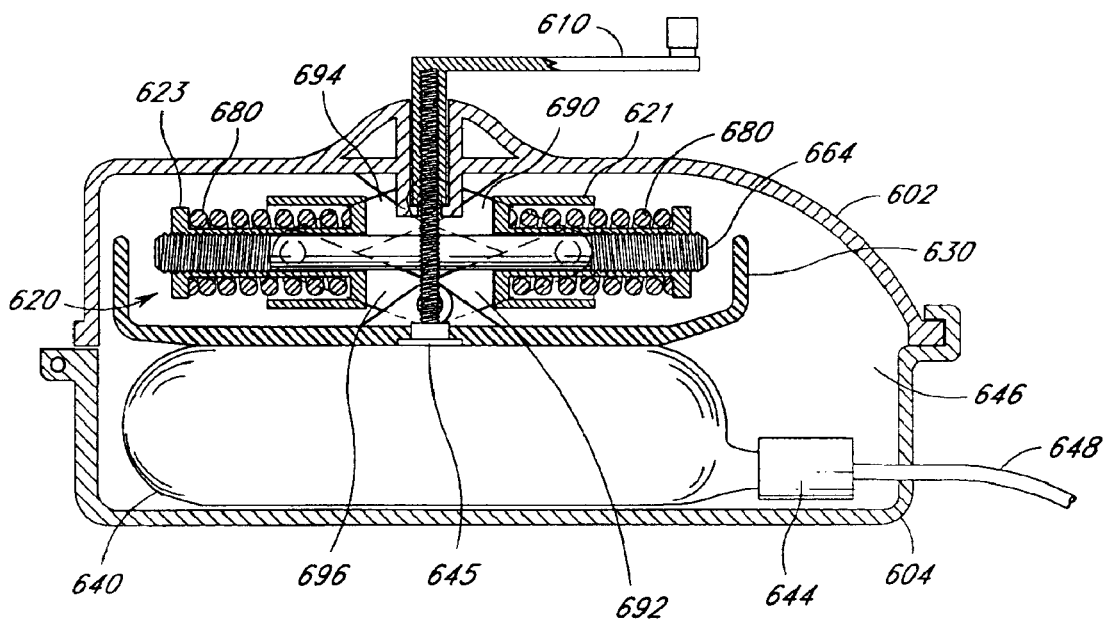
FIG. 93 is a cut-away side view of the alternative embodiment shown in FIG. 90 with the platen in a first position.
Figure 94:
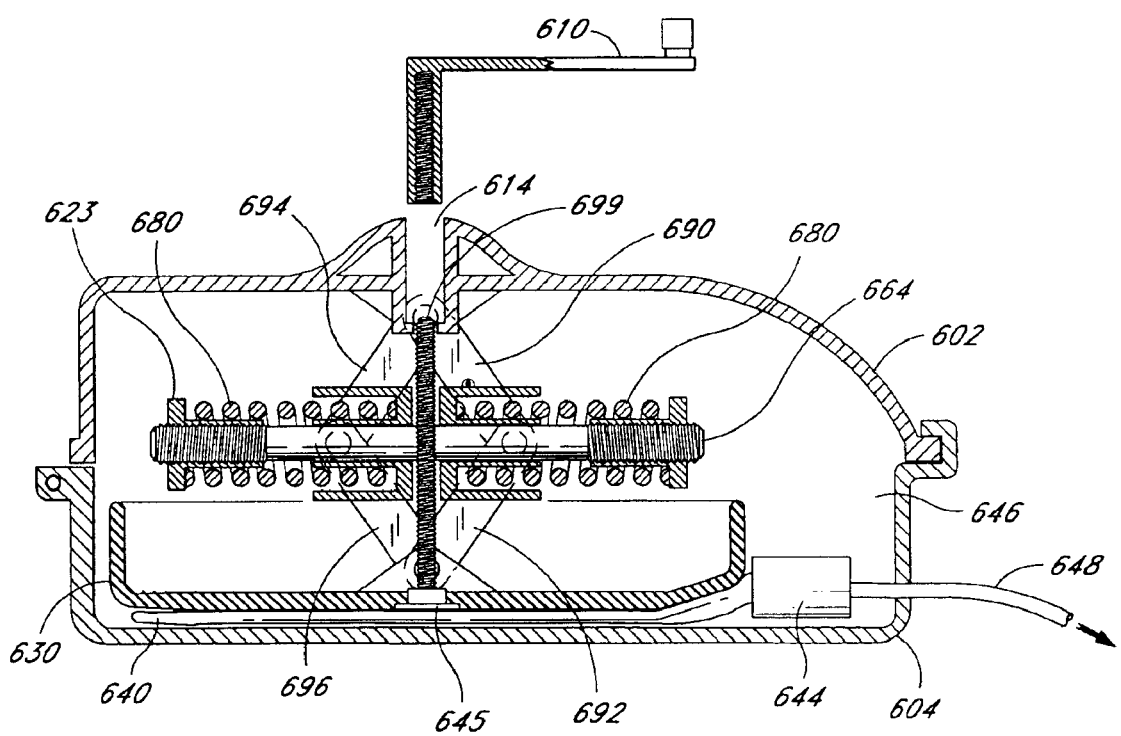
FIG. 94 is a cut-away side view of the alternative embodiment shown in FIG. 90 with the platen in a second position.

Referring to FIGS. 92, 93 and 94, the platen 630 exerts a force on the medication bag 640 through the spring and linkage assembly 620. In general, the spring and linkage assembly 620 comprises one or more biasing elements having a longitudinal axis which extends at an angle with respect to the longitudinal axis of travel of the platen 630. Preferably, the biasing element axis extends approximately at about a perpendicular to the axis of travel of the platen 630. As discussed below, the biasing element preferably comprises one or more pairs of springs having at least one spring guide such as a central shaft or tubular cover. Because the pump 600 in the preferred embodiment is designed to be portable, it is desirable to manufacture the pump as thin and small as possible. To reduce the overall height of the pump 600, two pairs of springs are preferably used as the biasing element. The use of two pairs of springs has several advantages. First, the same force is applied using springs and guides of half the diameter of a single pair of springs. Using springs of a smaller diameter allows the overall height of the pump 600 to decrease. Second, the lateral spacing of the springs assists in providing a balanced force to the platen 630. By applying a balanced force, the platen 630 will lower into the base 604 with a minimum of rocking.

In the illustrated embodiment, a pair of spring guides 664 and 665 extend along an axis which is generally perpendicular to the direction of travel of the platen 630. The spring guides 664 and 665 comprise a metal rod having a length within the range of from about 3 inches to about 5 inches, and a diameter from about 0.125 inch to about 0.250 inch, although variations will be readily apparent to one of skill in the art.

In an embodiment in which the spring guides 664 and 665 comprise a unitary or segmented shaft having a continuous thread extending throughout its length, a tubular sleeve may be conveniently disposed over the portions of the threaded shaft which will slidably carry other moving parts, as will be discussed. Alternatively, the spring guides 664 and 665 can be constructed from a generally smooth rod, having a threaded region only on the distal ends thereof for receiving a nut 670.

A spring stop 675 is carried at either end of the spring guides 664 and 665. As will be readily apparent to one of skill in the art, any of a variety of means can be utilized for retaining a spring under tension. For example, a nut or nut and washer threadably engaged to the spring guides 664 and 665 is convenient, both from a manufacturing standpoint and due to the ability of the manufacturer to adjust the spring tension by simply rotating the nut. To avoid rotation of the stop 675 on the spring guides 664 and 665, epoxy may be used as will be readily understood by those skilled in the art.

In the illustrated embodiment, a spring stop 675 is provided on each lateral end of the spring guides 664 and 665 for limiting the expansion of each spring 680. The spring stops 675 generally comprise a radially outwardly extending annular flange 677 and have an aperture 679 extending therethrough for receiving a threaded portion of the spring guides 664 and 665. The spring stop 675 also has a cross-sectional area sufficient to limit expansion of the spring. The spring stop 675 is preferably provided with an axially extending tubular sleeve 682, which in the assembled pump extends along the spring guides 664 and 665 and within the spring 680. In the illustrated embodiment, the sleeves 682 have internal threads complementary to the threads on the spring guides 664 and 665 to securely threadably retain the spring stop 675 in place.

In an alternate embodiment (not illustrated), the spring stop 675 comprises the annular flange 677 and the tubular sleeve 682 as in the foregoing embodiment. However, the spring stop 675 is held in place by a separate threaded nut secured directly to the spring guides 664 and 665. In this embodiment, the internal thread on the aperture 679 and the interior wall of the tubular sleeve 682 is unnecessary. Although the use of a separate threaded nut is convenient from a manufacturing standpoint, it adds to the overall lateral length of the spring guides 664 and 665, which may be undesirable in a given embodiment.

The springs 680 are compressed between the spring stops 675 and two moveable stops 621 and 623. In one embodiment, the springs 680 comprise music wire having a wire diameter of approximately 0.80 inch. Lower diameters such as 0.062 inch may also be used by increasing the preload.

Preferably, the springs 680 have a spring constant within the range of from about 80 lbs. per inch to 90 lbs. per inch in a dual spring embodiment. Each spring 680 is approximately 1.62 inches long in its un-compressed state and approximately 0.90 inches long in its fully compressed state, shown in FIG. 93, and 0.50 inch in diameter. The sum of the axial travel of springs 680 is approximately 0.90 inch between the compressed state as shown in FIG. 93 at the beginning of the dispensation cycle and the state shown in FIG. 94 at the end of the dispensation cycle. Depending on the spring constant chosen, the dispensation cycle can vary from one half hour to eight days. These dimensions correspond to a pump for a 100 cc medication bag. For larger or smaller medication bags dimensions would vary as will be easily recognized by those of skill in the art.

Moveable stops 621 and 623 function as medial spring abutments to mechanically link the medial travel of the spring 680 to the linkage assembly 620 and platen 630. Referring to FIG. 92, the stops 621 and 623 are generally rectangular in exterior configuration with a semi-circular cut-out 661 on the interior side. The cut-out 661 may have other configurations as long as the screw 645 fits through the stops 621 and 623 when the stops 621 and 623 are in contact with one another. The stops 621 and 623 also contain annular or tubular recesses 662 which do not extend through the entire length of the stops 621 and 623. The springs 680 fit into the recesses 662 in each stop 621 and 623. The stops 621 and 623 also contain openings 660 through the center of the stops to allow the stops 621 and 623 to slide axially along the spring guides 664 and 665.

Each moveable stop 621 and 623 may comprise any of a variety of durable materials such as aluminum, stainless steel or other metal known in the medical device arts. Preferably, however, a strong lightweight plastic material such as the polymer "DELRIN," available from DuPont is used. Polymeric blocks or coatings are preferred, due to their ability to slide relatively freely on the spring guides 664 and 665 when biased by the springs 680.

Each of two opposing sides of the stops 621 and 623 contain an aperture 686. The aperture 686 has internal threads complementary to the threads of a pivot screw 688. The pivot screws 688 are threadably engaged to the stops 621 and 623 via the aperture 686.

Two link arms 690 and 692 are pivotably affixed to each pivot screw 688 at a first end thereof. The link arm 690 is connected at a second end to the connector bar 625 which is connected to the cover 602. The link arm 692 is connected at its second end to the connector bar 624 which is connected to the platen 630. The link arms 690 and 692 form a scissor-type configuration which is a mirror image of the configuration of link arms 694 and 696. Together, the four link arms 690, 692, 694 and 696 form an adjustable parallelogram linkage, as will be understood by one of skill in the art. Preferably, an identical parallelogram linkage exists on the opposing vertical wall of moveable stops 621 and 623, as shown in FIG. 92.

Referring to FIG. 93, after the medication bag 640 has been inserted into the base 604 and the base 604 is engaged with the cover 602, the springs 680 are at their point of highest compression. As the springs 680 release force in a direction perpendicular to the direction of travel of the platen 630, the stops 621 and 623 slide toward each other on the spring guides 664 and 665, causing the second ends of link arms 690, 692, 694 and 696 to move further apart. Through this mechanism, the force exerted by the springs 680 is transmitted through the link arms 690, 692, 694 and 696 to the platen 630 through the bar receivers 632 and 634. The spring force component transmitted by the link arms 690, 692, 694 and 696 to the platen 630 increases throughout the dispensation cycle of the medication bag 640 as the tension of the springs 680 decreases so as to maintain a substantially constant medication output pressure until the medication bag 640 is substantially collapsed, as shown in FIG. 94. Increasing the force throughout the dispensation cycle, as shown above in Experiments 2 and 3, generates a substantially constant output fluid pressure. A constant fluid pressure is highly desirable for dispensing a variety of drugs such as chemotherapeutic agents. As discussed above, the present invention preferably has dispensation cycles as long as eight days. During an eight day dispensation cycle, one drop of medication is dispensed approximately every 12 minutes. The ability to maintain a substantially constant output fluid pressure is critical in sustaining such a steady flow of medication over an extended time frame. Importantly, the force delivered by the platen 630 on the fluid delivery bag 640 increases through the dispensation cycle resulting in a constant flow rate of medication to a patient.

Figure 95:
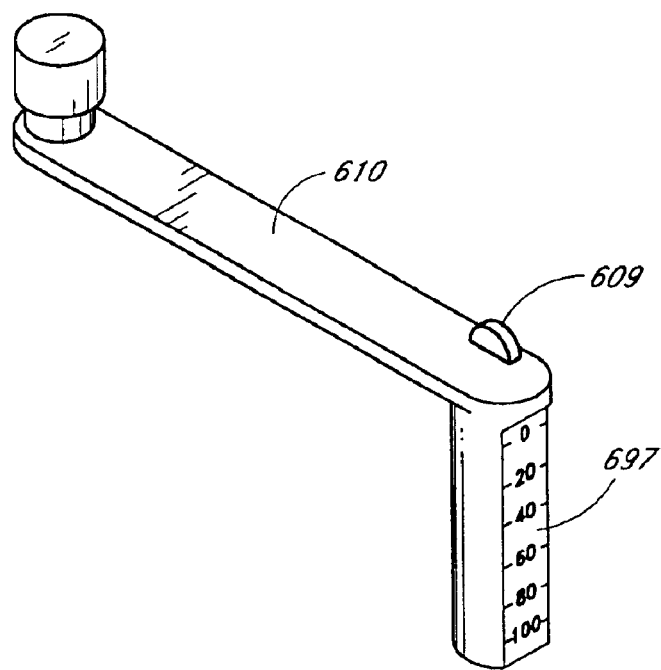
FIG. 95 is a perspective view of the handle of the alternative embodiment shown in FIG. 90.
Figure 96:
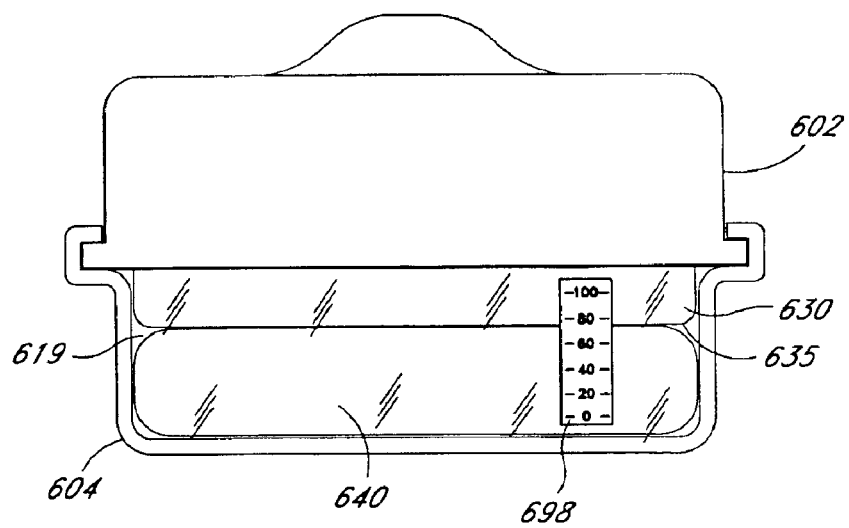
FIG. 96 illustrates a scale on the alternative embodiment of the pump shown in FIG. 90.

During the dispensation cycle, it may be desirable to know the amount of medication remaining in the medication bag 640. As shown in FIGS. 95 and 96, a level indicator is provided on the handle 610. During medicine dispensation, the handle 610 can be inserted in the aperture 614. As the medicine is dispensed from the bag 640, the platen 630 and the bolt 645 will move into the chamber 646 of the base 604. As a result, an end 699 of the bolt 645 is lowered in the aperture 614. The level indicator 697 is calibrated to show the amount of medicine left to be dispensed. This amount is determined by the location of the end 699 of the bolt 645.

FIG. 96 shows an alternative embodiment of indicating the medication level. In this embodiment, an indicator 698 is placed on the face 619 of the base 604. The indicator 698 can be embodied in many forms, including affixing a sticker to the base 604 or incorporated in the injection molding. As the medication is dispensed from the medication bag 640, the platen 630 moves toward the base 604. The remaining fluid level is determined by viewing the location of the bottom 635 of the platen 630 against the indicator 698.

In operation, a full medication bag 640 is attached to the patient by means of a catheter or intravenously via the fluid line 648. The cover 602 and the base 604 are separated by turning the handle 610, thus drawing the platen 630 into the base 602 and slidably disengaging the cover 602 and base 604. The patient inserts the medication bag 640 into the base 604, ensuring the injection port is inside compartment 653 and the fluid delivery port is inside compartment 655. The fluid line 648 protrudes from the base 604 via the port 650. With the platen 630 fully stored in the cover 602, the cover 602 and the base 604 are slidably engaged. The patient then turns the handle 610 until it disengages from the bolt 645. At this point, the end 699 of the bolt 645 us located within the aperture 614. The handle 610 may be stored in the handle storage recess 608. With the handle 610 removed, the linkage assembly 620 and platen 630 apply a steadily increasing force on the medication bag 640 through the dispensation cycle as described above. This force causes the platen 630 to compress the medication bag 640, thereby providing substantially constant fluid flow via the fluid line 648.

After all the medication is dispensed, the patient may remove the handle 610 from the handle storage recess 608 and insert the handle 610 into the aperture 614. The handle 610 is then turned to threadably engage the bolt 645, thereby compressing the linkage assembly 620 and raising the platen 630 into the cover 602. When the platen is again fully stored in the cover 602, the cover 602 and the base 604 can be slidably disengaged. The empty medication bag 640 is removed from the base 604 and the pump 600 is ready to repeat the process.

Numerous variations and modifications of the invention will become readily apparent to those skilled in the art. Accordingly, the invention may be embodied in other specific forms without departing from its spirit or essential characteristics. The detailed embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An ambulatory infusion pump for expelling fluid from a fluid reservoir bag, comprising:

a generally rectangular housing defining a longitudinal central axis, said housing having an interior space therein;

a first wall within said interior space defining a first surface for contacting said fluid reservoir bag;

a second wall within said interior space defining a second surface for contacting said fluid reservoir bag, said second surface facing said first surface, said second wall being moveable between a first position and a second position relative to said first wall, said second position being closer than said first position;

an elongated first guide rod and an elongated second guide rod spaced from said central axis on opposing sides thereof, said first and second guide rods being oriented generally parallel to said central axis;

a first moveable stop and a second moveable stop, each of said first and second movable stops being slideably engaged with each of said first and second guide rods;

at least one parallelogram linkage assembly having first and second opposing pivots connected to said housing and said second wall, respectively, and third and fourth opposing pivots connected to said first and second moveable stops, respectively; and at least one spring configured apply a force tending to bias said first and second stops toward one another, thereby moving said third and fourth pivots toward one another and moving said first and second pivots away from one another to move said second wall toward said second position.

2. The infusion pump of claim 1, wherein said at least one spring comprises four springs, wherein a first and second of said four springs are supported by said first guide rod and said second guide rod, respectively, and being arranged to bias said first moveable stop in a first direction, and a third and fourth of said four springs are supported by said first guide rod and said second guide rod, respectively, and being arranged to bias said second moveable stop in a second direction, opposite said first direction.

3. The infusion pump of claim 1, wherein said at least one parallelogram linkage comprises a first linkage and a second linkage, said first and second linkages being positioned on opposing outward sides of said first and second guide rods.

4. The infusion pump of claim 1, wherein said interior space of said housing is configured to receive a standard, rectangular medication bag.

5. The infusion pump of claim 4, wherein said medication bag includes a fluid injection port, a fluid delivery port, and a fluid reservoir portion, said first and second surfaces contacting only the fluid reservoir portion of said medication bag.

6. The infusion pump of claim 5, wherein said housing additionally includes an internal wall defining at least one compartment sized and shaped to receive the fluid injection port and the fluid delivery port.

7. The infusion pump of claim 1, wherein said first and second surfaces are non-planar surfaces complementary to one another.

* * * * *